United States Patent [19]
Holton et al.

[11] Patent Number: 5,861,487
[45] Date of Patent: Jan. 19, 1999

[54] GENETIC SEQUENCES ENCODING FLAVONOID PATHWAY ENZYMES AND USES THEREFOR

[75] Inventors: Timothy Albert Holton, Northcote; Edwina Cecily Cornish, Upper Beaconsfield; Filippa Kovacic, Preston; Yoshikazu Tanaka, Rosanna; Diane Ruth Lester, Triabunna, all of Australia

[73] Assignee: International Flower Developments Pty. Ltd., Victoria, Australia

[21] Appl. No.: 502,046

[22] Filed: Jul. 14, 1995

Related U.S. Application Data

[63] Continuation of Ser. No. 285,309, Aug. 3, 1994, Pat. No. 5,569,832, which is a continuation of Ser. No. 912,900, Jul. 13, 1992, Pat. No. 5,349,125.

[30] Foreign Application Priority Data

Jul. 11, 1991 [AU] Australia .......................... PK 7173/91
Feb. 17, 1992 [AU] Australia .......................... PL 0923/92

[51] Int. Cl.⁶ .............................. C07K 14/415; C12N 9/04
[52] U.S. Cl. ........................ 530/370; 435/69.1; 435/71.1; 435/70.1; 435/190
[58] Field of Search ................................. 435/69.1, 71.1, 435/70.1, 190; 530/370

[56] References Cited

U.S. PATENT DOCUMENTS 5,034,323 7/1991 Jorgensen et al. ................... 435/172.3

OTHER PUBLICATIONS

Boswell et al. Computational Molecular Biology. Sources and Methods for Sequence Analysis, (Lesk, ed.) Oxford University Press, Oxford, 1988, pp. 170–171.
Bozak et al. (May 1990) "Sequence analysis of ripening-related cytochrome P–450 cDNAs from avocado fruit," *Proc. Natl. Acad. Sci. USA* 87, 3904–3908.
Bozak et al. (1992) "Expression of a Ripening-Related Avocado (*Persea Americana*) Cytochrome P450 in Yeast," *Plant Physiol.* 100, 1976–1981.
Forkmann (1990) "Flavonoids as Flower Pigments: The Formation of the Natural Spectrum and its Extension by Genetic Engineering," *Plant Breeding 106*, 1–26.
Fuqua et al. (1990) "A simple polymerase chain reaction method for detection and cloning of low–abundance transcripts," *BioTechniques* 9(2), 206–210.
Van der Krol et al. (1990) "Inhibition of flower pigmentation by antisense CHS genes: promoter and minimal sequence requirements for the antisense effect," *Plant Molecular Biology 14*, 457–466.
Vaughn et al. (1978) "Flavonoid Genetics of the 28–Chromosome 'Siberian' Iris," *Theor. Appl. Genet.* 51:247.

*Primary Examiner*—Che S. Chereskin
*Attorney, Agent, or Firm*—Scully, Scott, Murphy & Presser

[57] ABSTRACT

The present invention relates to a nucleic acid isolate comprising a sequence of nucleotides encoding, or complementary to a sequence encoding, a dihydrokaempferol (DHK) hydroxylating enzyme or derivative or part thereof. The present invention also relates to transgenic plants carrying and expressing the above mentioned nucleic acid material.

9 Claims, 39 Drawing Sheets

FIGURE 1A

Figure 1A:
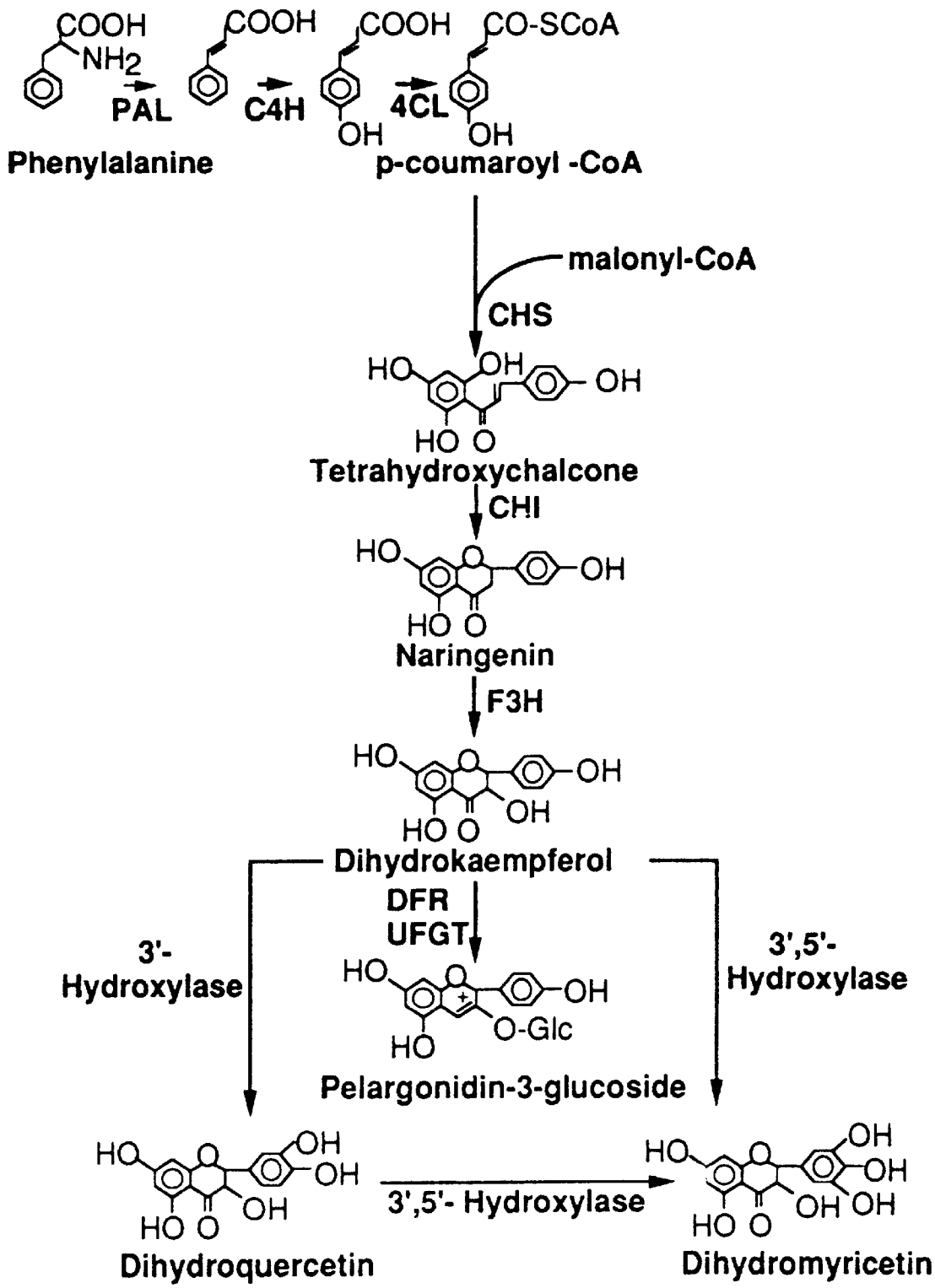
Figure 1B:
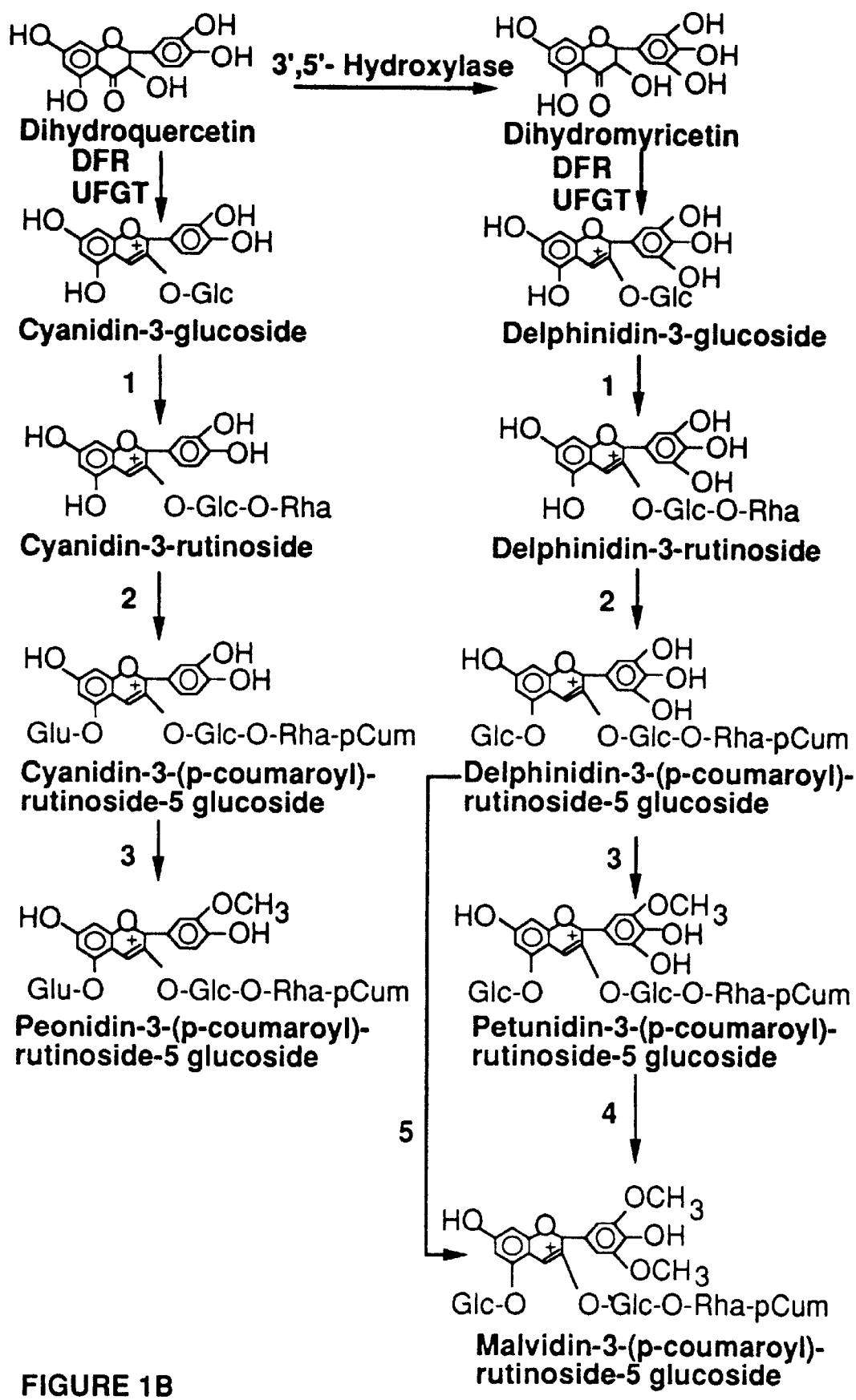

FIGURE 1B pCGP 142

```
  F   S   S   I   R   N   D   E   I   S   S   L
 TTT AGT TCA ATT CGG AAT GAT GAG ATT TCG AGT CTC

I   S   S   I   H   S   M   N   G   S   V   V
 ATT TCA TCA ATT CAT TCC ATG AAC GGT TCT GTT GTC

N   M   T   Q   K   I   L   C   F   T   N   S
 AAC ATG ACA CAA AAG ATT CTT TGT TTT ACA AAC TCT

V   T   C   R   T   A   F   G   K   V   Y   K
 GTG ACT TGT AGA ACA GCT TTC GGG AAA GTA TAC AAA

N   Q   N   E   L   I   N   L   M   R   E   V
 AAT CAA AAT GAA TTG ATA AAC TTG ATG AGG GAA GTA

L   E   L   V   G   G   F   D   ----------------
 CTG GAA TTA GTA GGA GGA TTT GAT ----------------

F   E   N   S   P   V   E   F   I   G   N   H
 TTT GAA AAT TCT CCG GTT GAG TTT ATT GGA AAT CAC

F   E   L   V   P   F   G   A   G   K   R   I
 TTT GAG CTT GTT CCG TTT GGT GCA GGA AAA AGG ATT

C   P   G   M   Q   F   G   L   A   N   I   R
 TGT CCA GGA ATG CAA TTT GGT TTA GCT AAT ATT AGA

H   P   L   A   R   F   L   Y   H   F   N   W
 CAT CCT TTG GCT CGA TTC CTC TAC CAT TTT AAC TGG

A   L   P   Y   E   T   N   P   E   D   L   D
 GCG CTT CCA TAT GAA ACT AAT CCT GAA GAT TTA GAT

S   L   K   N   M   D
 AGT CTG AAA AAT ATG GAT TAA GTGCAGCAAAAGAGAAAGA
TCTATACTTAATTGCCGTAGATCACAAGAAGGTGATATATAAATTC
TGATGTTCTGCTTTAAATGGTGAAAGTCATACTCTACACAATGCTTC
ATCTCCTTAATTTGAGTTTGGTGTACATTTGTGTCTCCTTTTAGCT
TTGAATTTCACCTTGAAAAATGATCACATTTTCTTTTTCTGTTACTC
CAATTAAGATATATGTTGTGGTTGGTCAATTATGCCATATTTATCAA
AAGATCAAATCAATTCCCTCGTTGATAAGTATAGATTATAAAACTGA
TTAATGAATCAAAAAAAAAAAAAAAAA
```

FIGURE 4B pCGP147

```
          Q   F   F   N   L   V   S   F   L   L   I   V   F   S   L
         TGCAATTTTTCAACTTGGTTTCCTTTCTCCTTATTGTATTTTCCCTC
                  10        20        30        40
         ──────────────────────▶
          I   S   L   R   K   W   K   K   S   N   C   Q   T   K   K   L
         ATTTCATTAAGAAAATGGAAGAAATCCAATTGTCAAACCAAAAAATTG
                  58        68        78        88

P   P   G   P   W   K   V   P   F   L   G   S   L   L   H   M
         CCTCCAGGCCCATGGAAAGTACCTTTTCTTGGAAGCTTGCTTCATATG
                 106       116       126       136

V   G   G   L   P   H   H   V   L   R   D   L   A   K   K   Y
         GTAGGTGGACTTCCACACCATGTCCTTAGAGATTTAGCCAAAAAATAT
                 154       164       174       184

G   P   I   M   H   L   Q   L   G   K   I   S   A   V   V   V
         GGACCAATTATGCACCTTCAACTAGGTAAAATTTCTGCCGTTGTAGTT
                 202       212       222       232

T   S   P   E   M   A   R   K   V   L   K   T   H   D   L   A
         ACTTCTCCTGAGATGGCAAGAAAAGTACTAAAAACTCATGACCTTGCA
                 250       260       270       280

F   A   Y   R   P   K   L   L   G   I   E   I   V   C   Y   N
         TTTGCATATAGGCCTAAACTTCTAGGCATTGAGATTGTCTGCTATAAT
                 298       308       318       328

S   S   D   I   A   F   S   P   Y   G   D   Y   W   R   Q   M
         AGTTCAGACATTGCCTTTTCCCCGTATGGTGATTACTGGAGGCAAATG
                 346       356       366       376

R   K   I   C   V   L   E   V   L   S   A   K   N   V   R   S
         CGTAAAATTTGTGTATTGGAAGTGCTTAGTGCCAAAAATGTCCGGTCA
                 394       404       414       424

F   N   S   I   R   R   D   E   I   L   L   M   I   D   F   L
         TTTAACTCGATTAGACGAGATGAAATACTTCTTATGATCGATTTTTTG
                 442       452       462       472

R   S   S   S   G   K   P   V   N   I   T   E   R   I   F   S
         CGATCATCTTCTGGTAAGCCAGTTAATATAACAGAAAGGATCTTTTCA
                 490       500       510       520
```

FIGURE 4C

```
  F   T   S   S   M   I   C   R   S   V   F   G   K   R   I   K
TTCACAAGCTCTATGATTTGTAGATCAGTATTTGGGAAAAGAATAAAG
      538         548         558         568

E   K   D   E   C   I   R   H   V   K   K   M   T   G   L   I
GAGAAAGACGAATGTATACGACATGTGAAAAAAATGACAGGCTTAATA
      586         596         606         616

D   G   F   D   V   A   D   I   F   P   S   L   R   F   L   H
GATGGGTTCGATGTGGCTGACATATTCCCTTCGTTGAGGTTTCTTCAT
      634         644         654         664

V   L   I   G   M   K   G   K   I   M   D   V   H   R   K   V
GTACTAATCGGTATGAAGGGTAAAATTATGGATGTTCATCGTAAGGTA
      682         692         702         712

D   A   I   V   E   E   V   M   N   E   H   K   E   T   L   R
GATGCTATTGTTGAGGAAGTCATGAATGAGCACAAAGAAACTCTTCGA
      730         740         750         760

T   G   K   T   N   G   E   V   G   G   E   D   L   I   D   V
ACTGGCAAGACCAATGGTGAAGTGGGAGGAGAAGATTTAATTGATGTA
      778         788         798         808

L   L   R   L   K   E   E   G   D   L   Q   L   P   I   T   N
TTGCTAAGACTTAAGGAAGAGGGAGACCTTCAACTTCCAATCACAAAT
      826         836         846         856

D   N   I   K   A   I   F   N   D   M   F   A   A   G   T   E
GACAACATCAAAGCCATTTTTAATGACATGTTTGCTGCGGGAACAGAA
      874         884         894         904

T   S   S   T   T   I   N   W   A   M   V   E   L   M   K   N
ACTTCATCAACAACAATTAACTGGGCCATGGTAGAACTGATGAAAAAT
      922         932         942         952

P   S   V   F   A   K   A   Q   A   E   V   R   E   V   F   K
CCAAGTGTATTCGCGAAAGCTCAAGCAGAGGTAAGAGAAGTCTTCAAA
      970         980         990         1000

G   K   E   T   F   D   E   D   D   I   E   E   L   N   Y   L
GGGAAAGAAACTTTCGATGAAGATGATATCGAGGAGCTGAATTACCTT
      1018        1028        1038        1048

K   L   V   I   R   E   T   L   R   L   H   P   P   L   P   L
AAGTTAGTCATTAGAGAAACTTTAAGACTCCACCCTCCACTTCCACTT
      1066        1076        1086        1096
```

FIGURE 4D

```
          L  L  P  R  E  C  R  R  E  T  E  I  N  G  Y  T
        TTGCTTCCAAGAGAATGTCGGAGAGAAACAGAAATAAATGGCTACACT
              1114      1124      1134      1144

I  P  L  N  T  K  V  I  V  N  V  W  A  I  G  R
        ATTCCTTTAAATACCAAAGTCATAGTTAATGTTTGGGCTATTGGAAGA
              1162      1172      1182      1192

D  P  K  Y  W  D  D  A  E  S  F  K  P  E  R  F
        GATCCAAAATATTGGGATGATGCAGAAAGCTTTAAGCCTGAGAGATTT
              1210      1220      1230      1240

E  H  N  S  L  N  F  A  G  N  N  F  E  Y  L  P
        GAACATAACTCTTTGAATTTTGCTGGCAATAATTTTGAATATCTTCCT
              1258      1268      1278      1288

F  G  S  G  R  R  I  C  P  G  I  S  F  G  L  A
        TTTGGTAGTGGAAGGAGGATTTGCCCCGGAATATCATTTGGTTTAGCT
              1306      1316      1326      1336

N  V  Y  H  P  L  A  Q  L  L  Y  H  F  D  W  R
        AATGTTTATCATCCATTGGCTCAATTGTTGTATCATTTCGATTGGAGA
              1354      1364      1374      1384

L  P  T  G  V  D  P  N  D  F  E  L  T  S  *
        CTTCCTACTGGGGTCGACCCAAATGACTTTGAATTGACTAGTTAGCTG
              1402      1412      1422      1432
        ◄─────────────────

GAGTAACTACTGGTAGGAAAAGAGACCTTTACTTGATTTTCACTCCTT
              1450      1460      1470      1480

ATTCACCTTCTCTAAAGTGATTAAATGG-GCAAATTTTAATTTGAAAT
              1498      1508      1518      1528

AATACTTTTTCTTGTTTACATTTCTCTCCCATTGTTGTATTTCATTTA
              1546      1556      1566      1576

CCTATTGTTGTACTTCTTTCTTTTGTTGATGTCTTAGGTTTTACCTAT
              1594      1604      1614      1624

TTCTATGCATTTGTATTTAAAAAAAAAAAAAAAAAA
              1642      1652      1662
```

FIGURE 4E pCGP158

```
Gly Met Met Lys Gln Gly Asp Phe Leu Asp Val Leu
GGG ATG ATG AAG CAA GGA GAT TTC TTG GAT GTA CTT
    ─────────────────▶

Leu Asp Gln Cys Asp Glu Glu Gly Ser Gly Phe Asp
CTT GAT CAA TGT GAT GAA GAA GGG TCT GGA TTT GAT

Arg Gln Thr Ile Lys Pro Leu Ile Leu Asp Leu Phe
CGC CAA ACT ATC AAG CCT CTC ATC CTG GAT TTA TTC

Ile Ala Gly Ser Asp Thr Ser Ala Ile Thr Thr Glu
ATT GCT GGA AGT GAT ACA TCT GCC ATA ACA ACA GAA

Trp Ala Met Ala Glu Leu Leu Arg Lys Pro Gln Glu
TGG GCA ATG GCA GAA CTA CTT CGA AAA CCT CAA GAA

────────────────────────────────────────────────
────────────────────────────────────────────────

Phe Val Asn Ala Trp Ala Ile Gly Arg Asp Pro Lys
TTT GTG AAT GCA TGG GCA ATT GGA AGA GAT CCA AAA

Tyr Trp Glu Lys Pro Leu Glu Phe Met Pro Glu Arg
TAC TGG GAA AAA CCA CTG GAG TTT ATG CCT GAA AGA

Phe Leu Lys Cys Ser Leu Asp Tyr Lys Gly Arg ---
TTC TTG AAG TGT AGT TTG GAT TAC AAA GGT AGG G--

Phe Glu Tyr Ile Pro Phe Gly Ala Gly Arg Arg Ile
TTT GAG TAT ATA CCA TTT GGC GCA GGT CGA AGA ATT

Cys Pro Gly Met Pro His Cys Asn Lys Asp Gly Glu
TGT CCT GGA ATG CCA CAT TGC AAT AAG GAT GGT GAA

Phe Asp Ala Gly Phe Asp Tyr Ser Pro Phe Ser Trp
TTT GAT GCT GGC TTC GAT TAT TCA CCA TTT AGT TGG

Glu Leu Pro --- Gly Met Ala Pro Lys --- Leu Asn
GAA TTA CCT -AA GGA ATG GCA CCA AAG -AT TTG AAC

Met Glu Glu Gln Phe Gly Val Thr Leu Arg Lys Ala
ATG GAG GAA CAG TTT GGA GTT ACC TTG AGG AAG GCT

Ile Pro Leu Ile Ala Ile Pro Ser Met Glu Glu Lys
ATT CCC CTT ATT GCC ATT CCC AGT ATG GAA GAA AAG

Val Ile Phe
GTC ATA TTT TAG CCCAAAAGCTATGCATTTTGTGTGTATGTTT
             ◀────────────────────────────────
```

FIGURE 4F pCGP 160

```
  K   Q   I   N   A   L   L   V   E   I   F   G
 AAA CAG ATC AAT GCA TTG CTT GTG GAA ATA TTT GGA
 ────────────────────────────▶
  A   G   T   E   S   T   T   A   T   S   Q   W
 GCT GGT ACA GAA TCT ACA ACT GCT ACA AGC CAA TGG

M   L   V   E   L   L   R   N   R   Q   A   L
 ATG CTT GTA GAA CTC CTT AGA AAT CGA CAA GCC TTG

─────────────   P   K   D   T   Q   V   M   V   N
 ─────────────CCC AAA GAC ACT CAA GTT ATG GTA AAC

E   W   A   I   A   Y   D   P   K   I   W   G
 GAG TGG GCG ATT GCG TAT GAT CCT AAG ATT TGG GGC

S   F   K   P   Q   R   F   I   D   S   K   I
 AGC TTC AAA CCC GAA AGG TTT ATC GAT TCA AAA ATA

D   P   L   D   H   K   G   Q   N   F   E   Y
 GAT CCT TTG GAC CAC AAA GGG CAA AAT TTT GAA TAT

F   P   F   G   S   G   R   R   I   C   A   G
 TTT CCT TTT GGT TCT GGA AGG AGA ATT TGT GCT GGA

E   P   L   A   S   R   V   I   P   L   A   V
 GAA CCT TTG GCT TCT AGG GTT ATT CCC TTA GCT GTT

A   S   M   I   H   K   F   ─────────
 GCT TCT ATG ATC CAT AAG TTT ─────────GATATCACTAT
                         ◀─────────────
GTTAGAAGATCCACTCTCATCATTCCTAAGTTGAGAAGAGTGAGGAA

ATTAAAAGAAGCAGAAGATATGTTACTATAAAACTCGTTATATATA

TATATATTGCTGTATCTATATATGTGTGAATGATCTGCTGCTCATGT

TGTGTTTTGTTGTTTGTGTACTATAGGTCATACCTAAGTTGATGAAA

TGTCTCTGAGAATATATACTCCTTATATAATAGGAGTAATTTACCGA

TAATTAATATTCCTGCGACAAAAAAAAAAAAAAAA
```

FIGURE 4G pCGP454

```
      -    R    E    S    M    E    D    V    R    L    L    G
     CT  CGA  GAA  TCA  ATG  GAA  GAT  GTA  AGA  TTA  CTA  GGC
     ────────────────────▶

Y    H    I    P    A    K    T    R    L    F    I    N
     TAT  CAC  ATA  CCT  GCT  AAA  ACG  AGA  CTC  TTT  ATC  AAT

A    W    T    M    G    R    D    P    L    T    W    E
     GCT  TGG  ACA  ATG  GGG  AGA  GAC  CCA  CTA  ACA  TGG  GAA

N    P    E    E    Y    Q    P    E    R    F    L    N
     AAT  CCA  GAA  GAG  TAT  CAG  CCA  GAG  AGA  TTC  TTG  AAT

R    D    T    D    V    K    G    V    N    F    E    F
     AGA  GAT  ACT  GAT  GTC  AAA  GGA  GTA  AAC  TTT  GAG  TTC

I    P    F    G    A    G    R    S
     ATT  CCC  TTT  GGC  GCC  GGC  AGA  AGC
                       ◀────────────────────
```

FIGURE 9D pCGP 602

```
  CTTTCTACTAGCTACTTCGTTATATATATGTAAAATTGTGACTTT
       10        20        30        40

GAAAATCATTTAAATTATCATAAGGTTCATTTTATCTTGATCAAA
       55        65        75        85

M   M   L
  ATATTTACTTCGGCCATATACGTTTTCCTTTAGTCATGATGCTAC
       100       110       120       130

L  T  E  L  G  A  A  T  S  I  F  L  I  A  H
  TTACTGAGCTTGGTGCAGCAACTTCAATCTTTCTAATAGCACACA
       145       155       165       175

I  I  I  S  T  L  I  S  K  T  T  G  R  H  L
  TAATCATTTCAACTCTTATTTCAAAAACTACCGGCCGGCATCTAC
       190       200       210       220

P  P  G  P  R  G  W  P  V  I  G  A  L  P  L
  CGCCGGGGCCAAGAGGGTGGCCGGTGATCGGAGCACTTCCACTTT
       235       245       255       265

L  G  A  M  P  H  V  S  L  A  K  M  A  K  K
  TAGGAGCCATGCCACATGTTTCCTTAGCTAAAATGGCAAAAAAT
       280       290       300       310

Y  G  A  I  M  Y  L  K  V  G  T  C  G  M  A
  ATGGAGCAATCATGTATCTCAAAGTTGGAACATGTGGCATGGCAG
       325       335       345       355

V  A  S  T  P  D  A  A  K  A  F  L  K  T  L
  TTGCTTCTACCCCTGATGCTGCTAAAGCATTCTTGAAAACACTTG
       370       380       390       400

D  I  N  F  S  N  R  P  P  N  A  G  A  T  H
  ATATCAACTTCTCCAATCGTCCACCTAATGCAGGTGCCACTCACT
       415       425       435       445

L  A  Y  N  A  Q  D  M  V  F  A  H  Y  G  P
  TAGCTTATAATGCTCAAGACATGGTTTTTGCACATTATGGACCAC
       460       470       480       490

R  W  K  L  L  R  K  L  S  N  L  H  M  L  G
  GATGGAAGTTGCTAAGGAAATTAAGCAACTTGCATATGCTAGGGG
       505       515       525       535
```

FIGURE 9A

```
G   K   A   L   E   N   W   A   N   V   R   A   N   E   L
GAAAAGCCTTAGAGAATTGGGCAAATGTTCGTGCCAATGAGCTAG
      550         560         570         580

G   H   M   L   K   S   M   S   D   M   S   R   E   G   Q
GGCACATGCTAAAATCAATGTCCGATATGAGTCGAGAGGGCCAGA
      595         605         615         625

R   V   V   V   A   E   M   L   T   F   A   M   A   N   M
GGGTTGTGGTGGCGGAGATGTTGACATTTGCCATGGCCAATATGA
      640         650         660         670

I   G   Q   V   M   L   S   K   R   V   F   V   D   K   G
TCGGACAAGTGATGCTAAGCAAAAGAGTATTTGTAGATAAAGGTG
      685         695         705         715

V   E   V   N   E   F   K   D   M   V   V   E   L   M   T
TTGAGGTAAATGAATTTAAGGACATGGTTGTAGAGTTAATGACAA
      730         740         750         760

I   A   G   Y   F   N   I   G   D   F   I   P   C   L   A
TAGCAGGGTATTTCAACATTGGTGATTTTATTCCTTGTTTAGCTT
      775         785         795         805

W   M   D   L   Q   G   I   E   K   R   M   K   R   L   H
GGATGGATTTACAAGGGATAGAAAAACGAATGAAACGTTTACATA
      820         830         840         850

K   K   F   D   A   L   L   T   K   M   F   D   E   H   K
AGAAGTTTGATGCTTTATTGACAAAGATGTTTGATGAACACAAAG
      865         875         885         895

A   T   T   Y   E   R   K   G   K   P   D   F   L   D   V
CAACTACCTATGAACGTAAGGGGAAACCAGATTTTCTTGATGTTG
      910         920         930         940

V   M   E   N   G   D   N   S   E   G   E   R   L   S   T
TTATGGAAAATGGGGACAATTCTGAAGGAGAAAGACTCAGTACAA
      955         965         975         985

T   N   I   K   A   L   L   N   L   F   T   A   G   T
CCAACATCAAAGCACTTTTGCTGAATTTGTTCACAGCTGGTACGG
     1000        1010        1020        1030
```

FIGURE 9B

```
D   T   S   S   S   A   I   E   W   A   L   A   E   M   M
ACACTTCTTCTAGTGCAATAGAATGGGCACTTGCAGAAATGATGA
        1045        1055        1065        1075

K   N   P   A   I   L   K   K   A   Q   A   E   M   D   Q
AGAACCCTGCCATTTTGAAAAAAGCACAAGCAGAAATGGATCAAG
        1090        1100        1110        1120

V   I   G   R   N   R   R   L   L   E   S   D   I   P   N
TCATTGGAAGAAATAGGCGTTTACTCGAATCCGATATCCCAAATC
        1135        1145        1155        1165

L   P   Y   L   R   A   I   C   K   E   T   F   R   K   H
TCCCTTACCTCCGAGCAATTTGCAAAGAAACATTTCGAAAACACC
        1180        1190        1200        1210

P   S   T   P   L   N   L   P   R   I   S   N   E   P   C
CTTCTACACCATTAAATCTTCCTAGGATCTCGAACGAACCATGCA
        1225        1235        1245        1255

I   V   D   G   Y   Y   I   P   K   N   T   R   L   S   V
TAGTCGATGGTTATTACATACCAAAAAACACTAGGCTTAGTGTTA
        1270        1280        1290        1300

N   I   W   A   I   G   R   D   P   Q   V   W   E   N   P
ACATATGGGCAATTGGAAGAGATCCCCAAGTTTGGGAAAATCCAC
        1315        1325        1335        1345

L   E   F   N   P   E   R   F   L   S   G   R   N   S   K
TAGAGTTTAATCCCGAAAGATTCTTGAGTGGAAGAAACTCCAAGA
        1360        1370        1380        1390

I   D   P   R   G   N   D   F   E   L   I   P   F   G   A
TTGATCCTCGAGGGAACGATTTTGAATTGATACCATTTGGTGCTG
        1405        1415        1425        1435

G   R   R   I   C   A   G   T   R   M   G   I   V   M   V
GACGAAGAATTTGTGCAGGAACAAGAATGGGAATTGTAATGGTGG
        1450        1460        1470        1480

E   Y   I   L   G   T   L   V   H   S   F   D   W   K   L
AATATATATTAGGAACTTTGGTTCATTCATTTGATTGGAAATTAC
        1495        1505        1515        1525
```

FIGURE 9C

```
  P   S   E   V   I   E   L   N   M   E   E   A   F   G   L
CAAGTGAAGTTATTGAGTTGAATATGGAAGAAGCTTTTGGCTTAG
       1540        1550        1560        1570

A   L   Q   K   A   V   P   L   E   A   M   V   T   P   R
CTTTGCAGAAAGCTGTCCCTCTTGAAGCTATGGTTACTCCAAGGT
       1585        1595        1605        1615

L   Q   L   D   V   Y   V   P   *
TACAATTGGATGTTTATGTACCATAGCTATAGATGTGTATTGTGC
       1630        1640        1650        1660

TATAATTGCGCATGTTGTTGGTTGTAGCATGAGATATTAAAAGGA
       1675        1685        1695        1705

GTACATGAAGCGCATTGCATGAGTTTAACTTGTAGCTCCTTAATA
       1720        1730        1740        1750

TTTTAGGTATTTTTCAATTAATAAGTTCTTGTTGGTTGGGTAAAA
       1765        1775        1785        1795

AAAAAAAAAAA
       1810
```

FIGURE 10C pCGP 175

```
                                              M  V  L  L  S  E
TTGAATCCAGCTCTATCTGGCTTTAGACAATGGTGCTACTTAGTG
         10        20        30        40

L  A  A  A  T  L  I  F  L  T  T  H  I  F  I
AGCTTGCTGCAGCAACCTTAATCTTTCTAACAACACATATCTTCA
         55        65        75        85

S  T  L  L  S  I  T  N  G  R  R  L  P  P  G
TTTCAACTCTTCTTTCTATAACTAACGGCCGGCGTCTCCCGCCAG
        100       110       120       130

P  R  G  W  P  V  I  G  A  L  P  L  L  G  A
GGCCAAGAGGGTGGCCGGTGATCGGAGCACTTCCACTTTTAGGAG
        145       155       165       175

M  P  H  V  S  L  A  K  M  A  K  K  Y  G  A
CCATGCCACATGTTTCCTTAGCTAAAATGGCAAAAAAATATGGAG
        190       200       210       220

I  M  Y  L  K  V  G  T  C  G  M  V  V  A  S
CAATCATGTATCTCAAAGTTGGAACGTGTGGCATGGTAGTTGCTT
        235       245       255       265

T  P  D  A  A  K  A  F  L  K  T  L  D  L  N
CTACCCCTGATGCTGCTAAAGCGTTCTTGAAAACACTTGATCTCA
        280       290       300       310

F  S  N  R  P  P  N  A  G  A  T  H  L  A  Y
ACTTCTCCAATCGTCCACCTAATGCAGGTGCCACCCACTTAGCCT
        325       335       345       355

G  A  Q  D  M  V  F  A  H  Y  G  P  R  W  K
ATGGTGCTCAAGACATGGTTTTTGCACATTATGGACCAAGATGGA
        370       380       390       400

L  L  R  K  L  S  N  L  H  M  L  G  G  K  A
AGTTGCTAAGGAAATTAAGCAACTTACATATGCTAGGGGGGAAAG
        415       425       435       445

L  E  N  W  A  N  V  R  A  N  E  L  G  H  M
CCTTAGAAAATTGGGCAAATGTTCGTGCCAATGAGCTAGGACACA
        460       470       480       490

L  K  S  M  F  D  M  S  R  E  G  E  R  V  V
TGCTAAAATCGATGTTTGATATGAGCAGAGAAGGGGAGAGAGTTG
        505       515       525       535
```

FIGURE 10A

```
         V  A  E  M  L  T  F  A  M  A  N  M  I  G  Q
      TGGTGGCGGAGATGTTGACATTTGCCATGGCGAATATGATCGGAC
           550         560         570         580

V  I  L  S  K  R  V  F  V  N  K  G  V  E  V
      AGGTGATACTTAGCAAAAGAGTATTTGTAAATAAAGGTGTTGAGG
           595         605         615         625

N  E  F  K  D  M  V  V  E  L  M  T  T  A  G
      TAAATGAATTTAAGGACATGGTGGTAGAGTTAATGACAACAGCAG
           640         650         660         670

Y  F  N  I  G  D  F  I  P  C  L  A  W  M  D
      GGTATTTTAACATTGGTGATTTTATTCCTTGTTTAGCTTGGATGG
           685         695         705         715

L  Q  G  I  E  K  G  M  K  R  L  H  K  K  F
      ATTTACAAGGGATAGAAAAAGGAATGAAACGTTTACATAAGAAGT
           730         740         750         760

D  A  L  L  T  K  M  F  D  E  H  K  A  T  S
      TTGATGCTTTATTGACAAAGATGTTTGATGAACACAAAGCAACTA
           775         785         795         805

Y  E  R  K  G  K  P  D  F  L  D  C  V  M  E
      GCTATGAACGTAAGGGGAAACCAGATTTTCTTGATTGTGTTATGG
           820         830         840         850

N  R  D  N  S  E  G  E  R  L  S  T  T  N  I
      AAAATAGGGACAATTCTGAAGGAGAAAGGCTCAGTACAACCAACA
           865         875         885         895

K  A  L  L  L  N  L  F  T  A  G  T  D  T  S
      TCAAAGCACTCTTGCTGAATTTGTTCACAGCTGGTACAGACACTT
           910         920         930         940

S  S  A  I  E  W  A  L  A  E  M  M  K  N  P
      CTTCTAGTGCAATAGAATGGGCACTTGCAGAGATGATGAAGAACC
           955         965         975         985

A  I  L  K  K  A  Q  G  E  M  D  Q  V  I  G
      CTGCCATTTTAAAGAAAGCACAAGGAGAAATGGATCAAGTCATTG
          1000        1010        1020        1030

N  N  R  R  L  L  E  S  D  I  P  N  L  P  Y
      GAAACAATAGGCGTCTGCTCGAATCGGATATCCCAAATCTCCCTT
          1045        1055        1065        1075
```

FIGURE 10B

```
        L   R   A   I   C   K   E   T   F   R   K   H   P   S   T
      ACCTCCGAGCAATTTGCAAAGAAACATTTCGAAAGCACCCTTCTA
           1090        1100       1110       1120

P   L   N   L   P   R   I   S   N   E   P   C   I   V   D
      CACCATTAAATCTCCCTAGGATCTCGAACGAACCATGCATTGTCG
           1135        1145       1155       1165

G   Y   Y   I   P   K   N   T   R   L   S   V   N   I   W
      ATGGTTATTACATACCAAAAAACACTAGGCTTAGTGTTAACATAT
           1180        1190       1200       1210

A   I   G   R   D   P   E   V   W   E   N   P   L   E   F
      GGGCAATTGGAAGAGATCCCGAAGTTTGGGAGAACCCACTAGAGT
           1225        1235       1245       1255

Y   P   E   R   F   L   S   G   R   N   S   K   I   D   P
      TTTATCCTGAAAGGTTCTTGAGTGGAAGAAACTCGAAGATTGATC
           1270        1280       1290       1300

R   G   N   D   F   E   L   I   P   F   G   A   G   R   R
      CTCGAGGGAACGACTTTGAATTGATACCATTTGGTGCTGGACGAA
           1315        1325       1335       1345

I   C   A   G   T   R   M   G   I   V   M   V   E   Y   I
      GAATTTGTGCAGGGACAAGAATGGGAATCGTAATGGTGGAATATA
           1360        1370       1380       1390

L   G   T   L   V   H   S   F   D   W   K   L   P   S   E
      TATTAGGAACTTTGGTCCATTCATTTGATTGGAAATTACCAAGTG
           1405        1415       1425       1435

V   I   E   L   N   M   E   E   A   F   G   L   A   L   Q
      AAGTTATTGAGCTAAATATGGAAGAAGCTTTTGGATTAGCTTTGC
           1450        1460       1470       1480

K   A   V   P   L   E   A   M   V   T   P   R   L   P   I
      AGAAAGCTGTCCCTCTTGAAGCTATGGTTACTCCAAGGCTGCCTA
           1495        1505       1515       1525

D   V   Y   A   P   L   A   *
      TTGATGTTTATGCACCTTTAGCTTGAAACATGCCTTTACGTTGGT
           1540        1550       1560       1570

TTCAGTTTTGGGTAGTATAATGTTGTGGTGTTTGGCTATAGAAAT
      ATTAATAAATGCTAGTATCTTGAAGGCGCGTGCAGGGGGAGGGGG
      TTGTCTTAGATAGTAGTAATATGTTAGCCTTCCTTTTATTTCTTG
      TGATTGTGAGAATCTTGATATGTTTTCTTGAAAAAAAAAAAAAA
```

FIGURE 10C

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Phe  Xaa  Xaa  Gly  Xaa  Arg  Xaa  Cys  Xaa  Gly
 1              5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro  Gly  Phe  Ala  Gly  Arg  Arg  Ile  Cys  Pro  Gly
 1              5                        10
```

( 2 ) INFORMATION FOR SEQ ID NO:3:

( i ) SEQUENCE CHARACTERISTICS:

(A) LENGTH: 25 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:3:

GGAAGCTTAT NCCNTTYGGN GCNGG 25

(2) INFORMATION FOR SEQ ID NO:4:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

GGATGACTCA GTAAAACGAC GGCCAGT 27

(2) INFORMATION FOR SEQ ID NO:5:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CCNGGRCANA TNCKYYTNCC NGCNCCRAAN GG 32

(2) INFORMATION FOR SEQ ID NO:6:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GGATGACTCA AACAGCTATG ACCATG 26

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:7:

GTTCAATTCG GAATGATG 18

(2) INFORMATION FOR SEQ ID NO:8:

(i) SEQUENCE CHARACTERISTICS:
(A) LENGTH: 18 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:8:

GCTGCACTTA ATCCATAT                                                                                 18

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:9:

TGCATAGCTT TTGGG                                                                                    15

(2) INFORMATION FOR SEQ ID NO:10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:10:

GAGAGAGAGA GAGAGAGAGA TCTCGAGTTT TTTTTTTTT TTTTT                                                     45

(2) INFORMATION FOR SEQ ID NO:11:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:11:

ATGTCTCCTC CAGTG                                                                                    15

(2) INFORMATION FOR SEQ ID NO:12:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:12:

CTAGACTCCA ATCAC                                                                                    15

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:13:

Pro Phe Gly Ala Gly Arg Arg Gly Cys Pro Gly ( 2 ) INFORMATION FOR SEQ ID NO:14:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Pro Phe Gly Ala Gly Lys Arg Ile Cys Pro Gly
1               5                   10
```

( 2 ) INFORMATION FOR SEQ ID NO:15:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
Pro Phe Gly Ser Gly Arg Arg Ile Cys Pro Gly
1               5                   10
```

( 2 ) INFORMATION FOR SEQ ID NO:16:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CCNTTYGGND SNGGNMRNMG NRKNTGYCCN GGN          33

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CGTGCCAATG AGCTAGG          17

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

GATGTTGGTT GTACTGAG          18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

GGAAACCAGA TTTTCTTG       18

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TTTTTTTTTT TTTTTTTAGC       20

( 2 ) INFORMATION FOR SEQ ID NO:21:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

GTTTTCCCAG TCACGAC       17

( 2 ) INFORMATION FOR SEQ ID NO:22:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

AACAGCTATG ACCATG       16

( 2 ) INFORMATION FOR SEQ ID NO:23:

( i ) SEQUENCE CHARACTERISTICS:
        ( A ) LENGTH: 733 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

TTTAGTTCAA TTCGGAATGA TGAGATTTCG AGTCTCATTT CATCAATTCA TTCCATGAAC     60

GGTTCTGTTG TCAACATGAC ACAAAGATT CTTTGTTTTA CAAACTCTGT GACTTGTAGA     120

ACAGCTTTCG GGAAAGTATA CAAAAATCAA AATGAATTGA TAAACTTGAT GAGGGAAGTA     180

CTGGAATTAG TAGGAGGATT TGATTTTGAA AATTCTCCGG TTGAGTTTAT TGGAAATCAC     240

| | | | | | | |
|---|---|---|---|---|---|---|
| TTTGAGCTTG | TTCCGTTTGG | TGCAGGAAAA | AGGATTTGTC | CAGGAATGCA | ATTTGGTTTA | 300 |
| GCTAATATTA | GACATCCTTT | GGCTCGATTC | CTCTACCATT | TTAACTGGGC | GCTTCCATAT | 360 |
| GAAACTAATC | CTGAAGATTT | AGATAGTCTG | AAAAATATGG | ATTAAGTGCA | GCAAAAGAGA | 420 |
| AAGATCTATA | CTTAATTGCC | GTAGATCACA | AAGAAGGTGA | TATATAAATT | CTGATGTTCT | 480 |
| GCTTTAAATG | GTGAAAGTCA | TACTCTACAC | AATGCTTCAT | CTCCTTAATT | TGAGTTTGGT | 540 |
| GTACATTTGT | GTCTCCCTTT | TAGCTTTGAA | TTTCACCTTG | AAAAATGATC | ACATTTTCTT | 600 |
| TTTCTGTTAC | TCCAATTAAG | ATATATGTTG | TGGTTGGTCA | ATTATGCCAT | ATTTATCAAA | 660 |
| AGATCAAATC | AATTCCCTCG | TTGATAAGTA | TAGATTATAA | AACTGATTAA | TGAATCAAAA | 720 |
| AAAAAAAAAA | AAA | | | | | 733 |

( 2 ) INFORMATION FOR SEQ ID NO:24:

( i ) SEQUENCE CHARACTERISTICS:
        ( A ) LENGTH: 1666 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

| | | | | | | |
|---|---|---|---|---|---|---|
| TGCAATTTTT | CAACTTGGTT | TCCTTTCTCC | TTATTGTATT | TTCCCTCATT | TTCATTAAGA | 60 |
| AAATGGAAGA | AATCCAATTG | TCAAACCAAA | AAATTGCCTC | CAGGCCCATG | GAAAGTACCT | 120 |
| TTTCTTGGAA | GCTTGCTTCA | TATGGTAGGT | GGACTTCCAC | ACCATGTCCT | TAGAGATTTA | 180 |
| GCCAAAAAAT | ATGGACCAAT | TATGCACCTT | CAACTAGGTA | AAATTTCTGC | CGTTGTAGTT | 240 |
| ACTTCTCCTG | AGATGGCAAG | AAAAGTACTA | AAAACTCATG | ACCTTGCATT | TGCATATAGG | 300 |
| CCTAAACTTC | TAGGCATTGA | GATTGTCTGC | TATAATAGTT | CAGACATTGC | CTTTTCCCCG | 360 |
| TATGGTGATT | ACTGGAGGCA | AATGCGTAAA | ATTTGTGTAT | GGAAGTGCT | TAGTGCCAAA | 420 |
| AATGTCCGGT | CATTTAACTC | GATTAGACGA | GATGAAATAC | TTCTTATGAT | CGATTTTTG | 480 |
| CGATCATCTC | TCGGTAAGCC | AGTTAATATA | ACAGAAAGGA | TCTTTTCATT | CACAAGCTCT | 540 |
| ATGATTTGTA | GATCAGTATT | TGGGAAAAGA | ATAAGGAGA | AAGACGAATG | TATACGACAT | 600 |
| GTGAAAAAAA | TGACAGGCTT | AATAGATGGG | TTCGATGTGG | CTGACATATT | CCCTTCGTTG | 660 |
| AGGTTTCTTC | ATGTACTAAT | CGGTATGAAG | GGTAAAATTA | TGGATGTTCA | TCGTAAGGTA | 720 |
| GATGCTATTG | TTGAGGAAGC | TATGAATGAG | CACAAAGAAA | CTCTTCGAAC | TGGCAAGACC | 780 |
| AATGGTGAAG | TGGGAGGAGA | AGATTTAATT | GATGTATTGC | TAAGACTTAA | GGAAGAGGGA | 840 |
| GACCTTCAAC | TTCCAATCAC | AAATGACAAC | ACTAAAGCCA | TTTTTAATGA | CATGTTTGCT | 900 |
| GCGGGAACAG | AAACTTCATC | AACAACAATT | AACTGGGCCA | TGGTAGAACT | GATGAAAAAT | 960 |
| CCACGTGTAT | TCGCGAAAGC | TCAAGCAGAG | GTAAGAGAAG | TCTTCAAAGG | GAAAGAAACT | 1020 |
| TTCGATGAAG | ATGATATCGA | GGAGCTGAAT | TACCTTAAGT | TAGTCATTAG | AGAAACTTTA | 1080 |
| AGATCTCACC | CTCCACTTCC | ACTTTTGCTT | CCAAGAGAAT | GTCGGAGAGA | AACAGAAATA | 1140 |
| AATGGCTACA | CTATTCCTTT | AAATACCAAA | GTCATAGTTA | ATGTTTGGGC | TATTGGAAGA | 1200 |
| GATCCAAAAT | ATTGGGATGA | TGCAGAAAGC | TTTAAGCCTG | AGAGATTTGA | ACATAACTCT | 1260 |
| TTGAATTTTG | CTGGCAATAA | TTTTGAATAT | CTTCCTTTTG | GTAGTGGAAG | GAGGATTTGC | 1320 |
| CCCGGAATAT | CATTTGGTTT | AGCTAATGTG | TATCATCCAT | TGGCTCAATT | GTTGTATCAT | 1380 |
| TTCGATTGGA | GACTTCCTAC | TGGGGTCGAC | CCAAATGACT | TGAATTGAC | TAGTTAGCTG | 1440 |
| GAGTAACTAC | TGGTAGGAAA | AGAGACCTTT | ACTTGATTTT | CACTCCTTAT | TCACCTTCTC | 1500 |

|  |  |  |  |  |  |
|---|---|---|---|---|---|
| TAAAGTGATT | AAATGGGCAA | ATTTTAATTT | GAAATAATAC | TTTTTCTTGT | TTACATTTCT | 1560
| CTCCCATTGT | TGTATTTCAT | TTACCTATTG | TTGTACTTCT | TTCTTTTGTT | GATGTCTTAG | 1620
| GTTTTACCTA | TTTCTATGCA | TTTGTATTTA | AAAAAAAAAA | AAAAAA | | 1666

( 2 ) INFORMATION FOR SEQ ID NO:25:

( i ) SEQUENCE CHARACTERISTICS:
        ( A ) LENGTH: 543 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

|  |  |  |  |  |  |
|---|---|---|---|---|---|
| GGGATGATGA | AGCAAGGAGA | TTTCTTGGAT | GTACTTCTTG | ATCAATGTGA | TGAAGAAGGG | 60
| TCTGGATTTG | ATCGCCAAAC | TATCAAGCCT | CTCATCCTGG | ATTTATTCAT | TGCTGGAAGT | 120
| GATACATCTG | CCATAACAAC | AGAATGGGCA | ATGGCAGAAC | TACTTCGAAA | ACCTCAAGAA | 180
| TTTGTGAATG | CATGGGCAAT | TGGAAGAGAT | CCAAAATACT | GGGAAAAACC | ACTGGAGTTT | 240
| ATGCCTGAAA | GATTCTTGAA | GTGTAGTTTG | GATTACAAAG | GTAGGGTTTG | AGTATATACC | 300
| ATTTGGCGCA | GGTCGAAGAA | TTTGTCCTGG | AATGCCACAT | GCAATAAGG | ATGGTGAATT | 360
| TGATGCTGGC | TTCGATTATT | CACCATTTAG | TTGGGAATTA | CCTAAGGAAT | GGCACCAAAG | 420
| ATTTGAACAT | GGAGGAACAG | TTTGGAGTTA | CCTTGAGGAA | GGCTATTCCC | CTTATTGCCA | 480
| TTCCCAGTAT | GGAAGAAAAG | GTCATATTTT | AGCCCAAAAG | CTATGCATTT | TGTGTGTATG | 540
| TTT | | | | | | 543

( 2 ) INFORMATION FOR SEQ ID NO:26:

( i ) SEQUENCE CHARACTERISTICS:
        ( A ) LENGTH: 618 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

|  |  |  |  |  |  |
|---|---|---|---|---|---|
| AAACAGATCA | ATGCATTGCT | TGTGGAAATA | TTTGGAGCTG | GTACAGAATC | TACAACTGCT | 60
| ACAAGCCAAT | GGATGCTTGT | AGAACTCCTT | AGAAATCGAC | AAGCCTTGCC | CAAAGACACT | 120
| CAAGTTATGG | TAAACGAGTG | GGCGATTGCG | TATGATCCTA | AGATTTGGGG | CAGCTTCAAA | 180
| CCCGAAAGGT | TTATCGATTC | AAAAATAGAT | CCTTTGGACC | ACAAAGGGCA | AAATTTTGAA | 240
| TATTTTCCTT | TTGGTTCTGG | AAGGAGAATT | TGTGCTGGAG | AACCTTTGGC | TTCTAGGGTT | 300
| ATTCCCTTAG | CTGTTGCTTC | TATGATCCAT | AAGTTTGATA | TCACTATGTT | AGAAGATCCA | 360
| CTCTCATCAT | TCCTAAGTTG | AGAAGAGTGA | GGAAATTAAA | AGAAGCAGAA | GATATGTTAC | 420
| TATAAAAACT | CGTTATATAT | ATATATATTG | CTGTATCTAT | ATATGTGTGA | ATGATCTGCT | 480
| GCTCATGTTG | TGTTTTGTTG | TTTGTGTACT | ATAGGTCATA | CCTAAGTTGA | TGAAATGTCT | 540
| CTGAGAATAT | ATACTCCTTA | TATAATAGGA | GTAATTTACC | GATAATTAAT | ATTCCTGCGA | 600
| CAAAAAAAAA | AAAAAAA | | | | | 618

( 2 ) INFORMATION FOR SEQ ID NO:27:

( i ) SEQUENCE CHARACTERISTICS:
        ( A ) LENGTH: 203 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:27:

| | | | | | |
|---|---|---|---|---|---|
| CTCGAGAATC | AATGGAAGAT | GTAAGATTAC | TAGGCTATCA | CATACCTGCT | AAAACGAGAC | 60 |
| TCTTTATCAA | TGCTTGGACA | ATGGGGAGAG | ACCCACTAAC | ATGGGAAAAT | CCAGAAGAGT | 120 |
| ATCAGCCAGA | GAGATTCTTG | AATAGAGATA | CTGATGTCAA | AGGAGTAAAC | TTTGAGTTCA | 180 |
| TTCCCTTTGG | CGCCGGCAGA | AGC | | | | 203 |

(2) INFORMATION FOR SEQ ID NO:28:

(i) SEQUENCE CHARACTERISTICS:
(A) LENGTH: 1812 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:28:

| | | | | | | |
|---|---|---|---|---|---|---|
| CTTTCTACTA | GCTACTTCGT | TATATATATG | TAAAATTGTG | ACTTTGAAAA | TCATTTAAAT | 60 |
| TATCATAAGG | TTCATTTTAT | CTTGATCAAA | ATATTTACTT | CGGCCATATA | CGTTTTCCTT | 120 |
| TAGTCATGAT | GCTACTTACT | GAGCTTGGTG | CAGCAACTTC | AATCTTTCTA | ATAGCACACA | 180 |
| TAATCATTTC | AACTCTTATT | TCAAAAACTA | CCGGCCGGCA | TCTACCGCCG | GGGCCAAGAG | 240 |
| GGTGGCCGGT | GATCGGAGCA | CTTCCACTTT | TAGGAGCCAT | GCCACATGTT | TCCTTAGCTA | 300 |
| AAATGGCAAA | AAAATATGGA | GCAATCATGT | ATCTCAAAGT | TGGAACATGT | GGCATGGCAG | 360 |
| TTGCTTCTAC | CCCTGATGCT | GCTAAAGCAT | TCTTGAAAAC | ACTTGAGATC | AACTTCTCCA | 420 |
| ATCGTCCACC | TAATGCAGGT | GCCACTCACT | AGCTTATAAT | GCTCAAGACA | TGGTTTTTGC | 480 |
| ACATTATGGA | CCACGATGGA | AGTTGCTAAG | GAAATTAAGC | AACTTGCATA | TGCTAGGGGG | 540 |
| AAAAGCCTTA | GAGAATTGGG | CAAATGTTCG | TGCCAATGAG | CTAGGGCACA | TGCTAAAATC | 600 |
| AATGTCCGAT | ATGAGTCGAG | AGGGCCAGAG | GGTTGTGGTG | GCGGAGATGT | TGACATTTGC | 660 |
| CATGGCCAAT | ATGATCGGAC | AAGTGATGCT | AAGCAAAAGA | GTATTTGTAG | ATAAAGGTGT | 720 |
| TGAGGTAAAT | GAATTTAAGG | ACATGGTTGT | AGAGTTAATG | ACAATAGCAG | GGTATTTCAA | 780 |
| CATTGGTGAT | TTTATTCCTT | GTTAGCTTG | GATGGATTTA | CAAGGGATAG | AAAAACGAAT | 840 |
| GAAACGTTTA | CATAAGAAGT | TTGATGCTTT | ATTGACAAAG | ATGTTTGATG | AACACAAAGC | 900 |
| AACTACCTAT | GAACGTAAGG | GGAAACCAGA | TTTTCTTGAT | GTTGTTATGG | AAAATGGGGA | 960 |
| CAATTCTGAA | GGAGAAAGAC | TCAGTACAAC | CAACATCAAA | GCACTTTGC | TGAATTTGTT | 1020 |
| CACAGCTGGT | ACGGACACTT | CTTCTAGTGC | AATAGAATGG | GCACTTGCAG | AAATGATGAA | 1080 |
| GAACCCTGCC | ATTTTGAAAA | AAGCACAAGC | AGAAATGGAT | CAAGGTCATT | GGAAGAAATA | 1140 |
| GGCGTTTACT | CGAATCCGAT | ATCCCAAATC | TCCCTTACCT | CCGAGCAATT | TGCAAAGAAA | 1200 |
| CATTTCGAAA | ACACCCTTCT | ACACCATTAA | ATCTTCCTAG | GATCTCGAAC | GAACCATGCA | 1260 |
| TAGTCGATGG | TTATTACATA | CCAAAAAACA | CTAGGCTTAG | TGTTAACATA | TGGGCAATTG | 1320 |
| GAAGAGATCC | CCAAGTTTGG | GAAAATCCAC | TAGAGTTTAA | TCCCGAAAGA | TTCTTGAGTG | 1380 |
| GAAGAAACTC | CAAGATTGAT | CCTCGAGGGA | ACGATTTTGA | ATTGATACCA | TTTGGTGCTG | 1440 |
| GACGAAGAAT | TTGTGCAGGA | ACAAGAATGG | GAATTGTAAT | GGTGGAATAT | ATATTAGGAA | 1500 |
| CTTTGGTTCA | TTCATTTGAT | TGGAAATTAC | CAAGTGAAGT | TATTGAGTTG | AATATGGAAG | 1560 |

| | | | | | |
|---|---|---|---|---|---|
|AAGCTTTTGG|CTTAGCTTTG|CAGAAAGCTG|TCCCTCTTGA|AGCTATGGTT|ACTCCAAGGT 1620|
|TACAATTGGA|TGTTTATGTA|CCATAGCTAT|AGATGTGTAT|TGTGCTATAA|TTGCGCATGT 1680|
|TGTTGGTTGT|AGCATGAGAT|ATTAAAAGGA|GTACATGAAG|CGCATTGCAT|GAGTTTAACT 1740|
|TGTAGCTCCT|TAATATTTTA|GGTATTTTTC|AATTAATAAG|TTCTTGTTGG|TTGGGTAAAA 1800|
|AAAAAAAAAA|AA| | | |1812|

( 2 ) INFORMATION FOR SEQ ID NO:29:

( i ) SEQUENCE CHARACTERISTICS:
        ( A ) LENGTH: 1755 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

| | | | | | |
|---|---|---|---|---|---|
|TTGAATCCAG|CTCTATCTGG|CTTTAGACAA|TGGTGCTACT|TAGTGAGCTT|GCTGCAGCAA 60|
|CCTTAATCTT|TCTAACAACA|CATATCTTCA|TTTCAACTCT|TCTTTCTATA|ACTAACGGCC 120|
|GGCGTCTCCC|GCCAGGGCCA|AGAGGGTGGC|CGGTGATCGG|AGCACTTCCA|CTTTTAGGAG 180|
|CCATGCCACA|TGTTTCCTTA|GCTAAAATGG|CAAAAAATA|TGGAGCAATC|ATGTATCTCA 240|
|AAGTTGGAAC|GTGTGGCATG|GTAGTTGCTT|CTACCCCTGA|TGCTGCTAAA|GCGTTCTTGA 300|
|AAACACTTGA|TCTCAACTTC|TCCAATCGTC|CACCTAATGC|AGGTGCCACC|CACTTAGCCT 360|
|ATGGTGCTCA|AGACATGGTT|TTTGCACATT|ATGGACCAAG|ATGGAAGTTG|CTAAGGAAAT 420|
|TAAGCAACTT|ACATATGCTA|GGGGGAAAG|CCTTAGAAAA|TTGGGCAAAT|GTTCGTGCCA 480|
|ATGAGCTAGG|ACACATGCTA|AAATCGATGT|TGATATGAG|CAGAGAAGGG|GAGAGAGTTG 540|
|TGGTGGCGGA|GATGTTGACA|TTTGCCATGG|CGAATATGAT|CGGACAGGTG|ATACTTAGCA 600|
|AAAGAGTATT|TGTAAATAAA|GGTGTTGAGG|TAAATGAATT|TAAGGACATG|GTGGTAGAGT 660|
|TAATGACAAC|AGCAGGGTAT|TTTAACATTG|GTGATTTTAT|TCCTTGTTTA|GCTTGGATGG 720|
|ATTTACAAGG|GATAGAAAAA|GGAATGAAAC|GTTTACATAA|GAAGTTTGAT|GCTTTATTGA 780|
|CAAAGATGTT|TGATGAACAC|AAAGCAACTA|GCTATGAACG|TAAGGGGAAA|CCAGATTTTC 840|
|TTGATTGTGT|TATGGAAAAT|AGGGACAATT|CTGAAGGAGA|AAGGCTCAGT|ACAACCAACA 900|
|TCAAAGCACT|CTTGCTGAAT|TTGTTCACAG|CTGGTACAGA|CACTTCTTCT|AGTGCAATAG 960|
|AATGGGCACT|TGCAGAGATG|ATGAAGAACC|CTGCCATTTT|AAAGAAAGCA|CAAGGAGAAA 1020|
|TGGATCAAGT|CATTGGAAAC|AATAGGCGTC|TGCTCGAATC|GGATATCCCA|AATCTCCCTT 1080|
|ACCTCCGAGC|AATTTGCAAA|GAAACATTTC|GAAAGCACCC|TTCTACACCA|TTAAATCTCC 1140|
|CTAGGATCTC|GAACGAACCA|TGCATTGTCG|ATGGTTATTA|CATACCAAAA|AACACTAGGC 1200|
|TTAGTGTTAA|CATATGGGCA|ATTGGAAGAG|ATCCCGAAGT|TTGGGAGAAC|CCACTAGAGT 1260|
|TTTATCCTGA|AAGGTTCTTG|AGTGGAAGAA|ACTCGAAGAT|TGATCCTCGA|GGGAACGACT 1320|
|TTGAATTGAT|ACCATTTGGT|GCTGGACGAA|GAATTTGTGC|AGGGACAAGA|ATGGGAATCG 1380|
|TAATGGTGGA|ATATATATTA|GGAACTTTGG|TCCATTCATT|TGATTGGAAA|TTACCAAGTG 1440|
|AAGTTATTGA|GCTAAATATG|GAAGAAGCTT|TTGGATTAGC|TTTGCAGAAA|GCTGTCCCTC 1500|
|TTGAAGCTAT|GGTTACTCCA|AGGCTGCCTA|TTGATGTTTA|TGCACCTTTA|GCTTGAAACA 1560|
|TGCCTTTACG|TTGGTTTCAG|TTTTGGGTAG|TATAATGTTG|TGGTGTTTGG|CTATAGAAAT 1620|
|ATTAATAAAT|GCTAGTATCT|TGAAGGCGCG|TGCAGGGGA|GGGGGTTGTC|TTAGATAGTA 1680|

```
GTAATATGTT  AGCCTTCCTT  TTATTTCTTG  TGATTGTGAG  AATCTTGATA  TGTTTTCTTG    1740

AAAAAAAAAA  AAAAA                                                         1755
```

GENETIC SEQUENCES ENCODING FLAVONOID PATHWAY ENZYMES AND USES THEREFOR

This is a continuation of application Ser. No. 08/285,309, filed on Aug. 3, 1994, now U.S. Pat. No. 5,569,832 which is a continuation of Ser. No. 912,900, filed on Jul. 13, 1992, now U.S. Pat. No. 5,349,125.

The present invention relates generally to genetic sequences encoding flavonoid pathway metabolising enzymes and their use such as in the manipulation of pigmentation in plants and other organisms.

The flower industry strives to develop new and different varieties of flowering plants. An effective way to create such novel varieties is through the manipulation of flower colour and classical breeding techniques have been used with some success to produce a wide range of colours for most of the commercial varieties of flowers. This approach has been limited, however, by the constraints of a particular species' gene pool and for this reason it is rare for a single species to have a full spectrum of coloured varieties. Indeed, due to the limited availability of blue flowers, less than five percent of cutflowers sold through the auction system in Holland in 1988 were blue. Amongst the twelve top selling flowers, only iris and freesia offer blue coloured varieties and these varieties constitute less than four percent of all flower sales. The development of blue varieties of the major cutflower species, for example, rose, chrysanthemum, carnation and gerbera would offer a significant opportunity in both the cutflower and ornamental markets.

Flower colour is predominantly due to two types of pigment: flavonoids and carotenoids. Flavonoids contribute to a range of colours from yellow to red to blue. Carotenoids impart an orange or yellow tinge and are commonly the only pigment in yellow or orange flowers. The flavonoid molecules which make the major contribution to flower colour are the anthocyanins which are glycosylated derivatives of cyanidin, delphinidin, petunidin, peonidin, malvidin and pelargonidin, and are localised in the vacuole. The different anthocyanins can produce marked differences in colour. Flower colour is also influenced by co-pigmentation with colourless flavonoids, metal complexation, glycosylation, acylation, methylation and vacuolar pH (Forkmann, 1991).

The biosynthetic pathway for the flavonoid pigments (hereinafter referred to as the "flavonoid pathway") is well established and is shown in FIG. 1 (Ebel and Hahlbrock, 1988; Hahlbrock and Grisebach, 1979; Wiering and de Vlaming, 1984; Schram et al, 1984; Stafford, 1990). The first committed step in the pathway involves the condensation of three molecules of malonyl-CoA with one molecule of p-coumaroyl-CoA. This reaction is catalysed by the enzyme chalcone synthase (CHS). The product of this reaction, 2',4,4',6'-tetrahydroxychalcone, is normally rapidly isomerized to produce naringenin by the enzyme chalcone flavanone isomerase (CHI). Naringenin is subsequently hydroxylated at the 3 position of the central ring by flavanone 3-hydroxylase (F3H) to produce dihydrokaempferol (DHK).

The B-ring of dihydrokaempferol can be hydroxylated at either the 3', or both the 3' and 5' positions, to produce dihydroquercetin (DHQ) and dihydromyricetin (DHM), respectively. Two key enzymes involved in this pathway are flavonoid 3'-hydroxylase (hereinafter referred to as 3'-hydroxylase) and flavonoid 3',5'-hydroxylase (hereinafter referred to as 3',5'-hydroxylase). The 3'-hydroxylase acts on DHK to produce DHQ and on naringenin to produce eriodictyol. The 3',5'-hydroxylase is a broad spectrum enzyme catalyzing hydroxylation of naringenin and DHK in the 3' and 5' positions and of eriodictyol and DHQ in the 5' position (Stotz and Forkmann, 1982), in both instances producing pentahydroxyflavanone and DHM, respectively. The pattern of hydroxylation of the B-ring plays a key role in determining petal colour.

Flavonoid 3'-hydroxylation in microsomal extracts requires NADPH and $O_2$ as well as the aglycone of either naringenin or DHK. The parsley cell culture enzyme has been well studied (Hagmann et al, 1983). Inhibition by carbon monoxide, cytochrome c and $NADP^+$ indicated that the enzyme is a cytochrome P450-dependent enzyme. A similar enzyme activity has been demonstrated in maize (Larson and Bussard, 1986). The 3',5'-hydroxylase is also of the cytochrome P450 class of enzymes. Cytochrome P450 enzymes are widespread in nature and have been characterised in vertebrates, insects, yeasts, fungi, bacteria and one plant. Sequences of at least 154 cytochrome P450 genes have been determined and the genes grouped into 27 different gene families (Nebert et al, 1991). Within a single family, the P450 protein sequences are generally >40% identical whilst sequences within the same subfamily are >46% identical (Nebert et al, 1991). Information on plant cytochromes P450 is limited.

The ability to control in plants 3' or 3',5'-hydroxylase activity, or other enzymes involved in the flavonoid pathway, would provide a means to manipulate petal colour thereby enabling a single species to express a broader spectrum of flower colours. In accordance with the present invention, the genetic sequences encoding flavonoid pathway enzymes such as 3',5'-hydroxylase have been identified and cloned. These recombinant sequences permit the modulation of DHK metabolism as well as the metabolism of other substrates such as DHQ, naringenin and eriodictyol, thereby determining the hydroxylation pattern of the anthocyanins and providing a means to manipulate petal colour. The present invention, however, extends beyond flowers to fruit and vegetable plants and to leaves of, for example, ornamental plants.

Accordingly, one aspect of the present invention provides a nucleic acid isolate comprising a sequence of nucleotides encoding, or complementary to a sequence encoding, a dihydrokaempferol (DHK) hydroxylating enzyme, or a derivative or part thereof.

For convenience and by way of shorthand notation only, reference herein to "DHK hydroxylating enzyme" includes flavonoid pathway hydroxylating enzymes acting on one or more of the following: DHK, DHQ, naringenin, eriodictyol.

Preferably, the DHK hydroxylating enzyme is 3',5'-hydroxylase. However, the methods employed to clone the genetic sequences encoding this enzyme could be employed to isolate other genetic sequences encoding enzymes such as the 3'-hydroxylase. Accordingly, reference herein to the isolation and cloning of 3',5'-hydroxylase should be taken to include reference to other flavonoid hydroxylating enzymes such as 3'-hydroxylase.

By the term "nucleic acid isolate" is meant a genetic sequence in a non-naturally occurring condition. Generally, this means isolated away from its natural state or formed by procedures not necessarily encountered in its natural environment. More specifically, it includes nucleic acid molecules formed or maintained in vitro, recombinant or synthetic molecules and nucleic acids in combination with heterologous nucleic acids. It also extends to naturally occurring sequences following at least a partial purification relative to other nucleic acid sequences.

By "genetic sequences" as used herein is meant any contiguous series of nucleotide bases specifying directly, or via a complementary series of bases, a sequence of amino acids in a DHK hydroxylating enzyme, for example, 3',5'-hydroxylase. The nucleic acid or its complementary form may encode the full length enzyme or a derivative or part thereof. By "derivative" is meant any single or multiple amino acid substitutions, deletions, and/or additions relative to the naturally occurring enzyme. In this regard, the nucleic acid includes the naturally occurring nucleotide sequence encoding 3',5'-hydroxylase or may contain single or multiple nucleotide substitutions, deletions and/or additions to said naturally occurring sequence. The nucleic acid sequences contemplated herein also encompass oligonucleotides useful as genetic probes or as "anti-sense" molecules capable of regulating expression of the corresponding gene in a plant. Accordingly, when the nucleic acid or its complementary form encodes a "part" of the 3',5'-hydroxylase, then such a nucleic acid molecule may be useful as an oligonucleotide probe, primer for polymerase chain reactions or in various mutagenic techniques.

Amino acid insertional derivatives of the DHK hydroxylating enzyme and in particular the 3',5'-hydroxylase of the present invention include amino and/or carboxyl terminal fusions as well as intra-sequence insertions of single or multiple amino acids. Insertional amino acid sequence variants are those in which one or more amino acid residues are introduced into a predetermined site in the protein although random insertion is also possible with suitable screening of the resulting product. Deletional variants are characterised by the removal of one or more amino acids from the sequence. Substitutional amino acid variants are those in which at least one residue in the sequence has been removed and a different residue inserted in its place. Typical substitutions are those made in accordance with the following Table 1:

TABLE 1

Suitable residues for amino acid substitutions

| Original Residue | Exemplary Substitutions |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Where the 3',5'-hydroxylase is derivatised by amino acid substitution, the amino acids are generally replaced by other amino acids having like properties, such as hydrophobicity, hydrophilicity, electronegativity, bulky side chains and the like. Amino acid substitutions are typically of single residues. Amino acid insertions will usually be in the order of about 1–10 amino acid residues and deletions will range from about 1–20 residues. Preferably, deletions or insertions are made in adjacent pairs, i.e. a deletion of two residues or insertion of two residues.

The amino acid variants referred to above may readily be made using peptide synthetic techniques well known in the art, such as solid phase peptide synthesis (Merrifield, 1964) and the like, or by recombinant DNA manipulations. Techniques for making substitution mutations at predetermined sites in DNA having known or partially known sequence are well known and include, for example, M13 mutagenesis. The manipulation of DNA sequence to produce variant proteins which manifest as substitutional, insertional or deletional variants are conveniently described, for example, in Sambrook et al., (1989).

Other examples of recombinant or synthetic mutants and derivatives of the 3',5'-hydroxylase of the present invention include single or multiple substitutions, deletions and/or additions of any molecule associated with the enzyme such as carbohydrates, lipids and/or proteins or polypeptides.

The terms "analogues" and "derivatives" also extend to any functional chemical equivalent of the 3',5"-hydroxylase and also to any amino acid derivative described above.

The nucleic acids of the present invention may be ribonucleic acids or deoxyribonucleic acids, single or double stranded and linear or covalently closed circular molecules. Preferably, the nucleic acid molecule is cDNA. The present invention also extends to other nucleic acid molecules which hybridise under low, preferably under medium and most preferably under high stringency conditions with the nucleic acid molecules contemplated by the present invention. Expressed in alternative terms, the present invention extends to a nucleic acid molecule having a nucleotide sequence set forth in FIG. 9 or 10 or to a molecule having at least 35%, more preferably at least 45%, even more preferably at least 55%, still more preferably at least 65–70%, and yet even more preferably greater than 85% similarity at the level of nucleotide or amino acid sequence and wherein the nucleic acid encodes or is complementary to a sequence which encodes an enzyme having 3',5'-hydroxylase activity. It should be noted, however, that nucleotide or amino acid sequences may have similarities below the above given percentages and yet still encode DHK hydroxylating enzymes and such molecules may still be considered in the scope of the present invention where they have conserved regions of homology. The present invention further extends to nucleic acid molecules in the form of oligonucleotide primers capable of hybridising to a portion of the nucleic acid molecules contemplated above under low, preferably under medium and most preferably under high stringency conditions.

The nucleic acid molecules contemplated herein may exist alone or in combination with a vector molecule and preferably an expression-vector. Such vector molecules replicate and/or express in eukaryotic and/or prokaryotic cells. Preferably, the vector molecules or parts thereof are capable of integration into the plant genome. The nucleic acid molecule may additionally contain a promoter sequence capable of directing expression of the nucleic acid molecule in a plant cell. The nucleic acid molecule and promoter may be introduced into the cell by any number of means such as by electroporation or Agrobacterium mediated transfer.

The present invention is exemplified using nucleic acid sequences derived from petunia since this represents the most convenient and preferred source of material to date. However, one skilled in the art will immediately appreciate that similar sequences can be isolated from any number of sources such as other plants or certain microorganisms. The genetics of the 3'-hydroxylases is known in flowers of Antirrhinum, Verbena and Petunia and in seedlings and aleurone layers of seeds of maize (Heller and Forkmann, 1988). The gene eos controls 3'-hydroxylase in Antirrhinum (Forkmann and Stotz, 1981), while the Ht1 and Pr genes control similar enzymes in Petunia (Stotz et al, 1985) and in maize aleurone layer, respectively (Larson and Bussard, 1986). Chemogenetic studies of *Verbena hybrida,* for example, have shown that in this plant the hydroxylation of the B-ring of anthocyanins in both the 3' and 5' position is controlled by one gene (Beale, 1940). Enzyme activity for 3',5'-hydroxylation is only present in flower extracts of delphinidin-producing strains (Stotz and Forkmann, 1982). NADPH-dependent microsomal enzyme activity for hydroxylation in the 3' and 5' position was also demonstrated in flower extracts of Callistephus and Lathyrus (Forkmann, 1991). As in *V. hybrida,* enzyme activity for the 3',5'-hydroxylation of flavanones and dihydroflavonols was only found to be present in flower extracts of those strains which contain 3',4',5'-hydroxylated flavonoid compounds (or methylated derivatives of them) in the flowers. Thus, formation of the 3',4',5'-hydroxylated flavonoids is clearly dependent on flavonoid 3',5'-hydroxylase activity.

The genes encoding 3',5'-hydroxylase have been identified in a number of ornamental plants including Callistephus (R), Petunia (Hf1, Hf2) and Verbena (P) by the presence of the respective mutants unable to produce delphinidin. Moreover, the respective enzyme activities have been demonstrated (Forkmann, 1991). The 3',5'-hydroxylase was also considered to be a microsomal cytochrome P450 enzyme (Heller and Forkmann, 1988). However, there are no published reports of the cloning of a 3',5'-hydroxylase gene from these or other plant species.

Other plant species capable of producing 3',4',5'-hydroxylated flavonoids or their derivatives include hydrangea (Takeda et al, 1985), delphinium (Asen et al, 1975), lisianthus (Asen et al, 1986), tomato (von Wettstein-Knowles, 1968) and potato (Harborne and Simmonds, 1962). These species, or other plants capable of producing 3',4',5'-hydroxylated flavonoids, would also be suitable sources for the isolation of a 3',5'-hydroxylase gene. All such nucleic acid sequences encoding directly or indirectly a flavonoid pathway enzyme (e.g. 3',5'-hydroxylase) are encompassed by the present invention regardless of their source.

Likewise, the gene cloning strategy outlined here may be used to isolate a 3',5'-hydroxylase gene from other plants which produce 3',4',5'-hydroxylated flavonoids. Clones and oligonucleotides herein disclosed may be used to detect, isolate and clone similar genetic sequences using the same technology as herein described, although some minor modification(s) to the experimental procedures may be required. All such minor variations are encompassed by the present invention. Examples of other suitable sources of enzymes such as 3',5'-hydroxylase include, but are not limited to, verbena, delphinium, grape, iris, freesia, hydrangea, cyclamen, potato, pansy and eggplant.

In accordance with the present invention, a nucleic acid sequence encoding a DHK hydroxylating enzyme such as 3',5'-hydroxylase may be introduced into and expressed in a transgenic plant thereby providing a means to convert DHK and/or other suitable substrates, if synthesized in the plant cell, ultimately into anthocyanin derivatives of anthocyanidins such as delphinidin, petunidin or malvidin. The production of these anthocyanins contributes to the production of a variety of shades of blue colour or blue-like colour. Expression of the nucleic acid sequence in the plant may be constitutive, inducible or developmental.

Accordingly, another aspect of the present invention provides a method for producing a transgenic plant capable of expressing a recombinant DHK hydroxylating enzyme or active mutants or derivatives thereof, said method comprising introducing into a cell of a suitable plant a nucleic acid molecule which comprises a sequence of nucleotides encoding said DHK hydroxylating enzyme, under conditions permitting the eventual expression of said nucleic acid molecule, regenerating a transgenic plant from the cell and growing said transgenic plant for a time and under conditions sufficient to permit the expression of the nucleic acid.

In a preferred embodiment, the present invention contemplates a method for producing a transgenic flowering plant exhibiting altered inflorescence properties, said method comprising introducing into a cell of a suitable plant the nucleic acid sequence of the present invention under conditions permitting the eventual expression of said nucleic acid sequence, regenerating a transgenic plant from the cell and growing said transgenic plant for a time and under conditions sufficient to permit the expression of the nucleic acid sequence into the DHK hydroxylating enzyme.

Preferably, the DHK hydroxylating enzyme is 3',5'-hydroxylase, is developmentally regulated and the altered inflorescence includes the production of blue or red flowers or other colour shades depending on the physiological conditions of the recipient plant. By "suitable plant" is meant a plant capable of producing a substrate for the 3',5'-hydroxylase enzyme, and possessing the appropriate physiological properties and genotype required for the development of the colour desired. This may include but is not limited to rose, petunia, carnation, chrysanthemum and gerbera. In certain plant species it may be preferable to select a "high pH line", such being defined as a variety having a higher than average petal vacuolar pH. The origin of the recombinant 3',5'-hydroxylase or its mutants and derivatives are as hereinbefore described and include enzymes of petunia, verbena, delphinium, grape, iris, freesia, hydrangea, cyclamen, potato, pansy or eggplant origin.

One skilled in the art will immediately recognise the variations applicable to this method such as increasing or decreasing the expression of the enzyme naturally present in a target plant. This would lead to differing shades of colours such as different shades of blue or red.

In order to decrease activity of a target enzyme, such as 3',5'-hydroxylase, the nucleic acid sequence encoding this enzyme or various parts thereof could be used in the antisense orientation. Although not wishing to limit the present invention to any one theory, it is probable that such an antisense nucleic acid sequence would form a duplex with all or part of the naturally occurring mRNA specified for the enzyme thus preventing translation of the mRNA into active enzyme. Alternatively, ribozymes could be used to inactivate target nucleic acid sequences.

Accordingly, the present invention extends to a method for producing a transgenic plant capable of expressing a recombinant dihydrokaempferol (DHK) hydroxylating enzyme or which directs transcription of a nucleic acid sequence which is substantially complementary to all or a part of a mRNA molecule translatable to DHK hydroxylating enzyme, said method comprising introducing into a cell of a suitable plant the nucleic acid isolate according to claim 1 or 6 under conditions permitting the eventual expression of said nucleic acid isolate, regenerating a transgenic plant from the cell and growing said transgenic plant for a time and under conditions sufficient to permit the expression of the nucleic acid isolate. In this embodiment, suitable recipient plants extend to inter alia, iris, tulip, lily, lisianthus, freesia, delphinium, limonium and pelargonium.

The above methods of producing transgenic plants, therefore, extend to the alternative of introducing a gene or DNA fragment encoding an antisense mRNA or oligonucleotide to all or a portion or region of a sequence of nucleotides encoding, or complementary to a sequence encoding, a 3',5'-hydroxylase.

Consequently, the present invention extends to all transgenic plants containing all or part of the nucleic acid sequence of the present invention, or antisense forms thereof and/or any homologues or related forms thereof and in particular those transgenic plants which exhibit altered inflorescence properties. The transgenic plants, therefore, contain a stably introduced nucleic acid molecule comprising a nucleotide sequence encoding or complementary to a sequence encoding a DHK hydroxylating enzyme and in particular high pH plant lines carrying such introduced nucleic acid molecules as referred to above. The invention also extends to seeds from such transgenic plants. Such seeds, especially if coloured, will be useful as proprietary tags for plants.

A further aspect of the present invention is directed to recombinant forms of the DHK hydroxylating enzymes and in particular recombinant 3',5'-hydroxylase. The recombinant forms of the enzymes will provide a source of material for research to develop, for example, more active enzymes and may be useful in developing in vitro systems for production of coloured compounds.

Another aspect of the present invention contemplates a method for cloning a nucleic acid molecule comprising a sequence of nucleotides which encode or are complementary to a sequence which encode, a cytochrome P450 molecule or like molecule from a plant, said method comprising amplification of cytochrome P450 nucleotide sequences or complementary sequences from a suitable preparation of nucleic acid molecules from cells of said plant by polymerase chain reactions using one or more oligonucleotide primers, said primers having a nucleotide sequence derived from one or more consensus sequences of known microsomal cytochrome P450 molecules.

In a related embodiment, the method for cloning the cytochrome P450 nucleic acid molecules or their complementary sequences comprises selecting from a suitable cDNA library a clone capable of hybridising to one or more oligonucleotide primers corresponding to one or more consensus sequences or known cytochrome P450 molecules.

Preferably, one of the consensus sequences is from the haem-binding domain of cytochrome P450 molecules and is more preferably F(G,S) XGXRXCXG (SEQ ID NO:1) (wherein X is any amino acid) or is PGFAGRRICPG (SEQ ID NO:2). In a most preferred embodiment, the nucleotide sequences to be cloned encode or are complementary to sequences which encode, a DHK hydroxylating enzyme, and in particular 3',5'-hydroxylase. Even more preferably, the 3',5'-hydroxylase is as hereinbefore described and, more particularly, has an amino acid sequence or is encoded for by a sequence of nucleotides substantially as set forth in FIGS. 9 or 10 or has similarity thereto as defined above.

The present invention is further described by reference to the following non-limiting Figures and Example.

FIGS. 1(A) and (B) are schematic representations of the biosynthesis pathway for the flavonoid pigments. Enzymes involved in the first part of the pathway have been indicated as follows: PAL=Phenylalanine ammonia-lyase; C4H= Cinnamate 4-hydroxylase; 4CL=4-coumarate: CoA ligase; CHS=Chalcone synthase; CHI=Chalcone flavanone isomerase; F3H=Flavanone 3-hydroxylase; DFR= Dihydroflavonol-4-reductase; UFGT=UDP-glucose: flavonoid-3-O-glucosyltransferase. The later steps correspond to conversions that occur in P. hybrida flowers and include: 1=addition of a rhamnose sugar to the glucosyl residue of cyanidin-3-glucoside and delphinidin-3-glucoside; 2=acylation and 5-O-glucosylation; 3=3' methylation; 4=5' methylation; 5=3'5' methylation.

Figure 2A:
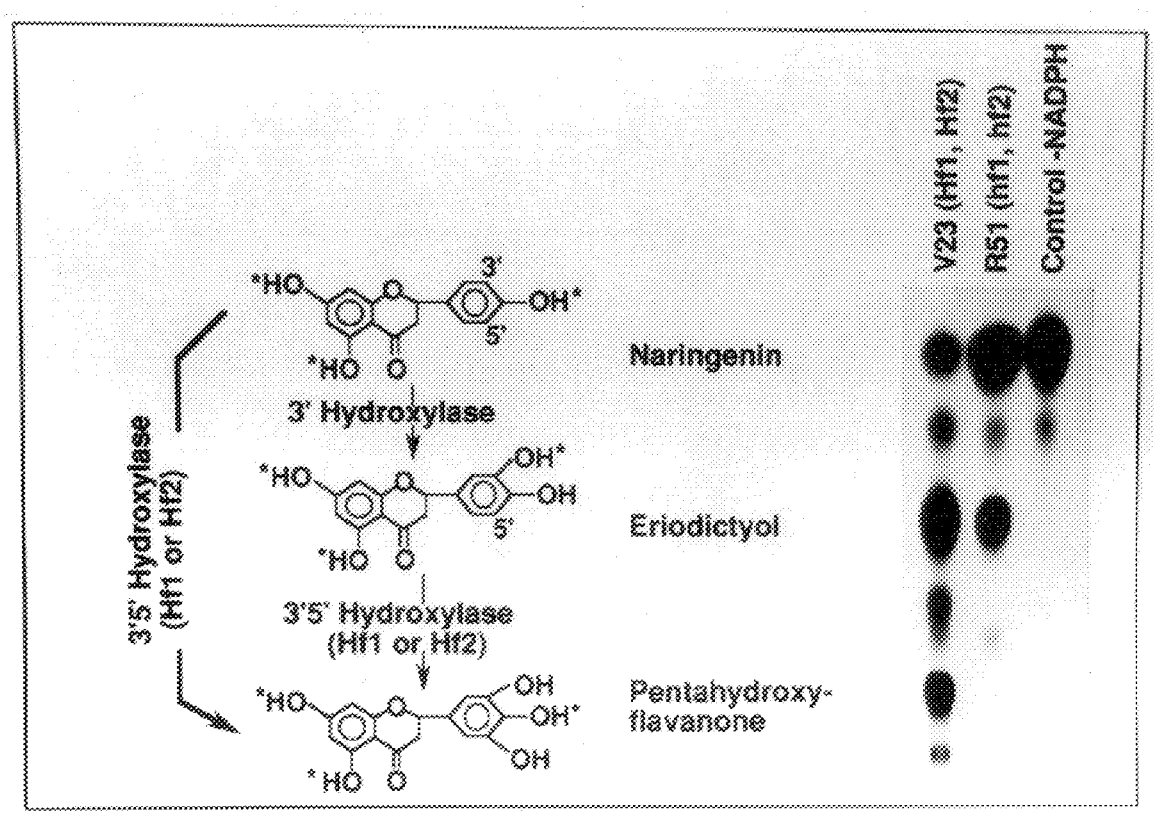

FIG. 2(A) shows 3',5'-hydroxylase activity in petal extracts of P. hybrida cv V23 (Hf1/Hf1, Hf2/Hf2) and the lack of 3',5'-hydroxylase activity in P. hybrida cv R51 (hf1/hf1, hf2/hf2). 3',5'-hydroxylase activity was detected by conversion of $^3$H-naringenin to the 3'- and 3',5'-hydroxylated derivatives eriodictyol and pentahydroxyflavanone. On the left-hand side of the figure the biochemical structures of the substrate, naringenin and the product of the 3'-hydroxylase reaction, eriodictyol and the 3',5'-hydroxylase reaction, pentahydroxyflavanone are shown. The location of the substrate and the hydroxylated products on the TLC plate is indicated on the right-hand side of the Figure which shows from left to right the autoradiographs of the reaction products produced by petal extracts of flowers from P. hybrida cv V23 and P. hybrida cv R51 and the control showing no hydroxylation of naringenin when NADPH is omitted from the reaction mixture.

Figure 2B:
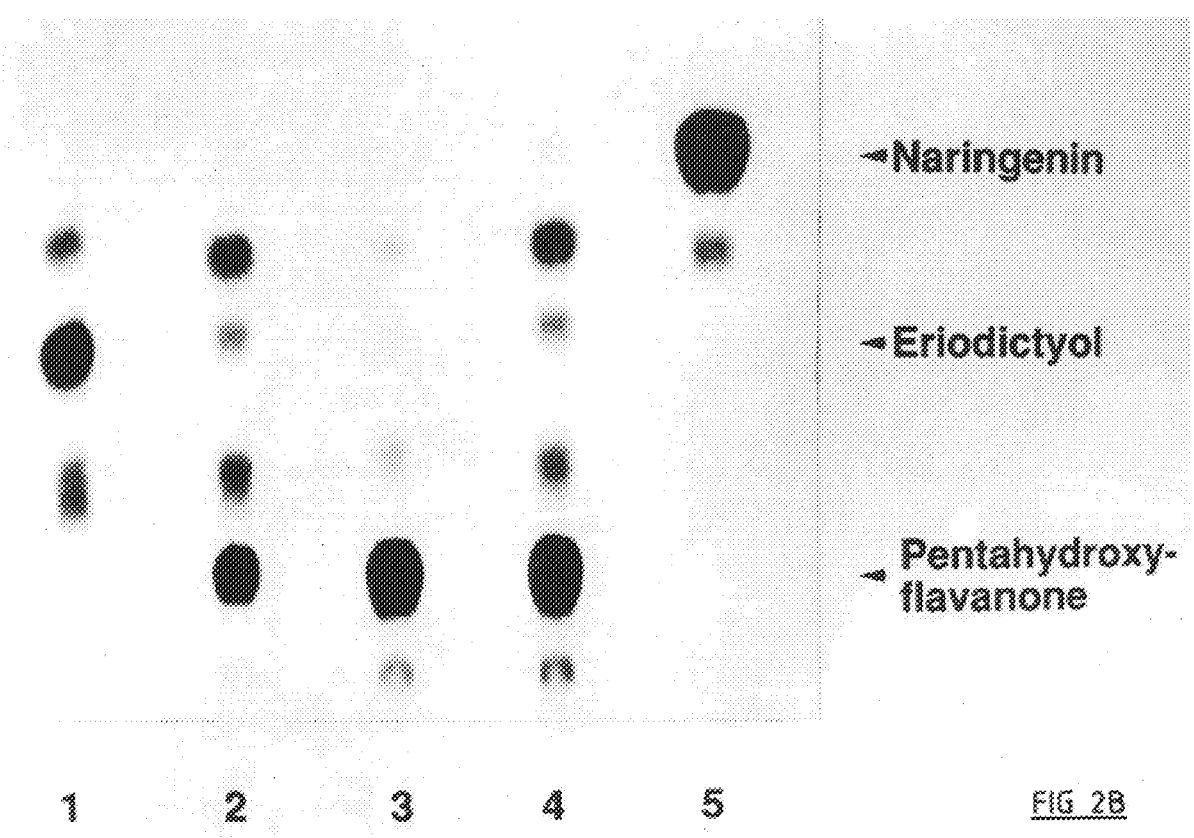

FIG. 2(B) shows 3',5'-hydroxylase activity in petal extracts of P. hybrida cv Old Glory Blue (OGB) flowers at different developmental stages. From left to right the autoradiographs of the TLC plates show (1) Stage 1 flowers [Unpigmented, closed bud (<25 mm in length)]: limited conversion of naringenin to the 3',5'-hydroxylated derivative pentahydroxyflavanone, (2) Stage 2 flowers [Pigmented, closed bud (25–35 mm in length)]: increased conversion to pentahydroxyflavanone indicative of higher 3',5'-hydroxylase levels, (3) Stage 3 flowers: [Dark purple bud with emerging corolla (>35 mm in length)]: maximal 3'5'-hydroxylase activity, (4) Stage 4 flowers [Dark purple opened flower pre-anther dehiscence (>50 mm in length)]: maximal 3',5'-hydroxylase activity (5) Stage 5 flowers [Fully opened flower with all anthers dehisced]: no detectable 3',5'-hydroxylase levels.

Figure 3A:
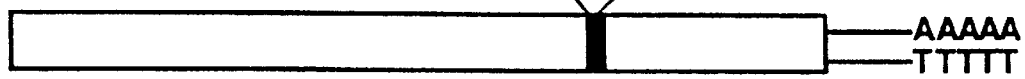

FIG. 3(A) is a schematic representation of a mRNA molecule encoding a cytochrome P450. The shaded region indicates the relative position of sequences encoding the haem binding domain. A consensus amino acid sequence for the most conserved region of this domain has been shown using single letter code. Amino acids that are present in 100% of cytochrome P450 sequences present in the SWISS-PROT database have been boxed and X indicates positions where there is a low level of sequence conservation.

Figure 3B:
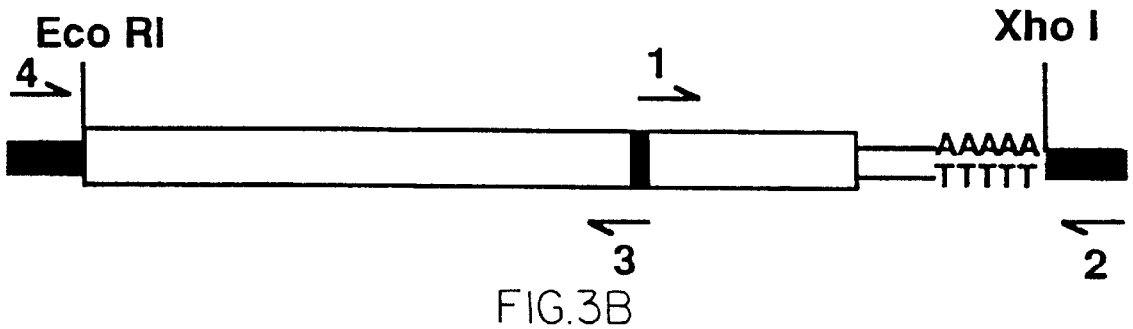

FIG. 3(B) shows the position of oligos used for PCR amplification of cytochrome P450 molecules pCGP450 and pCGP454 from cDNA library #1. Oligos 1 and 3 covered sequences in the conserved haem binding domain while oligos 2 and 4 corresponded to the pBluescript (Stratagene) −20 and reverse primer sequences, respectively. Oligos 1 and 2 were used to synthesize the cDNA insert in pCGP450; oligos 3 and 4 were used the synthesize the cDNA insert in pCGP454. Representation of a generalized cDNA molecule is identical to that shown in FIG. 3A; vector sequences have been indicated by light shading.

Figure 4A:
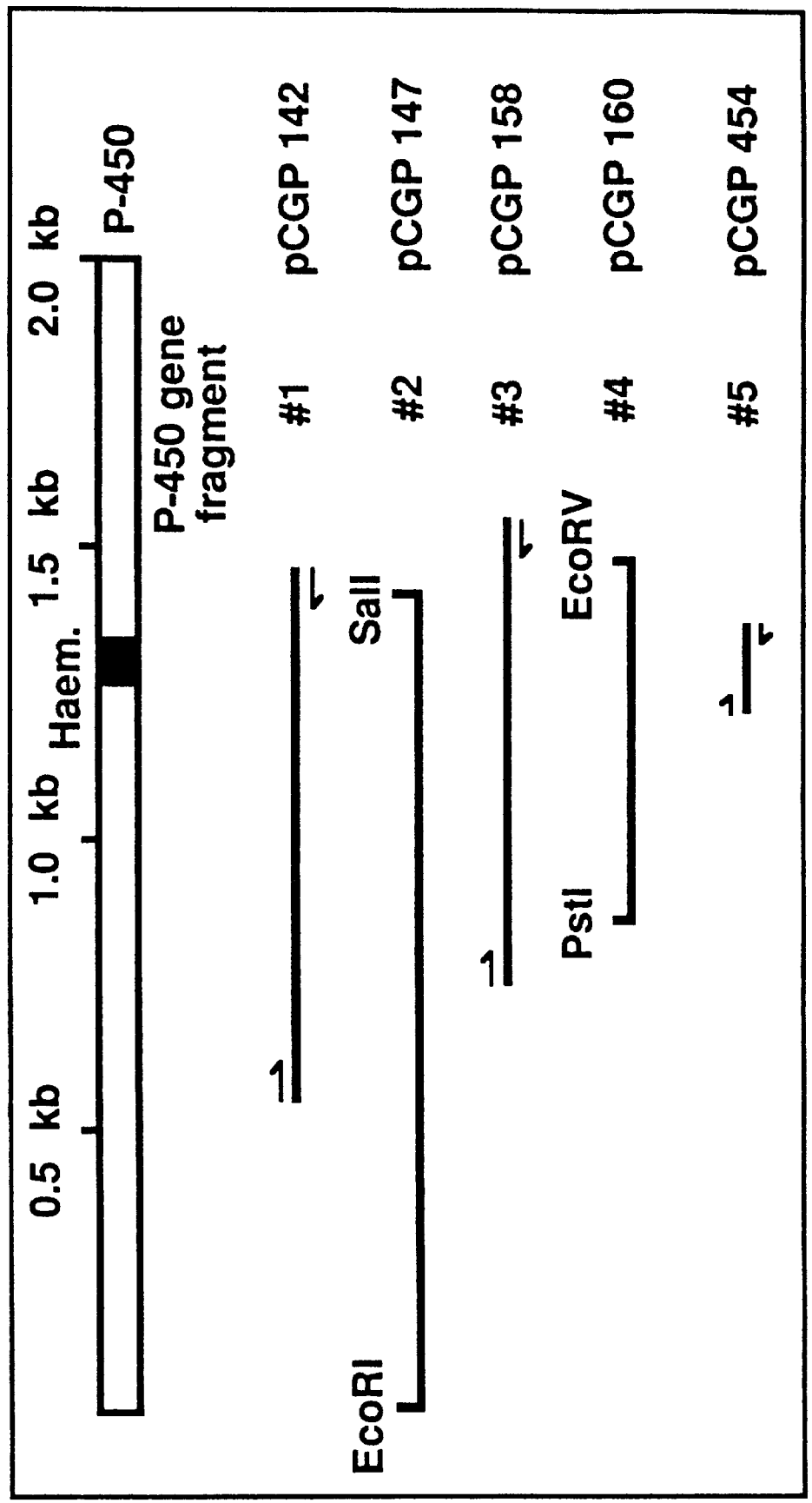
Figures 4C, 4D, 4E:
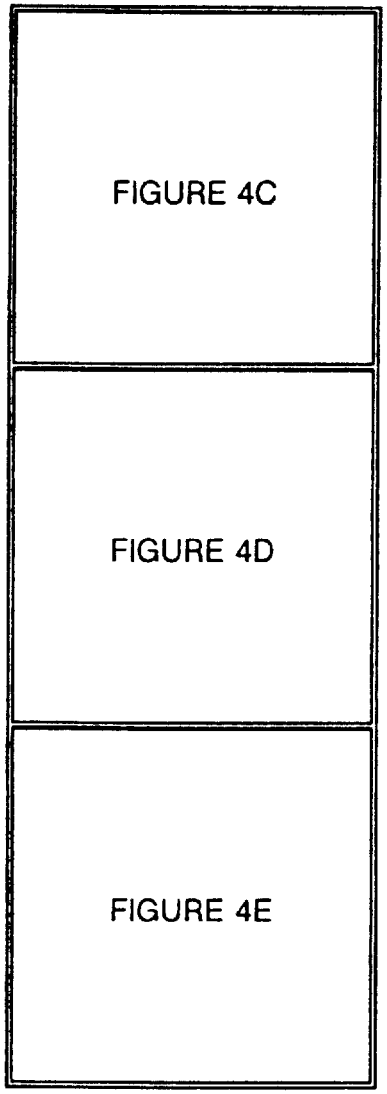

FIG. 4(A) is a schematic representation of DNA fragments used to probe cDNA library #1 to identify cytochrome P450 homologues, including pCGP174 and pCGP175. P450: generalized cytochrome P450 cDNA clone with the haem-binding domain (Haem) indicated by the shaded box; Fragment 1: a 900 bp fragment was obtained by PCR with oligos 5 and 6 using pCGP142 DNA as template; Fragment 2: a 1.3 kb fragment was isolated from a SAlI-EcoRI digest of pCGP147; Fragment 3: a 750 bp fragment was obtained by PCR with oligos 4 and 7 using pCGP158 DNA as template; Fragment 4: a 670 bp fragment was isolated from a PstI-EcoRV digest of pCGP160; Fragment 5: a 150 bp fragment was obtained by PCR with oligos 3 and 4 using pCGP454 DNA as template. All purified fragments were labelled with $^{32}$P-dCTP as described in the Materials and Methods.

FIGS. 4(B) to (H) show partial nucleotide sequences and the corresponding predicted amino acid translation products for the cDNA inserts from (i) pCGP142 SEQ ID NO:23, (ii) pCGP147 SEQ ID NO:24, (iii) pCGP158 SEQ ID NO:25, (iv) pCGP160 SEQ ID NO:26 and (v) pCGP454 SEQ ID NO:27. The regions used to probe cDNA library #1 to isolate pCGP174 and pCGP175 have been delineated by arrowheads.

Figure 5A:
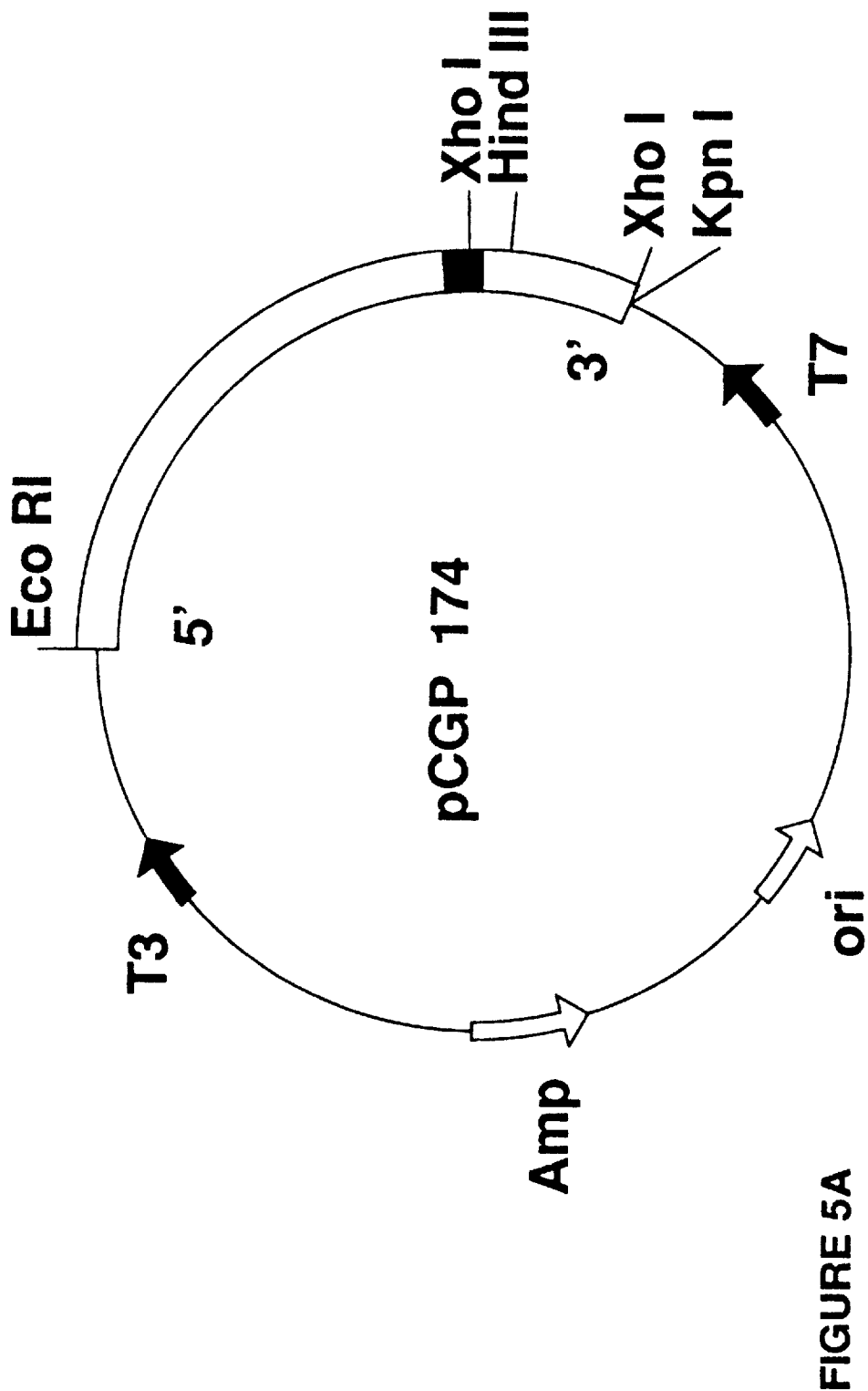

FIGS. 5(A) and (B) are diagrammatic representations of plasmids pCGP174 and pCGP175, respectively. The cDNA inserts are indicated as open boxes with the region encoding the putative haem-binding domain shown as a shaded region. An EcoRI site is at the 5'-end and a XhoI site is at the 3'-end of both cDNA inserts.

Figure 6A:
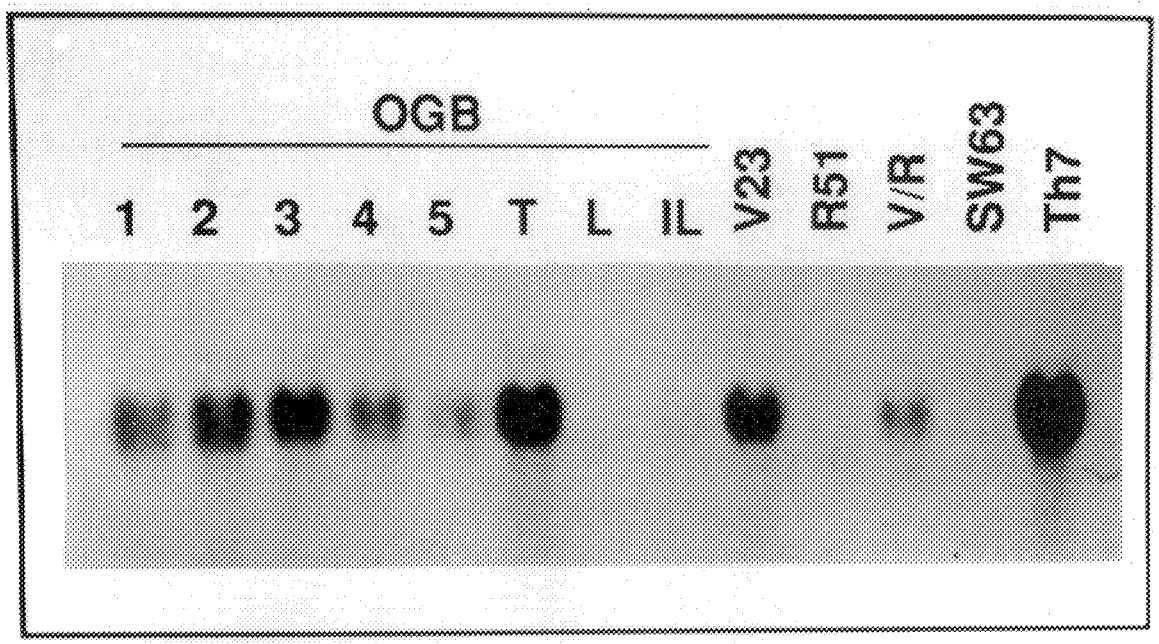

FIG. 6(A) is an autoradiograph of an RNA blot probed with the 3' region of the pCGP174 cDNA insert. Each lane contained a 20 μg sample of total RNA isolated from the following petunia tissues—1–5: OGB limb tissue of flowers at the five (1–5) different stages of flower development described in the Materials and Methods; T: OGB tube tissue from stage 3–4 flowers; L: leaf tissue from 6 week old OGB seedlings; IL: glucose/high light treated leaf tissue from 6 week old OGB seedlings; V23: V23 limb tissue from stage 3–4 flowers; R51: R51 corolla tissue from stage 3–4 flowers; VR: petal limb tissue from stage 3–4 flowers of the V23× R51 F$_1$ hybrid; Sw63: petal limb tissue from stage 3–4 flowers of Sw63; Th7: petal limb tissue from stage 3–4 flowers of Th7.

Figure 6B:
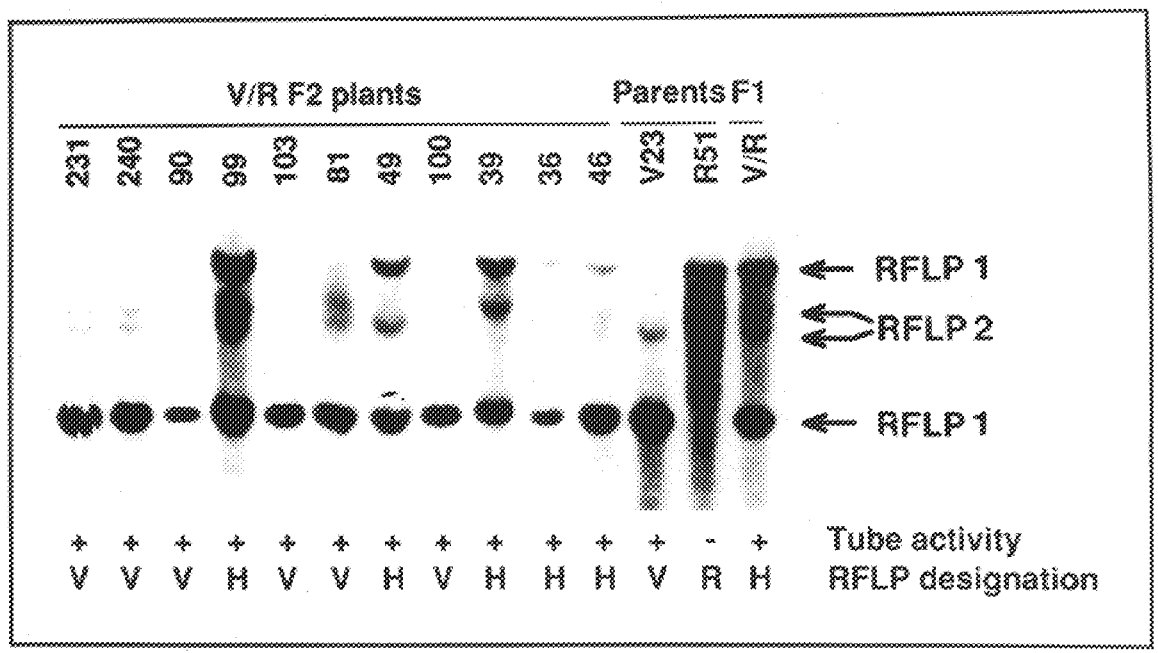

FIG. 6(B) is a representative autoradiograph from the RFLP analysis of the V23×R51 (V/R) F$_2$ plants. XbaI digested genomic DNA was probed with the 3' region of pCGP174. The V23 fragment that hybridized strongly to the probe was detected in all F$_2$ plants that had 3',5'-hydroxylase activity in tube tissue of the flowers (+). RFLP designation for the strongly hybridizing bands (RFLP#1) has been indicated for the various plants. V: V23-like RFLP, R: R51-like RFLP, H: heterozygotic (VR).

Figure 7A:
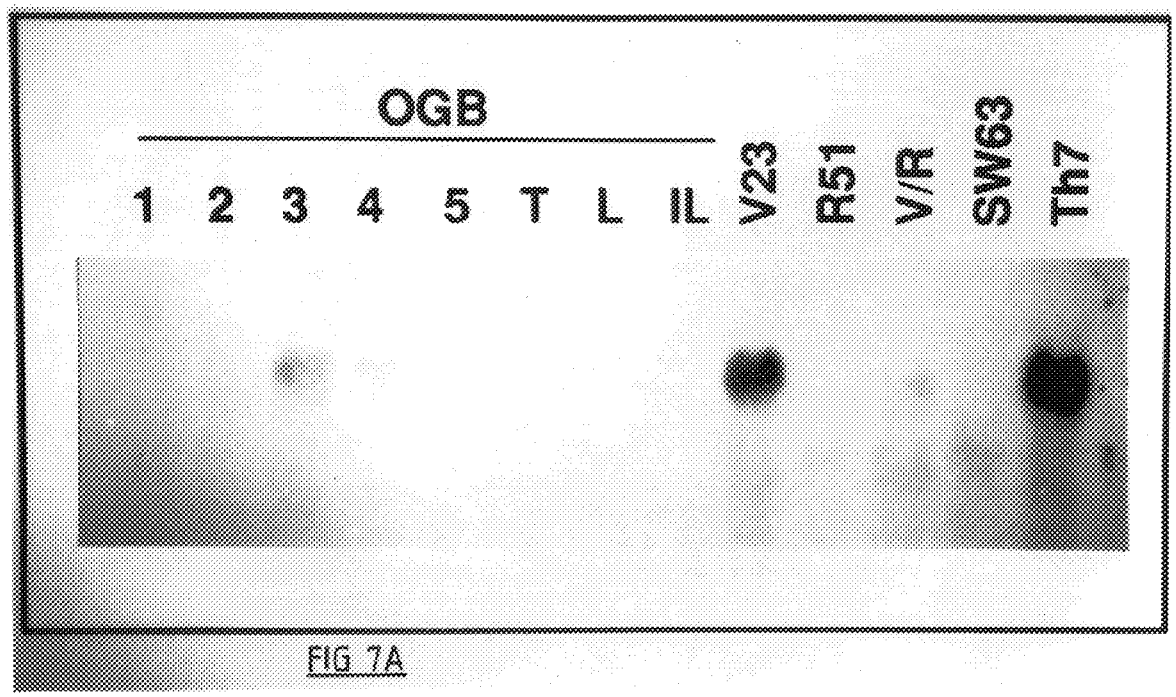

FIG. 7(A) is an autoradiograph of a RNA blot probed with the 3' region of the pCGP175 cDNA insert. Each lane contained a 20 μg sample of total RNA isolated from the following—1–5: OGB limb tissue of flowers at the five (1–5) different stages of flower development described in the Materials and Methods; T: OGB tube tissue from stage 3–4 flowers; L: leaf tissue from 6 week old OGB seedlings; IL: glucose/high light treated leaf tissue from 6 week old OGB seedlings; V23: V23 limb tissue from stage 3–4 flowers; R51: R51 corolla tissue from stage 3–4 flowers; VR: petal limb tissue from stage 3–4 flowers of the V23×R51 F$_1$ hybrid; Sw63: petal limb tissue from stage 3–4 flowers of Sw63; Th7: petal limb tissue from stage 3–4 flowers of Th7.

Figure 7B:
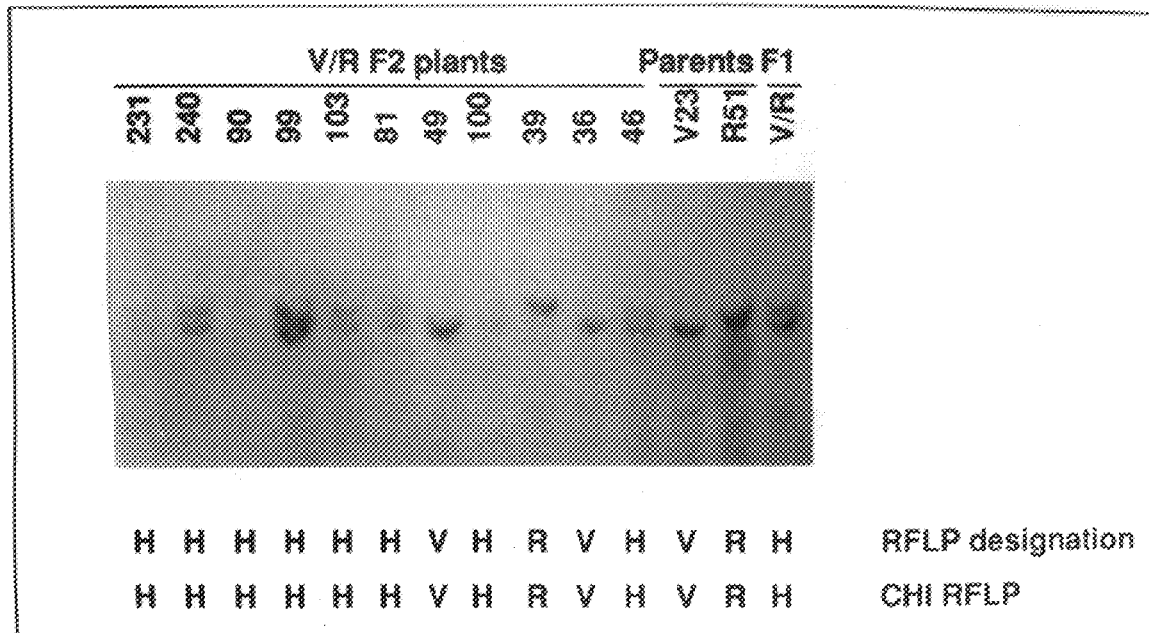

FIG. 7(B) is a representative autoradiograph from the RFLP analysis of the V23×R51 (V/R) F$_2$ plants. XbaI digested genomic DNA was probed with the 3' region of pCGP175. The RFLP designation obtained using the pCGP175 probe was identical to the po designation assigned using the chi-A probe. V: V23-like RFLP; R: R51-like RFLP; H: heterozygotic (VR) RFLP.

Figure 8:
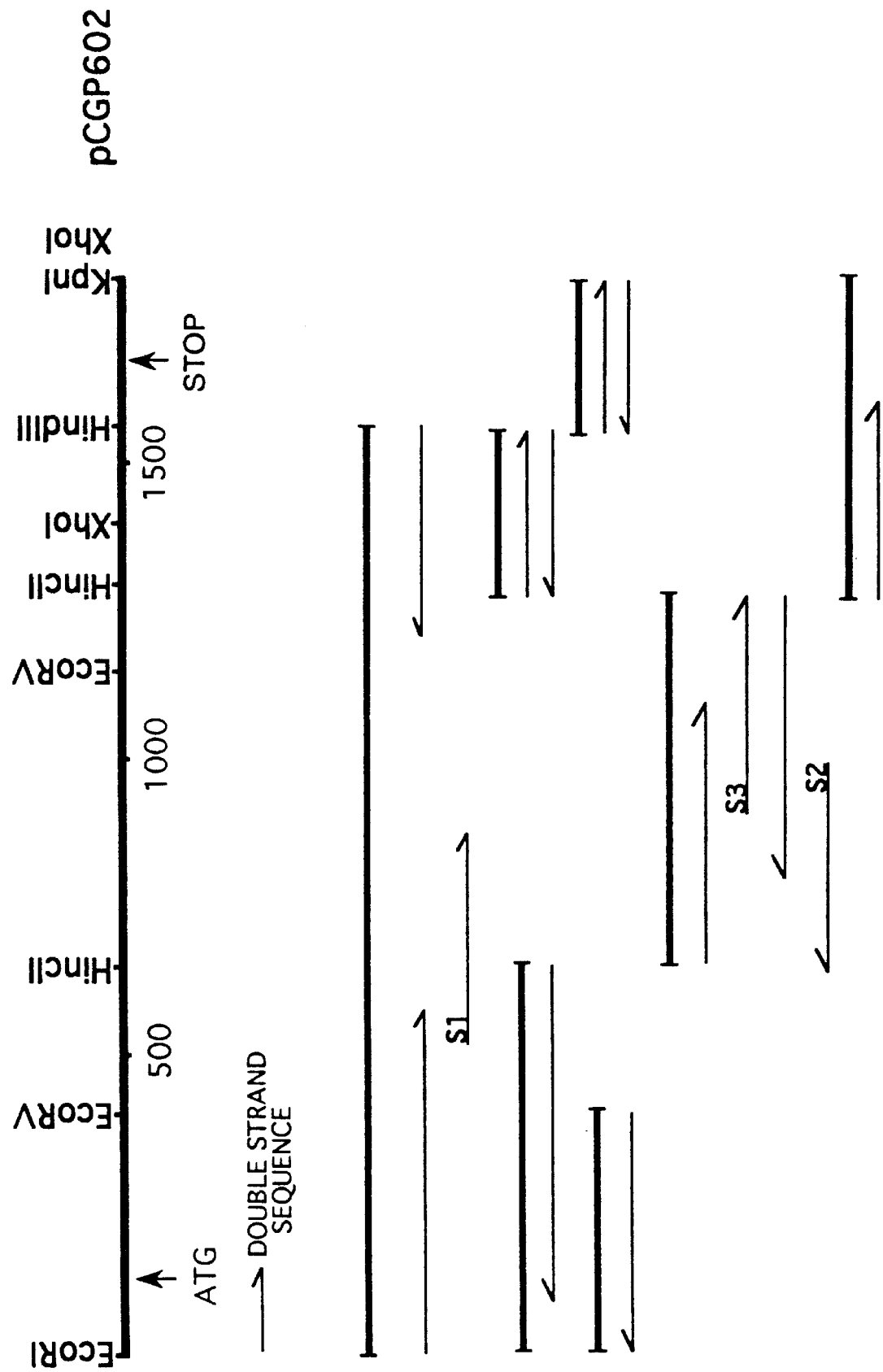

FIG. 8 shows a diagrammatic representation of a restriction enzyme map of pCGP602. Partial lengths of the cDNA insert are indicated by the bolder lines with solid ends (as opposed to arrows). These were subcloned into M13-mp18 and mp19 and sequenced using oligonucleotide primer sequences, as indicated, to obtain overlapping sequence information. The extent and direction of sequence information obtained from each subcloned piece is shown by lines with half arrow-heads. S1=primer sequence 1; S2=primer sequence 2; S3=primer sequence 3; ATG indicates the methionine initiation codon and the total length of the clone in base pairs is also indicated.

Figures 9A, 9B, 9C, 9D:
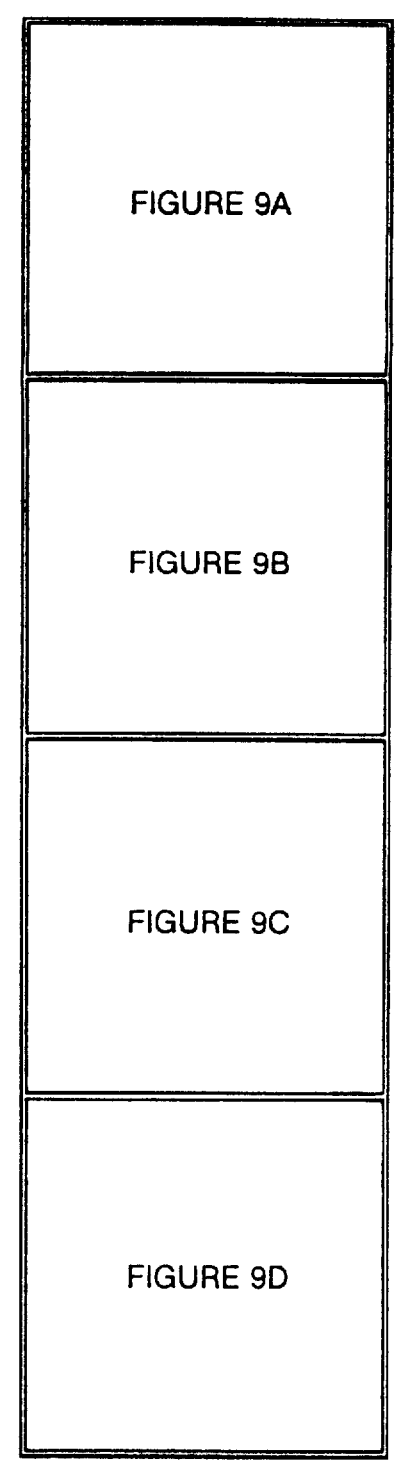

FIGS. 9(A) to (D) are the nucleotide sequences and predicted amino acid sequences for the cDNA inserts from pCGP176 and pCGP602. The insert from pCGP602 includes the entire sequence shown. The 5' end of the pCGP176 insert is indicated with an arrowhead.

Figures 10A, 10B, 10C:
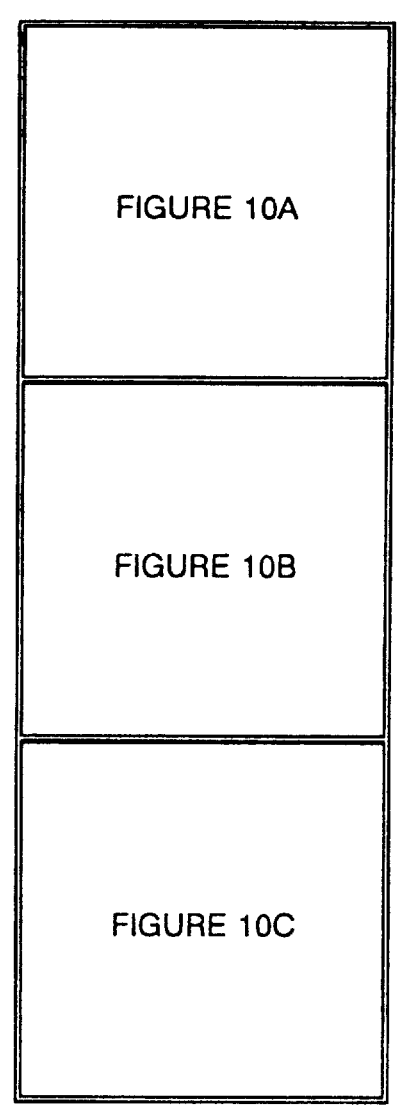

FIGS. 10(A) to (C) represent the nucleotide sequence and predicted amino acid sequence for the cDNA insert from pCGP175.

Figure 11:
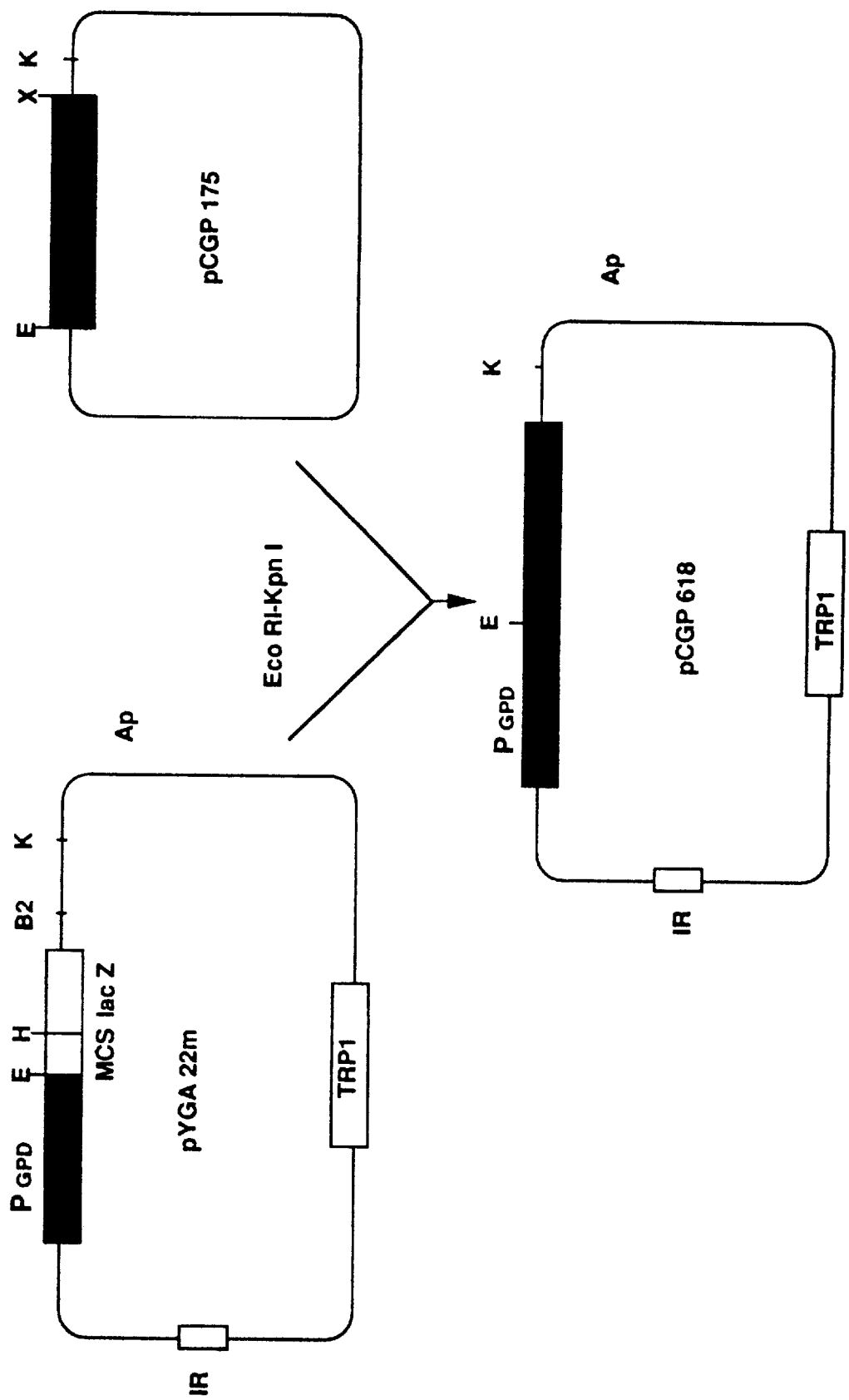

FIG. 11 is a diagrammatic representation of the construction of pCGP618. pCGP618 was constructed by cloning the pCGP175 cDNA insert in a sense orientation behind the yeast glyceraldehyde-3-phosphate dehydrogenase promoter (PGPD) in the expression vector pYGA22m. The cDNA insert from pCGP175 was ligated as an EcoRI-KpnI fragment with the large fragment that resulted from an EcoRI/KpnI digest of pYGA22m. E=EcoRI, H=HindIII, K=KpnI, X=XhoI, IR=Inverted repeat of 2 μm plasmid, Trp1=Trp1 gene, Ap=Ampicillin resistance marker.

Figure 12A:
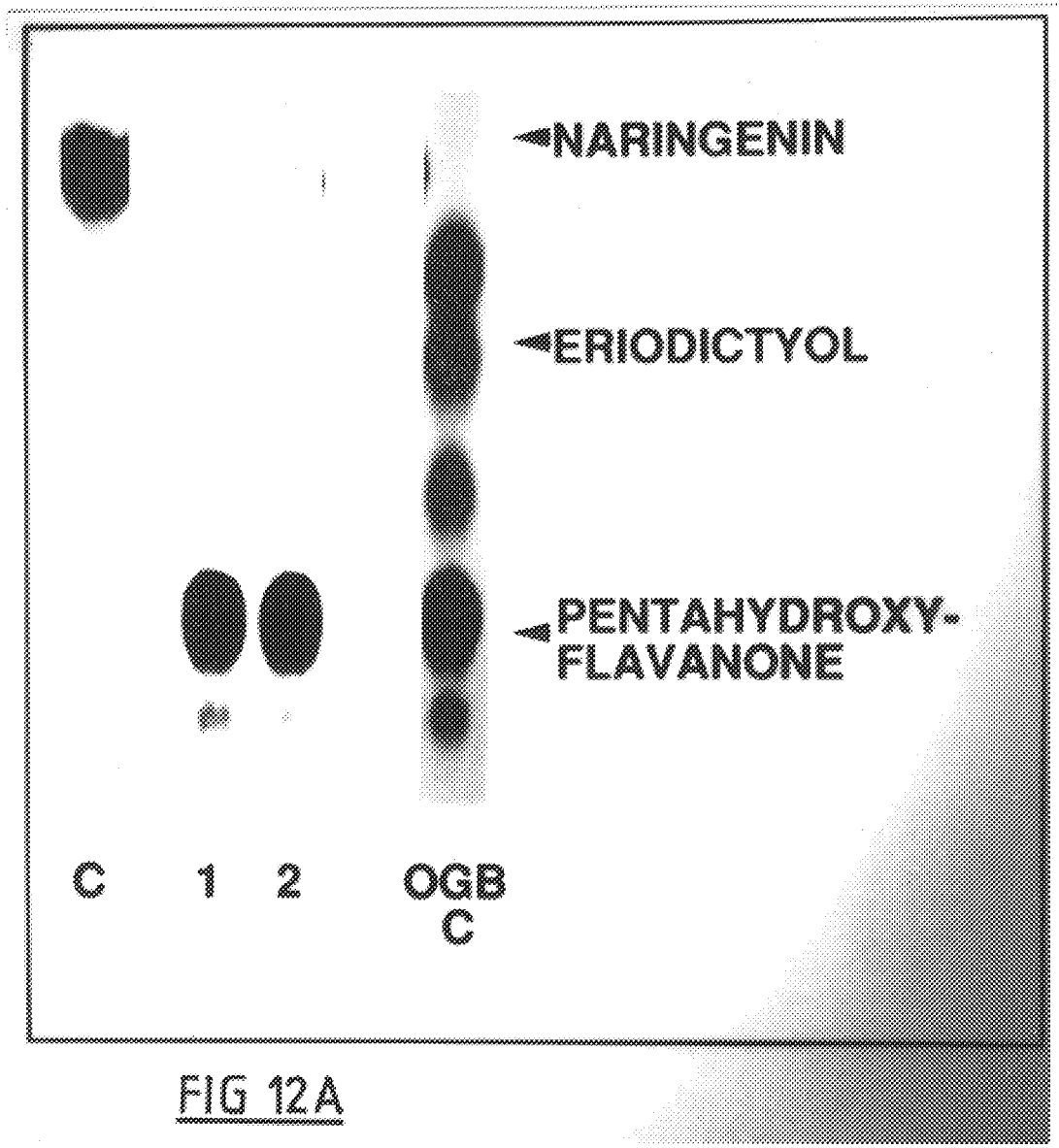

FIG. 12(A) shows a 3',5'-hydroxylase assay of yeast extracts using $^3$H-naringenin as substrate. The autoradiographs show conversion of $^3$H-naringenin to the 3',5'-hydroxylated derivative pentahydroxyflavanone by extracts of yeast transformed with the plasmid pCGP618 (1 and 2). No 3',5'-hydroxylase activity was detected in untransformed yeast (C). Conversion of naringenin to pentahydroxyflavanone by OGB 3',5'-hydroxylase is also shown (OGB C).

Figure 12B:
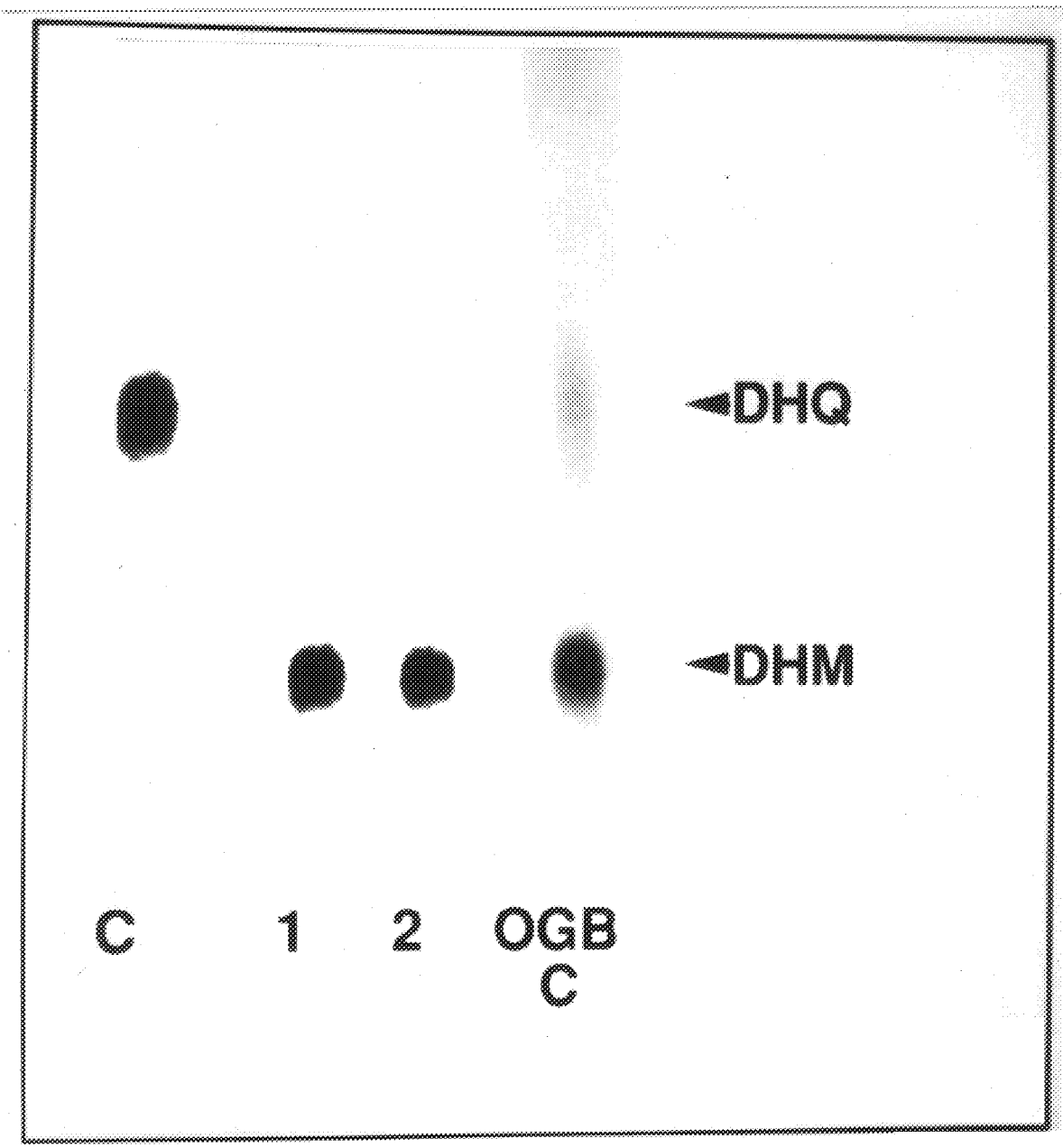

FIG. 12(B) shows a 3',5'-hydroxylase assay of yeast extracts using $^3$H-dihydroquercetin as substrate. The autoradiographs show conversion of $^3$H-dihydroquercetin (DHQ) to $^3$H-dihydromyricetin (DHM) by extracts of yeast transformed with the plasmid pCGP618 (1 and 2). No 3',5'-hydroxylase activity was detected in untransformed yeast (C). Conversion of DHQ to DHM by OGB 3',5'-hydroxylase is also shown (OGB C).

Figure 13:
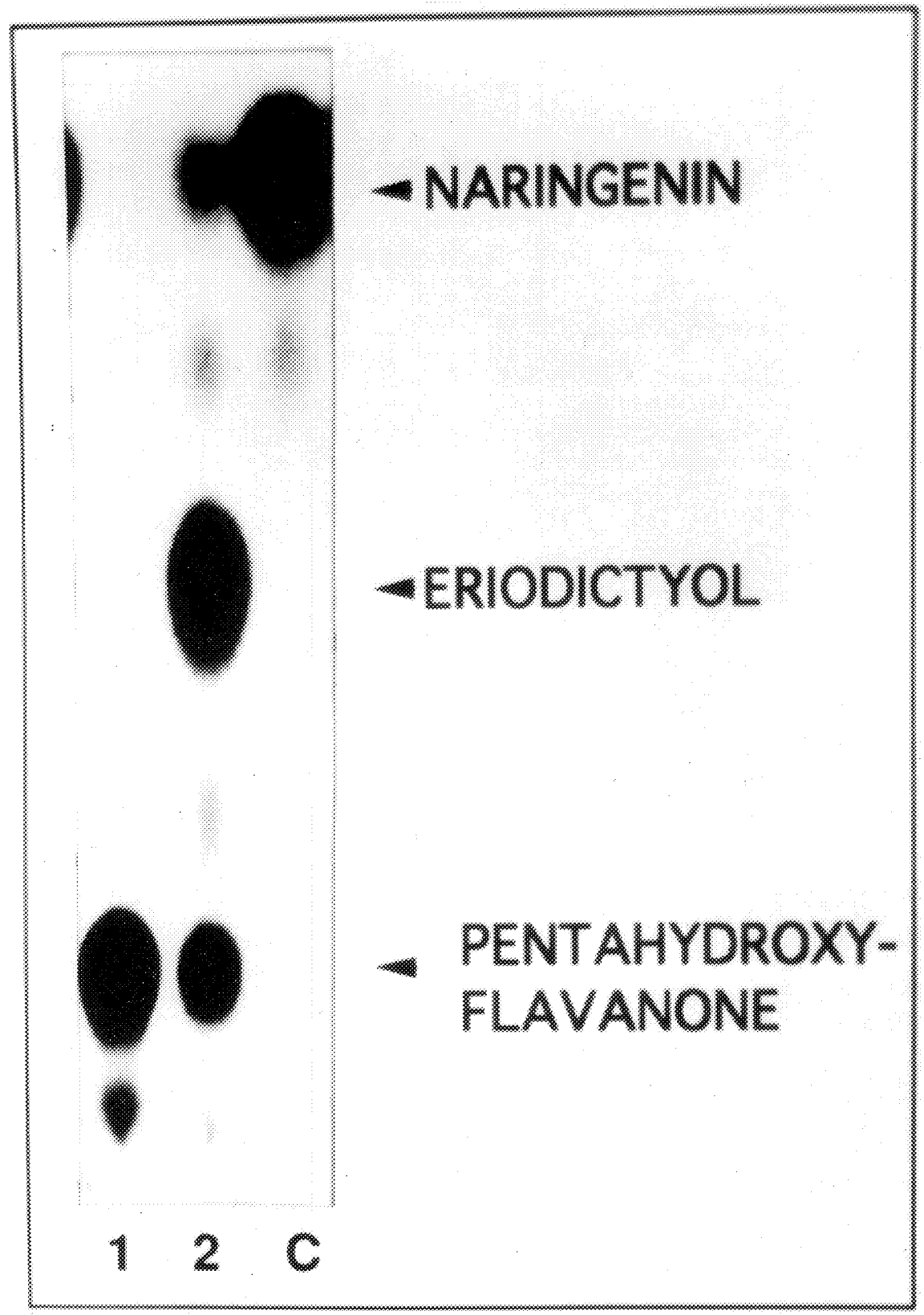

FIG. 13 shows a 3',5'-hydroxylase assay of yeast extracts using $^3$H-naringenin as substrate. The autoradiograph shows conversion of $^3$H-naringenin to the 3',5'-hydroxylated derivative pentahydroxyflavanone by extracts of yeast transformed with plasmids pCGP618 and pCGP620 (1 and 2, respectively). The reaction products obtained from the pCGP620 extract also included the 3'-hydroxylated eriodictyol as well as some of the original naringenin substrate indicating incomplete conversion to the 3',5'-hydroxylated end product. No 3',5'-hydroxylase activity was detected in untransformed yeast (C).

Figure 14:
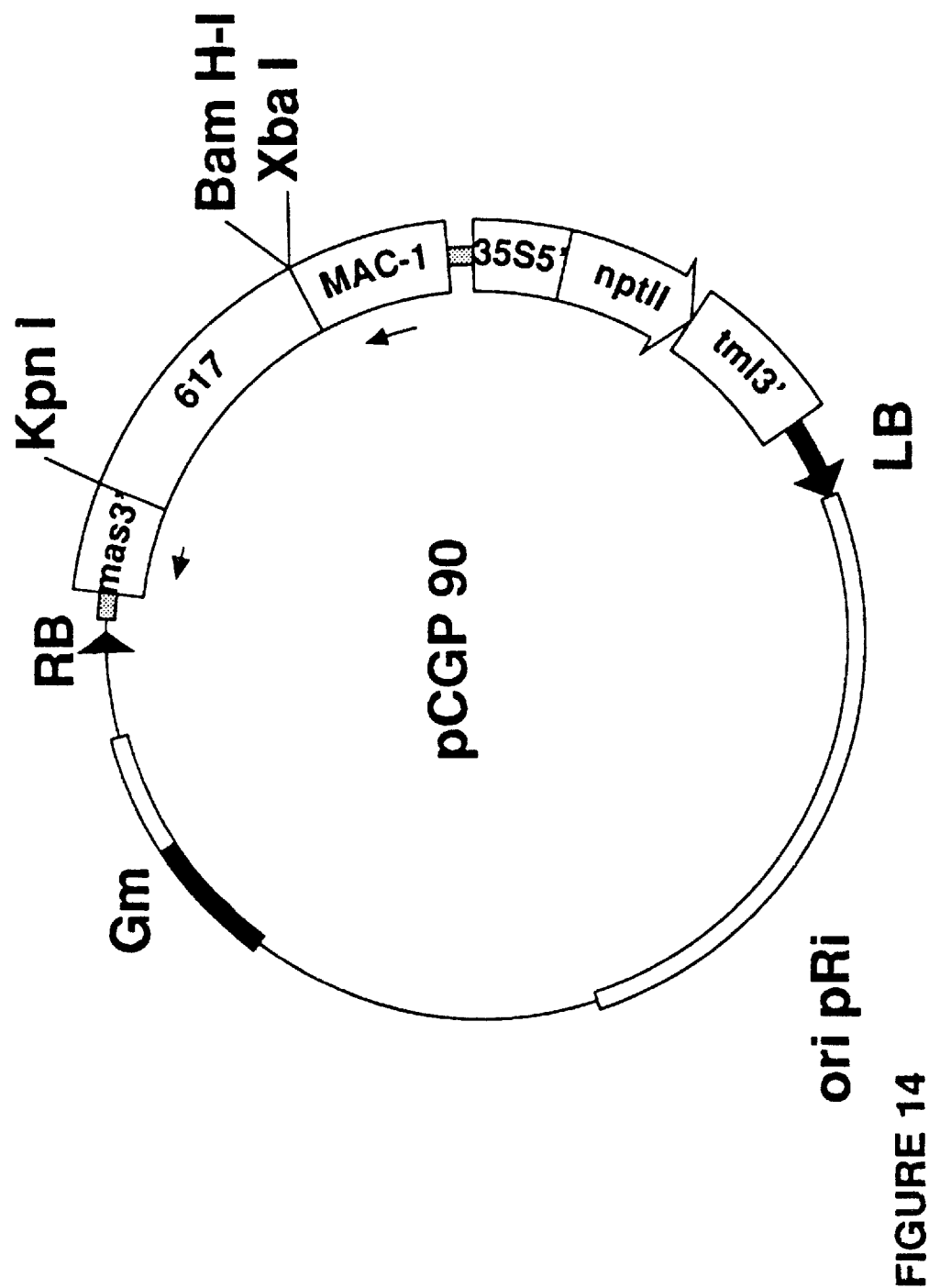

FIG. 14 is a diagrammatic representation of the plasmid pCGP90. The cDNA insert from pCGP602 was cloned in a sense orientation behind the Mac promoter of the expression vector pCGP293 as illustrated.

Figure 15:
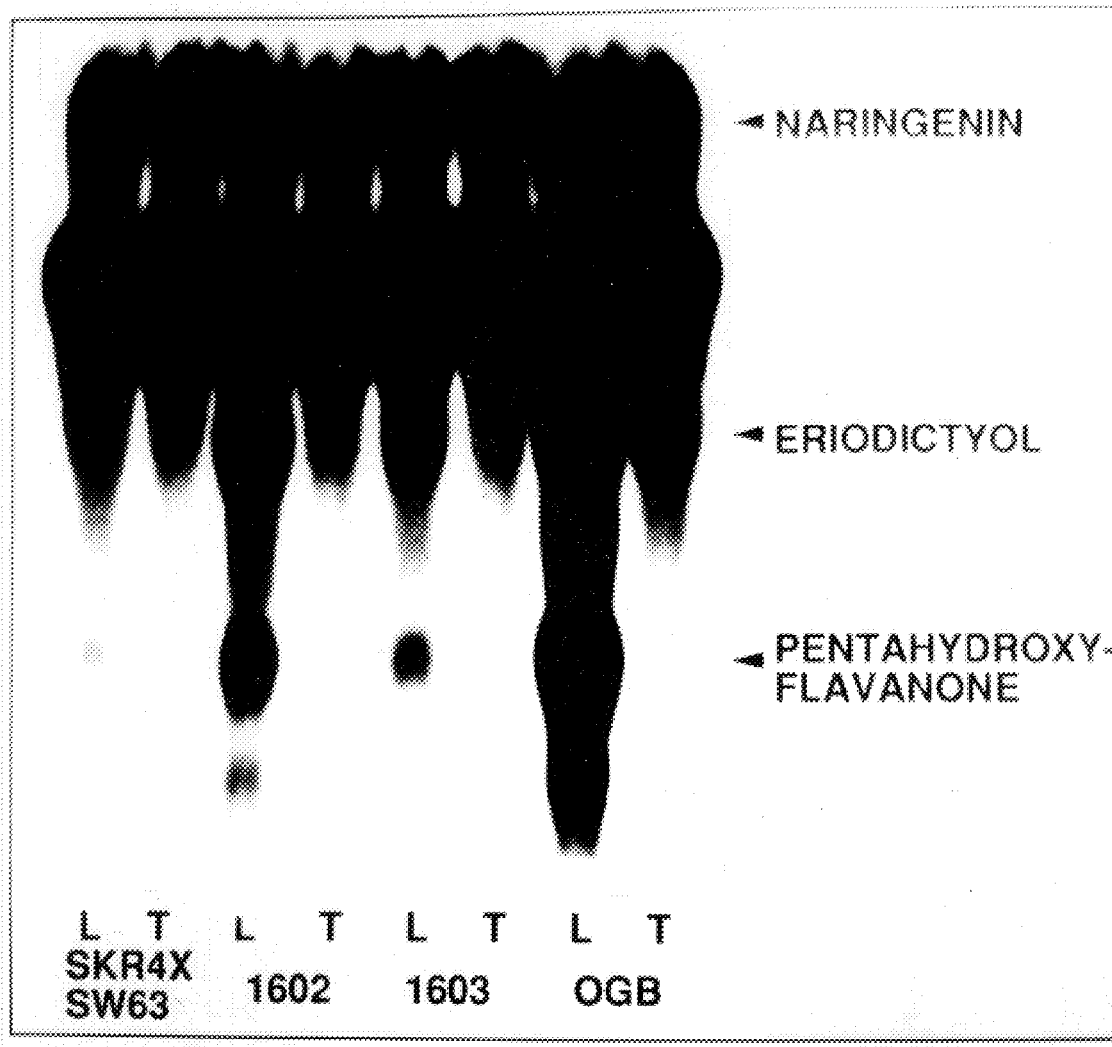

FIG. 15 shows a 3',5'-hydroxylase assay of petunia petal extracts. The autoradiograph shows the presence of low levels of 3',5'-hydroxylase activity (conversion of $^3$H-naringenin to $^3$H-pentahydroxyflavanone) in petal limb tissue (L) of Skr4×Sw63. Significantly higher levels of activity were detected in the limb tissue (L) of two Skr4× Sw63/pCGP90 transgenics (T/G 1602 and T/G 1603). No 3',5'-hydroxylase activity was detected in extracts of the petal tube (T) of either the non-transgenic Skr4×Sw63 hybrid or the two pCGP90 transgenics. Conversion of naringenin to pentahydroxyflavanone by extracts of limb (L) and tube (T) petal tissue of OGB is also shown.

Figures 16A, 16B, 16C:
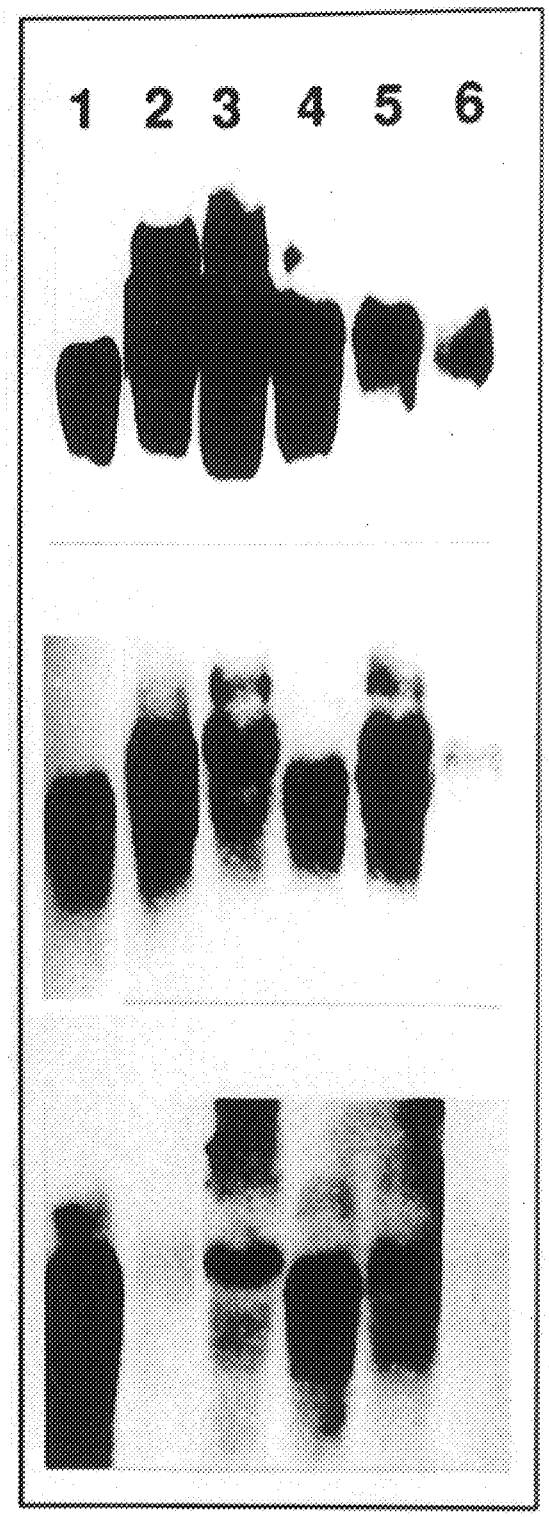

FIG. 16 is a photographic representation of an autoradiograph of an RNA blot probed with $^{32}$P-labelled Hf1 cDNA. Each lane contained a 20 μg sample of total RNA isolated from (1) *P. hybrida* cv. OGB petals; (2) pansy petals; (3) potato stems; (4) eggplant skins; (5) *Nicotiana alata* flowers; (6) Ageratum flowers. The probe used for A and B was derived from a 660 bp BalI DNA fragment; a 1.4 kb EcoRI/HindIII fragment was used for C. Washing conditions used were: (A) 6×SSC at 50° C.; (B) 2×SSC at 50° C.; (C) 0.2×SSC at 65° C.

Figures 17A, 17B:
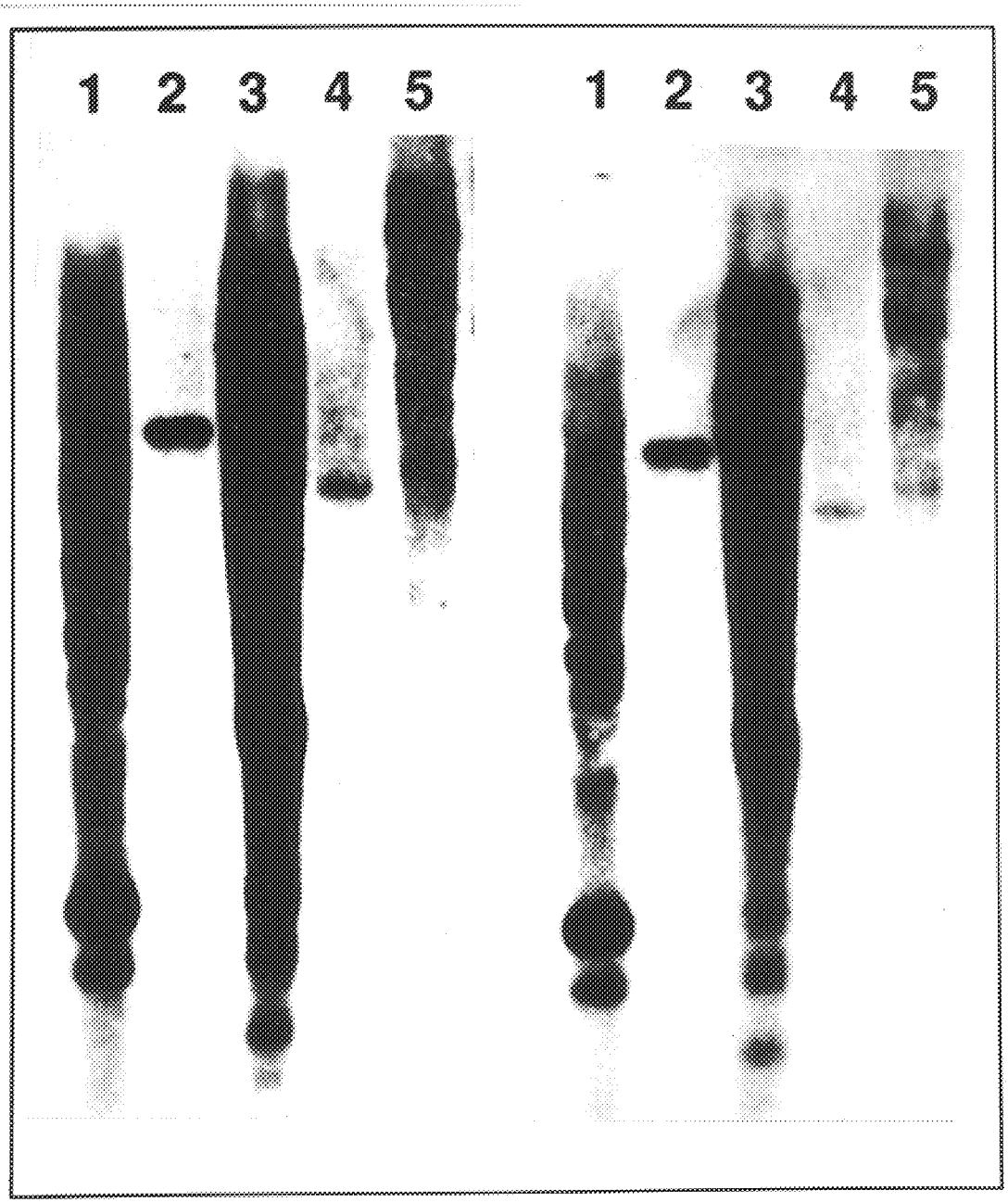

FIG. 17 is a photographic representation of autoradiographs of Southern blots probed with $^{32}$P-labelled Hf1 cDNA. Each lane contained 10 μg of DNA digested with EcoRI. The DNA samples were isolated from (1) eggplant, (2) dutch iris, (3) potato, (4) violets and (5) anemone. Washing conditions were: (A) 6×SSC at 50° C.; (B) 2×SSC at 65° C.

EXAMPLE

1. Materials and Methods

Chemicals Enzymes and Radioisotopes

Eriodictyol and dihydroquercetin were obtained from Carl Roth KG and naringenin was obtained from Sigma. Dihydromyricetin was chemically synthesized from myricetin (Extra Synthese, France) by the method of Vercruysse et al. (1985). [$^3$H]-naringenin (5.7 Ci/mmole) and [$^3$H]-dihydroquercetin (12.4 Ci/mmole) were obtained from Amersham. All enzymes were obtained from commercial sources and used according to the manufacturer's recommendations.

Bacterial Strains

The *Escherichia coli* strains used were;

DH5α supE44, Δ(lacZYA-ArgF)U169, φ80lacZΔM15, hsdR17 ($r_k^-$, $m_k^+$), recA1, endA1, gyrA96, thi-1, relA1, deoR. (Hanahan, 1983 and BRL, 1986).

XL1-Blue supE44, hsdR17 ($r_k^-$, $m_k^+$), recA1, endA1, gyrA96, thi-1, relA1, lac$^-$, [F'proAB, lacI$^q$, lacZΔM15, Tn10(tet$^r$)] (Bullock et al, 1987).

PLK-F' recA, hsdR17 ($r_k^-$, $m_k^+$), mcrA$^-$, mcrB$^-$, lac$^-$, supE44, galK2, galT22, metB1, [F' proAB, lacI$^q$, lacZΔM15, Tn10(tet$^r$)] (Stratagene).

The disarmed *Agrobacterium tumefaciens* strain AGL0 (Lazo et al, 1991) was obtained from R. Ludwig (Department of Biology, University of California, Santa Cruz).

The cloning vectors pBluescript and pBluescribe were obtained from Stratagene.

Transformation of *E. coli* and *A. tumefaciens*

Transformation of the *E. coli* strain DH5α cells was performed according to the method of Inoue et al. (1990).

The plasmid pCGP90 (FIG. 14) was introduced into the *Agrobacterium tumefaciens* strain AGL0 by adding 5 μg of plasmid DNA to 100 μL of competent AGL0 cells prepared by inoculating a 50 mL MG/L (Garfinkel and Nester, 1980) culture and growing for 16 hrs with shaking at 28° C. The cells were then pelleted and resuspended in 0.5 mL of 85% (v/v) 100 mM CaCl$_2$/15% (v/v) glycerol. The DNA-Agrobacterium mixture was frozen by incubation in liquid N$_2$ for 2 minutes and then allowed to thaw by incubation at 37° C. for 5 minutes. The DNA/bacterial mix was then placed on ice for a further 10 minutes. The cells were then mixed with 1 mL of MG/L media and incubated with shaking for 16 hours at 28° C. Cells of *A. tumefaciens* carrying pCGP90 were selected on MG/L agar plates containing 100 μg/mL gentamycin. The presence of pCGP90 was confirmed by Southern analysis of DNA isolated from the gentamycin resistant transform ants.

The *Petunia hybrida* varieties used are shown in Table 2.

TABLE 2

Plant Material

| Plant variety | Properties | Source/Reference |
|---|---|---|
| Old Glory Blue(OGB) F$_1$ Hybrid | | Ball Seed, USA |
| V30 | An1, An2, An3, An4, An6 An8, An9, An10, An11, Ph1 Ph2, Ph3, Ph4, Ph5, Hf1, Hf2, Ht1, Ht2, Rt, Mt1, Mt2, mf1, po, Gf | Koes et al. (1986) |
| V23 | An1, An2, An3, An4, An6 An8, An9, An10, ph1, Hf1, Hf2, ht1, Rt, Po, B1, F1 | Wallroth et al. (1986) Doodeman et al. 1984 |
| R51 | An1, An2, An3, An4, An6, An8, An9, An10, An11, Ph1, hf1, hf2, Ht1, rt, po, b1, f1 | Wallroth et al. (1986) van Tunen et al. (1990) Doodeman et al. (1984) |
| Sw63 | An1, An2, An3, an4, An6, An8, An9, An10, An11, Ph1, Ph2, Ph5, hf1, hf2 ht1, ht2, rt, po, mf1, f1, Gf | I.N.R.A., Dijon, Cedex, France |
| Th7 | An1, An2, An3, An4, An6 An9, An10, An11, Hf1, HF2, Ht1, Ht2, Ph1, Ph2, Ph5, Rt, po, mf1, mf2, Gf, f1 | I.N.R.A., Dijon, Cedex, France |
| Skr4 | An1, An2, An3, An4, An6, An11, hf1, hf2, ht1, Ph1, Ph2, Ph5, rt, Po, Mf1, Mf2, f1 | I.N.R.A., Dijon, Cedex, France |
| Skr4 × Sw63 | Skr4 × Sw63 F$_1$ Hybrid | |
| Rw14 | An1, An2, An4, Ph1, ph2, Ph5, hf1, hf2, Ht1, Rt, Po, B1, Lg1, Lu1, Vs1, Vs3, Vs5, la, Yg1, ws, Gf, Mt1, Mf2, f1 | I.N.R.A., Dijon, Cedex France |
| Rp57 | An1, An2, An4, Ph1, ph2, Ph5, hf1, hf2, Ht1, Rt, Po, Mt, Mf, f1, Gf, B1, Lg1, Lu1, Vs1, Vs3, Vs5, Yg1, Ws. | I.N.R.A., Dijon, Cedex, France |
| Rp57 × Rw14 | Rp57 × Rw14 F$_1$ Hybrid | |

Plants were grown in specialised growth rooms with a 14 hr day length at a light intensity of 10,000 lux and a temperature of 22° to 26° C. OGB flowers were harvested at developmental stages defined as follows:

Stage 1: Unpigmented, closed bud (<25 mm in length)

Stage 2: Pigmented, closed bud (25–35 mm in length).

Stage 3: Dark purple bud with emerging corolla (>35 mm in length).

Stage 4: Dark purple opened flower pre-anther dehiscence (>50 mm in length).

Stage 5: Fully opened flower with all anthers dehisced.

Flowers of the other varieties, as described in Table 2, were harvested prior to anther dehiscence at the stage of maximum pigment accumulation.

Preparation of Plant Extracts for Assay of 3',5'-Hydroxylase Activity

Plant tissue was homogenised in a 2 to 5 times volume of ice-cold extraction buffer (100 mM potassium phosphate (pH 7.5), 1 mM EDTA, 0.25M sucrose, 0.25M mannitol, 0.1% (w/v) BSA, 100 nM Pepstatin, 100 nM Leupeptin, 0.1 mg/mL PMSF, 20 mM 2-mercaptoethanol and 10 mg/mL polyclar AT). The homogenate was centrifuged at 10,000 rpm in a JA20 rotor (Beckman) for 10 min at 4° C. and an aliquot of the supernatant was assayed for 3',5'-hydroxylase activity.

3',5'-Hydroxylase Assay

3',5'-Hydroxylase enzyme activity was measured using a modified version of the method described by Stotz and Forkmann (1982). The assay reaction mixture typically contained 100 µL of plant extract, 5 µL of 50 mM NADPH in assay buffer (100 mM potassium phosphate (pH8.0), 1 mM EDTA and 20 mM 2-mercaptoethanol), 10 µCi of [$^3$H] naringenin or 5 µCi of [$^3$H]-dihydroquercetin and was made up to a final volume of 210 µL with the assay buffer. Following incubation at 23° C. for 2–16 hours, the reaction mixture was extracted with 0.5 mL of ethylacetate. The ethyl acetate phase was dried under vacuum and then resuspended in 10 µL of ethyl acetate. The tritiated flavonoid molecules were separated on cellulose thin layer plates (Merck Art 5577, Germany) using a chloroform:acetic acid:water (10:9:1, v/v) solvent system. At the completion of the chromatography, the TLC plates were sprayed with 7% (v/v) 2,5-diphenyloxazol in diethyl ether. The reaction products were localised by autoradiography and identified by comparison to non-radioactive naringenin, eriodictyol, dihydroquercetin and dihydromyricetin standards which were run alongside the reaction products and visualized under UV light.

Glucose/High Light Induction of Delphinidin Synthesis in Leaves

Leaves were harvested from P. hybrida cv. OGB and cut into 1 cm² sections in sterile water. The leaf sections were then floated on a 2% (w/v) glucose solution and exposed to a light intensity of 24,000 lux for 96 hours.

Construction of cDNA Library #1

Twenty grams of stage 3 to 4 OGB flower limbs were homogenised in 100 mL of PEB (200 mM Tris-HCl (pH 8.6), 60 mM KCl, 30 mM MgCl$_2$, 25 mM EGTA) containing 10 mM vanadyl ribonucleoside complex. Cell debris was removed by filtering the homogenate through sterile Miracloth (Calbiochem). The filtrate was layered on top of a step gradient of 6 mL of PEB containing 25% (w/v) sucrose, 250 units InhibitAce (5-Prime 3-Prime), and 6 mL of PEB containing 50% (w/v) sucrose and 250 units InhibitAce in Ultra-Clear™ Quick-Seal™ (Beckman) centrifuge tubes. The tubes were centrifuged for 3.5 hours at 26,000 rpm in a 70 Ti rotor. Membrane-bound polysomes were collected from the 25% (w/v) sucrose /50% (w/v) sucrose interface and added to a 4M guanidium isothiocyanate solution. RNA was isolated from the denatured polysomes by pelleting through a 5.7M CsCl cushion, as described by Turpen and Griffith (1986).

A Uni-ZAP™ XR vector kit (Stratagene) was used to construct a directional cDNA library in λZAP using 25 µg of the polysomal RNA as template. The primary library, which contained 250,000 plaque forming units (pfu), was amplified by overnight growth on NZY plates (Sambrook et al, 1989) and the amplified phage stock was eluted in PSB (100 mM NaCl, 8 mM MgSO$_4$, 50 mM Tris-HCl (pH 7.5), 0.01% (w/v) gelatin) as described by Sambrook et al, (1989).

Construction of cDNA Library #2

Total RNA was isolated from the petal tissue of P. hybrida cv. OGB stage 3 to 4 flowers using the method of Turpen and Griffith (1986). poly(A)$^+$ RNA was selected from the total RNA by three cycles of oligo-dT cellulose chromatography (Aviv and Leder, 1972).

Two micrograms of poly(A)$^+$ RNA were reverse transcribed in a 20 µL volume containing 1×Superscript™ reaction buffer, 10 mM dithiothreitol, 500 µM dATP, 500 µM dGTP, 500 µM dTTP, 500 µM 5-methyl-dCTP, 0.75 µg oligonucleotide #8 and 2 µL Superscript™ reverse transcriptase (BRL). The reaction mix was incubated at 37° C. for 50 minutes, 44° C. for 10 minutes, then placed on ice.

Second strand reaction mix (140 µL) was added to the first strand reaction. The second strand reaction mix consisted of 21 mM Tris-HCl, 104 mM KCl, 5.3 mM MgCl$_2$, 171 µM β-NAD, 11.4 mM (NH$_4$)$_2$SO$_4$, 214 µM dATP, 642 µM dCTP, 214 µM dGTP, 214 µM dTTP, 4 mM DTT, 10 µCi $^{32}$P-dCTP (3000 Ci/mMole), 15 units E. coli DNA ligase, 40 units DNA polymerase (Boehringer) and 0.8 units RNAse H. The final mixture was incubated for 150 minutes at 16° C. To make the double-stranded cDNA blunt-ended, 10 units T4 DNA polymerase was added, and the reaction continued for a further 15 minutes at 16° C. The reaction was stopped and the cDNA purified by phenol/chloroform extraction, followed by chloroform extraction and ethanol precipitation.

EcoRI adaptors (Promega) were ligated with the cDNA and then kinased using conditions recommended by the manufacturer. The enzymes were denatured by heat (70° C., 20 minutes) and the DNA was purified by phenol/chloroform extraction and ethanol precipitation. The cDNA was digested with 50 units XhoI (Boehringer) in a reaction volume of 100 µL, using conditions recommended by the manufacturer. The enzyme was heat killed (70° C., 20 minutes) and the mixture passed through an S400 spun column (Pharmacia) which had been equilibrated in STE buffer (Sambrook et al, 1989). The eluate was phenol/chloroform extracted and ethanol precipitated. After microcentrifugation at 4° C. for 30 minutes the cDNA pellet was rinsed with 70% (v/v) ethanol, air dried and resuspended in 10 µL of TE buffer (10 mM Tris-HCl (pH7.5), 1 mM EDTA).

NA-45 membrane (Schleicher and Schuell) was used to isolate cDNA in the size range of 1.3 to 2.5 kb from a 7.5 µL sample that had been electrophoresed through a 1% (w/v) agarose gel.

The size fractionated cDNA was ligated with 1 µg λZAPII EcoRI/XhoI/CIAP treated vector (Stratagene) in 5 µL reaction buffer consisting of 50 mM Tris-HCl (pH 7.0), 10 mM MgCl$_2$, 10 mM dithiothreitol, 1 mM ATP and 2 units T4 DNA ligase. The reaction was performed at 4° C. for 2 days.

After leaving at room temperature for two hours, the ligation reaction mixture was packaged using the Packagene system (Promega). The total number of recombinants was 270,000 pfu.

An amount of 150,000 pfu of the packaged cDNA was plated at 10,000 pfu per 15 cm diameter plate after transfecting PLK-F' cells. The plates were incubated at 37° C. for eight hours, then stored overnight at 4° C. Duplicate lifts were taken onto Colony/Plaque Screen™ filters (Dupont) and treated as recommended by the manufacturer.

Synthesis of Oligonucleotides

Oligonucleotides were synthesized on an Applied Biosystems PCR-Mate DNA synthesizer using methods recommended by the manufacturer. The oligonucleotides synthesized were, 5'-3':

Oligo 1 (SEQ ID NO:3): GGAAGCTTATICCITT(T/C)GGIGCIGG

Oligo 2 (SEQ ID NO:4): GGATGACTCAGTAAAACGACGGCCAGT

Oligo 3 (SEQ ID NO:5): CCIGG(A/G)CAIATIC(G/T)(C/T)(C/T)TICCIGCICC(A/G)AAIGG

Oligo 4 (SEQ ID NO:6): GGATGACTCAAACAGCTATGACCATG

Oligo 5 (SEQ ID NO:7): GTTCAATTCGGAATGATG

Oligo 6 (SEQ ID NO:8): GCTGCACTTAATCCATAT

Oligo 7 (SEQ ID NO:9): TGCATAGCTTTGGG

Oligo 8 (SEQ ID NO:10): GAGAGAGAGAGAGAGAGAGATCTCGAGTTTTTTTTTTTTTTTTTTT

Oligo 9 (SEQ ID NO:11): ATGTCTCCTCCAGTG

Oligo 10 (SEQ ID NO:12): CTAGACTCCAATCAC

Oligos 2 and 4 included a GCN4 binding site (indicated by underlining) which has been shown to facilitate the enrichment of double stranded PCR products (Lew and Kemp, 1989).

The basis for the design of oligo 3 was as follows: Amino acid sequences from the putative haem-binding domain of an avocado cytochrome P450 (Bozak et al, 1990) and the corresponding sequences encoded by the two petunia cytochrome P450 homologues pCGP142 and pCGP147 were aligned:

| avocado (SEQ ID NO: 13) | P F G A G R R G C P G |
|---|---|
| pCGP142 (SEQ ID NO: 14) | P F G A G K R I C P G |
| pCGP147 (SEQ ID NO: 15) | P F G S G R R I C P G |

The consensus amino acid sequence of the haem-binding region for the three plant cytochromes P450 could thereby be seen to be:
P F G A(S) G R(K) R I(G) C P G Possible permutations of nucleotide sequence that could encode the amino acids found in the haem-binding domain of the three cytochrome P450 molecules could then be deduced:

```
5'- CCX   TTT  GGX GCX  GGX  AGX  CGX  ATX   TGT  CCX  GGX -3'
          C        AG         CA   A    GG         C
                 T
```

X indicates nucleotide positions where all four nucleotides (A,C,G and T) can be used. Oligo 3 was designed to complement a subset of the consensus sequence derived from the three plant cytochromes P450. Deoxyinosine (I) was used predominantly when base degeneracy was greater than three. The resulting oligonucleotide sequence was as shown above.

PCR Reactions

Helper phage R408 (Stratagene) was used to excise pBluescript phagemids containing petunia cDNA inserts from 200,000 pfu of the amplified λZAP cDNA library #1 using methods described by the manufacturer. *Escherichia coli* XL1-Blue were transfected with the phagemid mixture and 250,000 colonies were plated out on ampicillin-containing media. Cells were resuspended in LB (Sambrook et al, 1989) and plasmid DNA was isolated using an alkaline lysis procedure (Sambrook et al, 1989). Plasmid DNA was further purified by banding on a CsCl gradient. This DNA was used as the template for PCR.

PCR reactions for amplification of petal cytochrome P450 homologues contained 5 to 100 ng of excised DNA, 10 mM Tris-HCl (pH 8.3), 50 mM KCl, 1.5 mM $MgCl_2$, 0.01% (w/v) gelatin, 0.2 mM each dNTP, 0.4 µM each primer and 1.25 units Taq polymerase (Cetus). Reaction mixes (50 µL) were cycled 30 times between 94° C., 48° C. and 72° C. for 1 minute at each temperature. The amplified products were gel-purified using Geneclean (Bio 101 Inc.), reamplified to obtain sufficient material for cloning and then end-repaired using T4 DNA polymerase. DNA amplified using oligos 1 and 2 was digested with HindIII and XhoI prior to cloning into pBluescript. The PCR product generated by amplification between oligos 3 and 4 was cloned directly into the ddT-tailed pBluescript vector described by Holton and Graham (1991).

Screening of cDNA Libraries

Duplicate plaque lifts were hybridised and washed as follows: High stringency conditions (hybridization: 50% (v/v) formamide, 6×SSC, 1% (w/v) SDS at 42° C. for 16 hrs and washing: 2×SSC, 1% (w/v) SDS at 65° C. for 2×15 minutes followed by 0.2×SSC, 1% (w/v) SDS at 65° C. for 2×15 minutes) were used to detect sibling clones and low stringency conditions (hybridisation: 20% (v/v) formamide, 6×SSC, 1% (w/v) SDS at 42° C. for 16 hrs and washing: 6×SSC, 1% (w/v) SDS at 65° C. for 1 hour) were used to detect related sequences.

Northern Analysis

Total RNA was isolated from tissue that had been frozen in liquid $N_2$ and ground to a fine powder using a mortar and pestle. An extraction buffer of 4M guanidium isothiocyanate, 50 mM Tris-HCl (pH 8.0), 20 mM EDTA, 0.1% (v/v) Sarkosyl, was added to the tissue and the mixture was homogenized for 1 minute using a polytron at maximum speed. The suspension was filtered through Miracloth (Calbiochem) and centrifuged in a JA20 rotor for 10 minutes at 10,000 rpm. The supernatant was collected and made to 0.2 g/mL CsCl (w/v). Samples were then layered over a 10 mL cushion of 5.7M CsCl, 50 mM EDTA (pH 7.0) in 38.5 mL Quick-seal centrifuge tubes (Beckman) and centrifuged at 42,000 rpm for 12–16 hours at 23° C. in a Ti-70 rotor. Pellets were resuspended in TE/SDS (10 mM Tris-HCl (pH 7.5), 1 mM EDTA, 0.1% (w/v) SDS) and extracted with phenol:chloroform:isoamyl alcohol (25:24:1) saturated in 10 mM EDTA (pH 7.5). Following ethanol precipitation the RNA pellets were resuspended in TE/SDS.

RNA samples were electrophoresed through 2.2M formaldehyde/1.2% (w/v) agarose gels using running buffer containing 40 mM morpholinopropanesulphonic acid (pH 7.0), 5 mM sodium acetate, 0.1 mM EDTA (pH 8.0). The RNA was transferred to Hybond-N filters (Amersham) as described by the manufacturer and probed with $^{32}$P-labelled cDNA fragment ($10^8$ cpm/µg, $2 \times 10^6$ cpm/mL). Prehybridization (1 hr at 42° C.) and hybridization (16 hr at 42° C.) was carried out in 50% (v/v) formamide, 1M NaCl, 1% (w/v) SDS, 10% (w/v) dextran sulphate. Degraded salmon sperm DNA (100 µg/mL) was added with the $^{32}$P-labelled probe for the hybridization step.

Filters were washed in 2×SSC/1% (w/v) SDS at 65° C. for 1 to 2 hours and then 0.2×SSC/1% (w/v) SDS at 65° C. for 0.5 to 1 hour. Filters were exposed to Kodak XAR film with an intensifying screen at −70° C. for 48 hours.

RFLP Analysis a. Isolation of Genomic DNA

DNA was isolated from leaf tissue essentially as described by Dellaporta et al, (1983). The DNA preparations were further purified by CsCl buoyant density centrifugation (Sambrook et al, 1989).

b. Southern blots

The genomic DNA (10 µg) was digested for 16 hours with 60 units of XbaI and electrophoresed through a 0.7% (w/v) agarose gel in a running buffer of TAE (40 mM Tris-acetate, 50 mM EDTA). The DNA was then denatured in denaturing solution (1.5M NaCl/0.5M NaOH) for 1 to 1.5 hours, neutralized in 0.5M Tris-HCl (pH 7.5)/1.5M NaCl for 2 to 3 hours and the DNA was then transferred to a Hybond N (Amersham) filter in 20×SSC.

c. Isolation of chi-A probe

A cDNA clone of chi-A (van Tunen et al., 1988) was synthesized by PCR using cDNA template made from OGB stage 3 petal RNA and two oligonucleotide primers: #9, which covered nucleotides 6–20 and #10, which was complementary to nucleotides 711–725 of the published chi-A cDNA sequence (van Tunen et al, 1988). The resulting PCR product was ligated into the SmaI site of pBluescribe M13⁻ (Stratagene) and sequenced to confirm that the cloned fragment corresponded to the published sequence.

$^{32}$P-Labelling of DNA Probes

DNA fragments (50 to 100 ng) were radioactively labelled with 50 $\mu$Ci of [$\alpha$-$^{32}$P]-dCTP using an oligolabelling kit (Bresatec). Unincorporated [$\alpha$-$^{32}$P]-dCTP was removed by chromatography on a Sephadex G-50 (Fine) column.

DNA Sequence Analysis

DNA sequencing was performed essentially by the method of Sanger et al. (1977) using the Sequenase enzyme (USB, version 2.1). The complete sequence of clones pCGP602, pCGP176 and pCGP175 was determined by compilation of sequence from different M13 -mp18 and -mp19 (Norrander et al, 1983; Yanisch-Perron, 1985) subclones obtained using standard cloning procedures (Sambrook et al, 1989). For some regions it was necessary to synthesize specific oligonucleotide primers to obtain overlapping sequence data. The following six primers were synthesized for that purpose:

| 5' | CGTGCCAATGAGCTAGG | 3' | primer sequence (SEQ ID NO: 17) |
|---|---|---|---|
| 5' | GATGTTGGTTGTACTGAG | 3' | primer sequence (SEQ ID NO: 18) |
| 5' | GGAAACCAGATTTTCTTG | 3' | primer sequence (SEQ ID NO: 19) |
| 5' | TTTTTTTTTTTTTTTT(AGC) | 3' | primer sequence (SEQ ID NO: 20) |
| 5' | GTTTTCCCAGTCACGAC | 3' | primer −40 (SEQ ID NO: 21) |
| 5. | AACAGCTATGACCATG | 3' | reverse primer (SEQ ID NO: 22) |

A restriction map of pCGP602 showing the position of several of these sequences may be seen in FIG. 8.

Homology searches against Genbank, SWISS-PROT and EMBL databases were performed using the FASTA and TFASTA programs (Pearson and Lipman, 1988).

Construction of pCGP293

The expression binary vector pCGP293 was derived from the Ti binary vector pCGN1559 (McBride and Summerfelt, 1990). Plasmid pCGN1559 was digested with KpnI and the overhanging 3' ends were removed with T4 DNA polymerase according to standard protocols (Sambrook et al,1989). The vector was then further digested with XbaI and the resulting 5' overhang was repaired using the Klenow fragment of DNA polymerase I. The vector was then re-ligated to give pCGP67. A 1.97 kb PstI fragment containing the Mac promoter, mas terminator and various cloning sites (Comai et al, 1990) was isolated from pCGP40 and inserted into the PstI site of pCGP67 to give pCGP293.

Plasmid pCGP40 was constructed by removing the GUS gene (Jefferson et al, 1987) as a BamHI-SacI fragment from pCGN7334 and replacing it with the BamHI-SacI fragment from pBluescribe M13⁻ that includes the multicloning site. Plasmid pCGN7334 (obtained from Calgene, Inc. CA, USA), was constructed by inserting the fragment containing the Mac-GUS-mas gene fusion into the XhoI site of pCGN7329 (Comai et al, 1990).

Construction of pCGP90

Plasmid pCGP90 was constructed by cloning the cDNA insert from pCGP602 in a sense orientation behind the Mac promoter (Comai et al, 1990) of pCGP293. The BamHI-KpnI fragment containing the cDNA insert was isolated from pCGP602 and ligated with a BamHI/KpnI digest of pCGP293. Correct insertion of the insert in pCGP90 was established by restriction analysis of DNA isolated from gentamycin resistant transformants.

Construction of the Yeast Expression Vector pYGA22m

M13-mp18 was digested with EcoRI and BglII to produce a 700 bp fragment that contained a multicloning site. This fragment was ligated with the 9 kb EcoRI-BglII fragment from pYGA2269 (Ashikari et al, 1989). The resulting construct, designated pYGA22m, contained the multicloning site inserted downstream of the yeast glyceraldehyde-3-phosphate dehydrogenase promoter (FIG. 11).

Construction of pCGP618

A 1.8 kb EcoRI-KpnI fragment that included the entire cDNA insert from pCGP175 was ligated with the 9 kb EcoRI-KpnI fragment from pYGA22m. The resulting plasmid, pCGP618, contained the pCGP175 cDNA fragment ligated in a sense orientation behind the glyceraldehyde-3-phosphate dehydrogenase promoter (FIG. 11).

Construction of pCGP620

A 1.8 kb EcoRI-KpnI fragment that included the entire cDNA insert from pCGP176 was ligated with the 9 kb EcoRI-KpnI fragment from pYGA22m (as described for the construction of pCGP618). The resulting plasmid, pCGP620, contained the pCGP176 cDNA fragment ligated in a sense orientation behind the yeast glyceraldehyde-3-phosphate dehydrogenase promoter.

Yeast Transformation

The yeast strain G-1315 (Mat $\alpha$,trp1) (Ashikari et al, 1989) was transformed with pCGP618 and pCGP620 according to Ito et al, (1983). The transformants were selected by their ability to restore G-1315 to tryptophan prototrophy.

Preparation of Yeast Extracts for Assay of 3',5'-Hydroxylase Activity a. G-1315/pCGP618

Single isolates of G-1315/pCGP618 and a G-1315 revertant that grew on media lacking tryptophan were used to inoculate 50 mL of YNBC [1.2% (w/v) yeast nitrogen base without amino acids (Difco), 2% (w/v) glucose and 0.3% (w/v) Casamino acid (Difco)] and incubated with shaking for 2 days at 30° C. Cells were pelleted by centrifugation and a microsomal fraction was obtained according to Oeda et al. (1985) except that the spheroplasts were disrupted in the extraction buffer used for the assay of 3',5'-hydroxylase activity in plant tissue. Microsomal pellets were suspended in 400 $\mu$L of buffer A (10 mM Tris-HCl (pH 7.5), 0.65M sorbitol, 0.1 mM DTT, 0.1 mM EDTA) and a 100 $\mu$L sample was assayed for 3',5'-hydroxylase activity.

b. G-1315/pCGP620

A single isolate of G-1315/pCGP620 was used to inoculate 20 ml of YNBC which was subsequently incubated for 2 days at 30° C. Cells were collected by centrifugation, washed once with TE, once with buffer A, and then resuspended in buffer B (10 mM Tris-HCl (pH7.5), 1.2M sorbitol, 0.1 mM DTT, 0.1 mM EDTA) containing zymolyase (0.1 mg/mL) (Seikagakukogyo, Japan). Following incubation for 1 hour at 30° C. the cells were pelleted by centrifugation and resuspended in 400 $\mu$l of buffer A. The cell suspension was then vortexed with glass beads (diameter=0.4 mm) for 2 minutes and a 100 $\mu$l sample was assayed for 3',5'-hydroxylase activity.

Petunia Transformation a. Plant Material

Petunia hybrida (Skr4×Sw63 and Rp57×Rw14) seeds were sterilized in 1.25% (w/v) sodium hypochlorite for 10 min and rinsed three times in sterile water. Sterilized seeds were soaked in 100 mg/L gibberellic acid (GA$_3$) solution for 16 to 20 hours. They were then germinated for 2 weeks on 10% (w/v) MS (Murashige and Skoog, 1962) medium supplemented with 1% (v/v) sucrose and 0.8% (w/v) Difco Bacto agar. Young seedlings were transferred to MS medium supplemented with 3% (w/v) sucrose for 3 weeks before being transferred to Jiffy peat pellets (Jiffy Products Ltd, Norway), kept under mist and illuminated (135 $\mu$E. mercury halide light, 22° C.) for 2 to 3 weeks. These young plants were then transferred to a growth cabinet (68 $\mu$E. cool white fluorescent light, 25° C.). For co-cultivation, young leaves were harvested and sterilized in 1.35% (w/v) sodium hypochlorite for 2 min followed by rinsing three times in sterile water. Leaf tissue was then cut into 25 mm$^2$ squares and precultured on MS media supplemented with 0.05 mg/L kinetin and 1.0 mg/L 2,4-dichlorophenoxyacetic acid (2,4-D) for 24 hours.

b. Co-cultivation of Agrobacterium and Petunia Tissue

Agrobacterium tumefaciens strain AGL0 (Lazo et al, 1991) containing the binary vector pCGP90 (FIG. 14) was maintained at 4° C. on MG/L (Garfinkel and Nester, 1980) agar plates with 100 mg/L gentamycin. A single colony was grown overnight in liquid medium containing 1% (w/v) Bacto-peptone, 0.5% (w/v) Bacto-yeast extract and 1% (w/v) NaCl. A final concentration of $5 \times 10^8$ cells/mL was prepared the next day by dilution in liquid MS medium containing 3% (w/v) sucrose (BPM). Leaf discs were dipped for 5 minutes into BPM containing AGL0/pCGP90. The leaf discs were then blotted dry and placed on co-cultivation media for 4 days. The co-cultivation medium consisted of SH medium (Schenk and Hildebrandt, 1972) supplemented with 0.05 mg/L kinetin and 1.0 mg/L 2,4-D and included a feeder layer of tobacco cell suspension spread over the co-cultivation medium with a filter paper placed on top of the tobacco cell suspension.

c. Recovery of transgenic petunia plants

After co-cultivation, the leaf discs were transferred to the following selection media: Skr4×Sw63 discs to fresh MS medium supplemented with 3% (w/v) sucrose, 2 mg/L α-benzylaminopurine (BAP), 100 mg/L kanamycin, 350 mg/L cefotaxime, 0.3% (w/v) Gelrite Gellan Gum (Schweizerhall); Rp57×Rw14 discs to the same medium, containing 0.5 mg/L BAP and α-naphthalene acetic acid (NAA) instead of 2 mg/L BAP. After 3 weeks, regenerating explants were transferred to fresh medium. Adventitious shoots which survived the kanamycin selection were isolated and transferred to BPM containing 100 mg/L kanamycin and 350 mg/L cefotaxime for root induction. All cultures were maintained under a 16 hr photoperiod (60 $\mu$E. cool white fluorescent light) at 23°±2° C. When roots reached 2–3 cm in length the transgenic petunia plantlets were transferred to autoclaved Debco 51410/2 potting mix in 8 cm tubes. After 4 weeks plants were replanted into 15 cm pots using the same potting mix and maintained at 23° C. under a 14 hour photoperiod (300 $\mu$E. mercury halide light).

Tobacco Transformation a. Plant Material

Nicotiana tabacum (cv. Xanthi) stock plants were maintained on MS medium supplemented with 1 mg/L indolebutyric acid (IBA) and solidified with 0.25% (w/v) Gelrite. Leaf tissue was cut into 25 mm$^2$ squares and placed onto MS medium containing 1 mg/L BAP and 0.5 mg/L indoleacetic acid (IAA) for 24 hours.

b. Co-cultivation of Agrobacterium and tobacco tissue

Co-cultivation was carried out as previously described for petunia.

c. Recovery of transgenic tobacco plants

After co-cultivation, leaf discs were transferred to MS medium supplemented with 1 mg/L BAP, 0.5 mg/L IAA, 100 mg/L kanamycin and 350 mg/L cefotaxime (selection medium). Regenerating explants were transferred to fresh selection medium after 2–3 weeks. Adventitious shoots which survived the kanamycin selection were isolated and transferred to MS medium containing 1 mg/L IBA, 100 mg/L kanamycin and 350 mg/L cefotaxime for root induction. When roots reached 2–3 cm in length the transgenic tobacco plantlets were transplanted to soil as described for petunia.

Anthocyanidin analysis

Prior to HPLC analysis the anthocyanin molecules present in petal extracts were acid hydrolysed to remove glycosyl moieties from the anthocyanidin core. The hydroxylation pattern on the B ring of the anthocyanin pigments was determined by HPLC analysis of the anthocyanidin core molecule. The HPLC system used in this analysis was a Hewlett-Packard 1050 equipped with a multiwavelength detector (MWD). Reversed phase chromatographic separations were performed on a Spherisorb S5 ODS2 cartridge column, 250 mm×4 mm ID.

a. Extraction of anthocyanins and flavonoids

Flower pigments were extracted from petal segments (ca. 50 mg) with 5 ml of methanol containing 1% (v/v) of aqueous 6M hydrochloric acid. Extracts were diluted with water (1:9) and filtered (Millex HV, 0.45$\mu$) prior to injection into the HPLC system.

b. Hydrolysis of anthocyanins

Crude methanolic extracts (100 $\mu$L) obtained in a. above were evaporated to dryness in Pierce Reacti-Vials using a stream of dry nitrogen at room temperature. The residues were dissolved in 200 $\mu$L 2M HCl, vials were capped and then heated at 100° C. for thirty minutes. Hydrolysis mixtures were diluted with water (1:9) and filtered (Millex HV, 0.45$\mu$) prior to HPLC analysis.

c. Chromatography

Separation of flower pigments was effected via gradient elution using the following system:

Solvent A: (triethylamine:conc. $H_3PO_4$:$H_2O$) (3:2.5:1000)

Solvent B: acetonitrile

Gradient Conditions: 5% B to 40% B over 20 minutes

Flow Rate: 1 ml/min

Temperature: 35° C.

Detection: MWD with simultaneous data acquisition at 280, 350 and 546 nm.

The anthocyanidin peaks were identified by reference to known standards.

2. Cloning and Analysis of 3',5'-Hydroxylase

Characterisation of the 3',5'-Hydroxylase Enzyme a. Developmental Regulation

Extracts of P. hybrida cv. OGB petals harvested from flowers at the different stages of development defined above were assayed for 3',5'-hydroxylase activity.

3',5'-Hydroxylase enzyme activity in OGB petals was found to be developmentally regulated during maturation of the corolla (FIG. 2B). This developmental profile paralleled the expression of other genes involved in flavonoid biosynthesis. Activity of the 3',5'-hydroxylase enzyme and expression of chalcone synthase (CHS), chalcone flavanone isomerase (CHI), dihydroflavonol reductase (DFR) genes peaked around stages 3 to 4 of flower development.

b. Induction of 3',5'-Hydroxylase Activity in Leaf Tissue

Genes of the flavonoid pigment biosynthetic pathway are not normally expressed in leaf tissue. However, synthesis of delphinidin pigments was induced in OGB leaves by incubation in a 2% (w/v) glucose solution in high light. Under these conditions, 3',5'-hydroxylase enzyme activity can be detected in OGB leaf tissue. Maximal induction of enzyme activity was shown to occur after 96 hours of the glucose/high light treatment. Under these conditions the expression of several other pigment biosynthesis genes was also induced to levels comparable to those observed in emerging petals. It was concluded from these results that the Hf1 and/or Hf2 genes are induced in glucose/high light treated leaf tissue.

c. Evidence that the 3',5'-Hydroxylase Belongs to the Cytochrome P450 Class of Enzymes 3',5'-Hydroxylase activity in OGB petals was shown to be associated with the microsomal fraction and dependent upon the presence of NADPH. Activity could be inhibited by treatment of the microsomes with carbon monoxide and by two inhibitors that specifically inactivate cytochrome P450 enzymes: tetcyclasis and 1-aminobenzotriazine (Taton et al, 1988; Matthews et al, 1985; Rademacher et al, 1987).

Construction of a cDNA Library Enriched for Cytochrome P450 Sequences

Translation of cytochrome P450 mRNAs occurs on membrane-bound polysomes (Takemori and Kominami, 1989). Therefore, in order to enrich for cytochrome P450 sequences (including 3',5'-hydroxylase sequences) a cDNA library was constructed using membrane-bound polysomal RNA isolated from OGB petals of stage 3 to 4 flowers. Isolation of the petal RNA from stage 3 to 4 flowers, ensured that 3',5'-hydroxylase sequences were maximally represented in the library since 3',5'-hydroxylase activity had been shown to be maximal at this stage of development (see above and FIG. 2B). The resultant library, designated cDNA library #1, contained 250,000 primary recombinants.

PCR Amplification of a Petunia Petal Cytochrome P450 cDNA

A large number of cytochromes P450 have been sequenced, from organisms as diverse as vertebrates, fungi, insects, bacteria and one plant (Nebert et al, 1991, Bozak et al, 1990). A characteristic of all these enzymes is the existence of a number of small regions of sequence conservation, especially around the cysteine residue involved in haem binding. The amino acid sequence F(G, S)XGXRXCXG is present in the haem-binding domain of nearly all microsomal cytochromes P450 sequenced to date, where X can be any amino acid (FIG. 3). This consensus sequence was compared with the NBRF protein database, using the FASTA program (Pearson and Lipman, 1988), to determine the frequency of occurrence of amino acids around this area for all of the microsomal cytochrome P450 sequences in the database. This analysis showed that the most common amino acid sequence for each position around the haem-binding domain was:

F<u>MPFGAG</u>XRXCLG

An oligonucleotide was designed to hybridize to a gene encoding the underlined sequence and similar sequences. This oligonucleotide, designated oligo 1, is shown below:

5'-<u>GGAAGCTT</u>ATICCITT(T/C)GGIGCIGG-3'

The underlined portion is additional sequence which includes a HindIII recognition site to facilitate directional cloning of PCR products. The inclusion of deoxyinosine (I) covered the different possibilities for codon usage where more than two codons could encode the same amino acid. Deoxyinosine base-pairs with similar efficiency to A, T, G and C (Martin et al, 1985; Ohtsuka et al, 1985).

Plasmid DNA obtained from cDNA library #1 as described in the Materials and Methods was used as a template for the amplification of a 360 bp cytochrome P450 related sequence using oligos 1 and 2 (FIG. 3). Oligo 2 corresponded to the −20 primer (Stratagene) plus a GCN4 binding site (Lew and Kemp, 1989) at the 5' end. The PCR fragment was cloned into pBluescript and the resulting plasmid was designated pCGP450. The 5' region of pCGP450 encoded a polypeptide sequence with significant homology to previously sequenced cytochrome P450 molecules.

Isolation of Cytochrome P450 Homologues from a Petunia Petal cDNA Library

Plasmid pCGP450 was used to screen cDNA library #1 (60,000 plaques) for related clones. Two consecutive hybridizations under conditions of high and low stringency were used to detect both sibling clones of pCGP450 and a second group of cytochrome P450 cDNAs. A representative cDNA clone of each of the sibling groups was selected for subsequent analyses. The pCGP450 sibling was designated pCGP142 and the representative of the second group was designated pCGP147. A SalI-EcoRI fragment that included only the coding sequences of pCGP147 was then used to re-probe 16,000 plaques from cDNA library #1 at low stringency. A total of 20 clones that hybridized to the probe were sequenced, allowing two further cytochrome P450 homologues to be identified: pCGP158 and pCGP160 (FIG. 4A).

Isolation of an Additional Petal Cytochrome P450 Homologue by PCR

Sequence information from around the putative haem-binding domain of the petunia clones pCGP142, pCGP147 and a previously sequenced avocado cytochrome P450 sequence (O'Keefe and Leto, 1989; Bozak et al, 1990) was used, as described in the Materials and Methods, to design a second degenerate oligonucleotide (oligo 3) which covered amino acid sequences encoded by at least two of the three cytochrome P450 clones. This oligonucleotide was used to amplify related sequences by PCR using cDNA library #1 as the template and oligo 4 as the second primer (FIG. 3B). Reaction products in the size range 250–500 bp were isolated as described in Materials and Methods and cloned into the ddT-tailed pBluescript vector described by Holton and Graham (1991). The cloned PCR fragments were sequenced and shown to encode a fifth cytochrome P450 homologue. One clone, designated pCGP454, was chosen for further analysis.

Isolation of Further Cytochrome P450 Homologues from cDNA Library #1

Figure 5B:
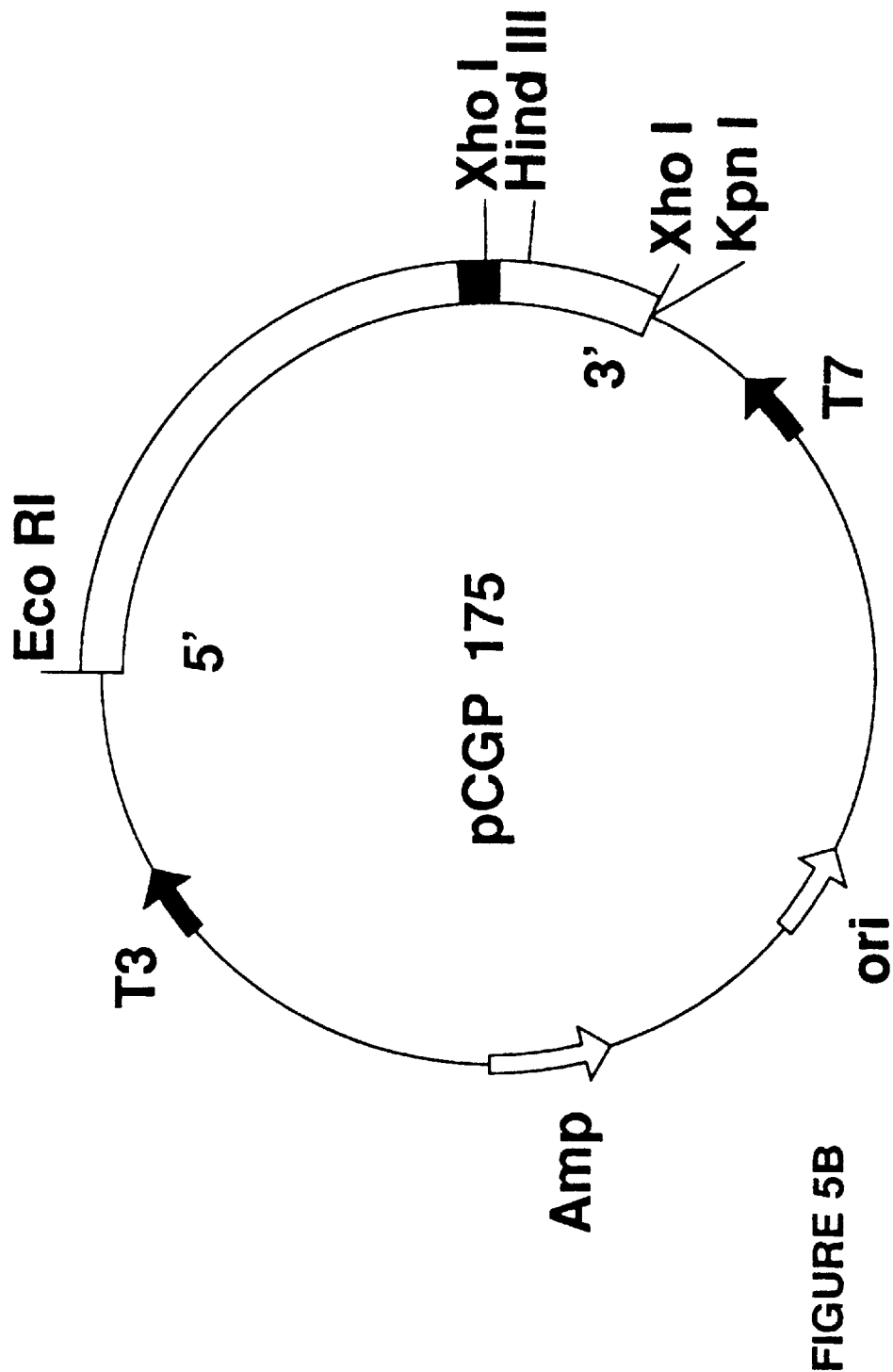

A mixed probe of $^{32}$P-labelled DNA fragments that included the coding regions of the cytochrome P450 homologues pCGP142, pCGP147, pCGP158 and pCGP160 and the cDNA insert from pCGP454 (FIGS. 4B to 4H) was used to screen 50,000 recombinants from cDNA library #1 for related sequences. A total of 152 hybridizing clones were detected under low stringency hybridization and washing conditions. A further 13 different cytochrome P450 homologues were identified by sequence analysis of DNA isolated from the hybridizing clones. Two closely related sibling groups were distinguished amongst these clones. The coding regions of each of the two groups showed 94% homology or similarity at the DNA level. Two representatives of one sibling group, pCGP174 (FIG. 5A) and pCGP176, and one representative of the other sibling group, pCGP175 (FIG. 5B), were chosen for further study.

Northern and RFLP Analysis of the Cytochrome P450 Homologues

Northern and RFLP analyses were used to distinguish which cytochrome P450 homologues had the molecular characteristics of a cDNA encoding a 3',5'-hydroxylase. There are two genetic loci in *P. hybrida*, Hf1 and Hf2, that control 3',5'-hydroxylase activity (de Vlaming et al, 1984; Wiering, 1974). Hf1 is expressed in both the limb and the tube of *P. hybrida* flowers and gives rise to much higher levels of 3',5'-hydroxylase activity than does Hf2 which is only expressed in the limb. Petunia 3',5'-hydroxylase activity is also developmentally and spatially regulated. Under normal growth conditions, the enzyme can only be detected in petal tissues, increasing to maximal levels around stages 3–4 of flower development and then declining in the fully open flower (stage 5; see FIG. 2(B)). Activity can also be induced in leaf tissue under certain stress conditions such as the glucose/high light treatment described above. Accordingly, a cDNA clone encoding a 3',5'-hydroxylase was expected to have an expression profile on RNA blots that paralleled the enzyme activity profile. It was also expected that a cDNA clone encoding a *P. hybrida* 3',5'-hydroxylase would map to either the Hf1 or Hf2 loci. Hf1 has been mapped to chromosome I of the *P. hybrida* genome and is linked to the Ph1 locus (Cornu, 1984; Cornu et al, 1990) while Hf2 is closely linked to Po on chromosome V (Wallroth et al, 1986). RFLP analysis of DNA isolated from a $F_2$ population of plants derived from a cross between the inbred lines V23 (Hf1/Hf1, Hf2/Hf2) and R51 (hf1/hf1, hf2/hf2) was used to obtain linkage data for the various cytochrome P450 homologues. An Hf1/- genotype was assigned to $F_2$ plants that had 3',5'-hydroxylase activity in the flower tube. In addition, it was possible to assign an Hf1/Hf1 genotype to plants in the $F_2$ population based on linkage to the ph1 gene which influences the pH of the petal vacuole (Wiering and de Vlaming, 1984).

The V23 parent line (Hf1/Hf1) also had a ph1/ph1 genotype which results in a petal homogenate pH of approximately 6.2. Since Ph1/- plants have a petal homogenate pH of 5.3 it was possible to distinguish ph1/ph1 (Hf1/Hf1) plants within the R51×V23 $F_2$ population by assaying the pH of petal homogenates.

The linkage between the Hf2 and Po loci was used to distinguish candidate Hf2 clones. The Po locus has been shown to correspond to the *P. hybrida* chi-A gene which encodes the enzyme chalcone flavanone isomerase (van Tunen et al, 1991). A cDNA clone of chi-A could therefore be used in the RFLP analysis to assign a Po or po genotype to individuals in the $F_2$ population. Since V23 has an Hf2/Hf2, po/po genotype it was possible to determine linkage to the Hf2 locus by co-segregation of the V23-like and R51-like RFLP patterns with the po and Po patterns detected by the chi-A probe.

cDNA fragments that corresponded to the 3' untranslated region of the cytochrome P450 homologues were used to probe RNA blots and Southern blots of genomic DNA isolated from individual plants in V23×R51 $F_2$ population. By this analysis it was shown that the genes corresponding to cDNA clones pCGP174 and pCGP175 were expressed in a manner that paralleled 3',5'-hydroxylase activity. Furthermore, the gene corresponding to pCGP174 was shown to be closely linked to the Hf1 locus and pCGP175 was linked to the Hf2 locus.

a. pCGP 174

A 330 bp HindIII-KpnI 3' fragment from clone pCGP174 (FIG. 5A) gave a pattern of hybridization on both RNA and DNA blots that suggested that this clone corresponded to the Hf1 locus (FIG. 6). The gene was expressed in both limb and tube tissues and had a developmental profile that paralleled 3',5'-hydroxylase activity, peaking in Stage 3 petal limbs. No expression was detected in leaf, but was induced in this tissue by the glucose/high light treatment. Furthermore, there was no detectable expression of the gene in the petal tissue of the hf1/hf1 mutant lines R51 or Sw63. By contrast, relatively high levels of expression were detected in the Hf1/Hf1 lines V23 and Th7 and the V23×R51 hybrid (FIG. 6A).

On Southern blots of genomic DNA digested with XbaI, the 330 bp HindIII-KpnI 3' fragment from pCGP174 detected two RFLPs that segregated independently in the V23×R51 $F_2$ population. RFLP #1 corresponded to strongly hybridizing DNA bands while RFLP #2 corresponded to weakly hybridizing bands (see FIG. 6B). Eleven out of 12 plants that had been assigned a ph1/ph1 genotype had a V23-like pattern for RFLP #1 and 49 out of 49 plants that had 3',5'-hydroxylase activity in the tube had either a V23- or VR-like pattern for RFLP #1. In addition, for a total of 32 plants, there was complete co-segregation of the V23, VR and R51 RFLP patterns for chi-A (po) with the corresponding patterns of RFLP #2.

These data provided strong evidence that pCGP174 encoded a 3',5'-hydroxylase and corresponded to the Hf1 locus (RFLP #1) and that the 3' probe cross-hybridized to the Hf2 locus (RFLP #2).

b. pCGP175

A 320 bp HindIII/XhoI 3' fragment from clone pCGP175 (FIG. 5B) gave a pattern of hybridization on both RNA and DNA blots that suggested that this clone corresponded to the Hf2 locus (FIG. 7). The Northern analysis showed that the gene was developmentally regulated in a similar way to pCGP174, with maximal expression in Stage 3 OGB petal limbs, however no expression was detected in OGB tube tissue. The gene was also expressed in the petal tissue of V23 (Hf2/Hf2), Th7 (Hf2/Hf2) and the V23×R51 hybrid (FIG. 7A).

On Southern blots, the 320 bp HindIII/XhoI fragment from pCGP175 hybridized to the same genomic fragments produced by XbaI digestion of V23 and R51 genomic DNA that weakly hybridized to the pCGP174 3' probe (RFLP #2). There was complete co-segregation of the V23-, VR- and R51-like RFLP patterns detected by the pCGP175 3' probe and the corresponding RFLP patterns for chi-A (Po) (FIG. 7B).

Yeast expression experiments (see below) subsequently confirmed that pCGP175 and a sibling of pCGP174 (pCGP176) both encoded a 3',5'-hydroxylase. In addition, expression of a full-length version of pCGP174 in an hf1/hf1, hf2/hf2 Petunia mutant resulted in increased 3',5'-hydroxylase activity and production of 3',5'-hydroxylated anthocyanins above the low basal levels normally found in the non-transgenic plant. Taken together with the RFLP results, it was concluded from these data that pCGP174 correspond to the Hf1 locus and pCGP175 correspond to the Hf2 locus.

Isolation of Full-Length Hf1 cDNA Clones and Sequence Analysis

From preliminary sequence analysis it was shown that pCGP174 did not represent a full-length clone of the corresponding transcript while pCGP175 included a putative initiation codon and was presumed to be a full-length cDNA. Sequence analysis also showed that pCGP176 was a longer version of pCGP174 and included an ATG codon 17 bp from the 5' end. However, from this analysis alone it was not possible to confidently predict whether pCGP176 included the entire coding region of this gene. Accordingly, cDNA library #2 was screened for longer clones of the pCGP174/pCGP176 sibling group. Approximately $1.5 \times 10^5$ recombinants from cDNA library #2 were screened for clones that hybridized to the 0.33 kb HindIII-KpnI 3' fragment from pCGP174. Two hybridizing clones, designated pCGP601 and pCGP602 were chosen for further analysis. Both pCGP601 and pCGP602 included presumptive translation initiation codons, but pCGP602 encoded a longer 5' untranslated region.

A restriction enzyme map of pCGP602, indicating the methodology adopted for sequencing the clone and the oligonucleotide primer sequences used to obtain overlapping sequence information, is shown in FIG. 8.

The nucleotide sequence and deduced amino acid sequence of the sibling clones pCGP176 and pCGP602 are shown in FIG. 9. Similarly, FIG. 10 shows the nucleotide sequence and deduced translation product of pCGP175.

Using an alignment generated by the LFASTA program (Pearson and Lipman, 1988), the amino acid sequences encoded by the petunia 3',5'-hydroxylase genes were found to share 94% positional identity. The nucleotide sequences are 94% identical. Based on the classification scheme for cytochromes P450, this sequence similarity would place both genes in the same family/sub-family. Because the 3',5'-hydroxylase amino acid sequences share less than 40% identity with any previously characterised member of the cytochrome P450 superfamily, the corresponding genes belong to a new P450 family separate from all other P450 genes.

Expression of pCGP175 cDNA in Yeast

The cDNA insert from pCGP175 was ligated in a sense orientation behind the glyceraldehyde-3-phosphate dehydrogenase promoter in the yeast vector pYGA22m. The resulting construct, designated pCGP618 (FIG. 11) was transformed into the yeast strain G-1315 (Ashikari et al, 1989). A single transformant was grown in 50 mL of YNBC at 30° C. for 2 days. A microsomal fraction prepared from this culture was shown to have 3',5'-hydroxylase activity while an equivalent fraction prepared from non-transformed yeast had no activity (FIG. 12). From this it was concluded that the cDNA insert from pCGP175 encoded a 3',5'-hydroxylase.

Expression of pCGP176 cDNA in Yeast

The cDNA insert from pCGP176 was ligated in a sense orientation behind the glyceraldehyde-3-phosphate dehydrogenase promoter in the yeast vector pYGA22m. The resulting construct, designated pCGP620 was transformed into the yeast strain G-1315. An extract prepared from the transformed yeast was shown to have 3',5'-hydroxylase activity while an equivalent fraction prepared from non-transformed yeast had no activity (FIG. 13). From this it was concluded that the cDNA insert from pCGP176 encoded a 3',5'-hydroxlase.

Expression of an Hf1 cDNA a. Expression in the hf1/hf1, hf2/hf2 *P. hybrida* F$_1$ hybrid Skr4×Sw63

The pCGP602 cDNA insert was ligated behind the Mac promoter of the Ti-binary vector pCGP293. The resulting construct, designated pCGP90 (FIG. 14), was introduced into the F$_1$ Petunia hybrid Skr4×Sw63 using Agrobacterium-mediated gene transfer. Leaf discs of Skr4×Sw63 were co-cultivated with AGL0/pCGP90 and integration of the pCGP602 cDNA insert in the Skr4×Sw63 genome was confirmed by Southern analysis of plants obtained after kanamycin selection.

The transgenic plants had significantly higher levels of both 3',5'-hydroxylase enzyme activity (FIG. 15) and 3',5'-hydroxylated anthocyanins (Table 3A) than the non-transgenic Skr4×Sw63 hybrid. Although Skr4×Sw63 is homozygous recessive for both the Hf1 and Hf2 genes these mutations do not completely block enzyme production as low levels of 3',5'-hydroxylase activity were detected in Skr4×Sw63 petal extracts (FIG. 15). In addition, low levels (100 μg/gm) of malvidin were detected in acid hydrolysed Skr4×Sw63 petal extracts (Table 3A). Introduction of the Hf1 cDNA significantly increased the level of 3',5'-hydroxylase activity in petal limb tissue (FIG. 15) and acid hydrolysed extracts of petals from the transgenic plants had four times the level of malvidin detected in the non-transgenic control (Table 3A).

b. Expression in *Nicotiana tabacum* cultivar Xanthi

Tobacco (*N. tabacum* cv Xanthi) flowers produce cyanidin as the sole anthocyanidin. Transformation of tobacco with pCGP90 led to the accumulation of significant amounts of delphinidin in the flowers, in addition to cyanidin (shown in Table 3A).

TABLE 3A

Pigment Analysis
Anthocyanidin levels found in acid hydrolysed petal extracts

| Plant | Malvidin (μg/gm petal) | Cyanidin (μg/gm petal) | Delphinidin (μg/gm petal) |
| --- | --- | --- | --- |
| Petunia | | | |
| Skr4 × Sw63 | 100 | nd[1] | nd |
| Skr4 × Sw63/pCGP90 | 410 | nd | nd |
| Tobacco | | | |
| non-co-cultivated control | nd | 272 | nd |
| Transgenic tobacco | nd | 229 | 36 |

[1]not detected c. Expression in the hf1/hf1, hf2/hf2 *P. hybrida* F$_1$ hybrid Rp57×Rw14

The petunia line Rp57×Rw14 was transformed using pCGP90 and a procedure similar to that used for Skr4×Sw63. Transgenic flowers produced considerable amounts of petunidin and malvidin which were not detectable in the non-transformed plants (Table 3B). Petunidin and malvidin are both methylated derivatives of delphinidin.

TABLE 3B

Pigment Analysis of high pH line Rp57 × Rw14.
Percentages of anthocyanidins found in acid hydrolysed petal extracts

| Plant | Cyanidin (%) | Peonidin (%) | Petunidin (%) | Malvidin (%) |
| --- | --- | --- | --- | --- |
| Petunia | | | | |
| Rp57 × Rw14 | 5.0 | 95.0 | 0 | 0 |
| Rp57 × Rw14/pCGP90 | 0 | 45.2 | 7.8 | 47.0 |

The expression of the introduced Hf1 cDNA in the Skr4×Sw63 hybrid had a marked effect on flower colour. The carpel and stamen tissue of the non-transgenic flowers are white whereas these same tissues in the transgenic plants were a blue/purple colour. In addition, expression of the Hf1 cDNA in the Skr4×Sw63 hybrid conferred a deep pink/violet hue to the corolla which is normally very pale pink. In the case of tobacco, the production of delphinidin derivatives led to a minor blueing of senescing flowers. Expression of the Hf1 cDNA in the Rp57×Rw14 hybrid again had a marked effect on flower colour. Non-transgenic Rp57×Rw14 flowers are pink, with peonidin being the major anthocyanidin present (see Table 3B). Transformation with Hf1 cDNA led to a marked blueing of flower colour.

The colour changes observed may also be described in terms of numbers from the Royal Horticultural Society's Colour Chart. In general, the changes can be described as moving the colour from the pale-to-mid pink hues of 60C/D–65C/D, to the darker bluer/purpler hues represented by many, but not all, of the colour squares between 70 and 85. Although not wishing to limit the possible colour changes which may be achieved, some of the colours observed in the Skr4×Sw63 hybrid could be described, approximately, as having changed from 65B (untransformed) to 70B and to 74B (both transformed). Likewise, several in the Rp57× Rw14 hybrid might be described as moving from 64C to 72B to 77B and to 82B. It should be remembered that other biochemical and physiological conditions will affect the individual outcome and the citing of specific colours achieved should not be interpreted as defining the possible range.

Detection of Putative 3',5'-hydroxylase Gene Sequences in Other Plant Species

The presence of 3',4',5'-hydroxylated flavonoids is correlated with the presence of 3',5'-hydroxylase activity and therefore the 3',5'-hydroxylase gene. It would be expected that these genes from other species would hybridize with the petunia 3',5'-hydroxylase gene under conditions of low stringency. RNA (FIG. 16) and/or DNA (FIG. 17) was isolated from a number of delphinidin-producing plants, probed with $^{32}$P-labelled Hf1 cDNA and washed under different conditions of stringency. Hybridizing bands were detected in every example. Therefore, the isolation of 3',5'-hydroxylase genes from other delphinidin-producing plants should be possible using a petunia 3',5'-hydroxylase gene as a probe.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

REFERENCES:

Asen, S., Stewart, R. N. and Norris, K. H. *Phytochemistry* 14: 2677–2682, 1975.

Asen, S., Griesbach, R. J., Norris, K. H. and Leonhardt, B. A. *Phytochemistry* 25: 2509–2513, 1986.

Ashikari, T., Kiuchi-Goto, N., Tanaka, Y., Shibano, Y., Amachi, T., and Yoshizumi, H. *Appl. Microbiol. Biotechnol.* 30: 515–520, 1989.

Aviv, H. and Leder, P., *Proc. Natl. Acad. Sci. USA* 69: 1408–1412, 1972.

Beale, G. H. *Journal of Genetics* 40(3): 337–358, 1940.

Bethesda Research Laboratories. BRL pUC host: *E. coli* DH5α™ competent cells. *Bethesda Res. Lab. Focus.* 8(2): 9, 1986.

Bozak, K. R., Yu, H., Sirevag, R. and Christoffersen, R. E., *Proc. Natl. Acad. Sci. USA* 87: 3904–3908, 1990.

Bullock, W. O., Fernandez, J. M. and Short, J. M. *Biotechniques* 5: 376, 1987.

Comai, L., Moran, P. and Maslyar, D., *Plant Molecular Biology* 15: 373–381, 1990.

Cornu, A., Genetics. In: *Petunia Sink,* K. C. (Ed). Springer-Verlag, Berlin, Germany pp 35–47, 1984.

Cornu, A., Farcy, E., Maizonnier, D., Haring, M., Veerman, W. and Gerats, A. G. M. In *Genetic maps - Locus maps of complex genomes* 5th edition, Stephen J. O'Brien (Ed), Cold Spring Harbor Laboratory Press, USA, 1990.

Dellaporta, S. J., Wood, J. and Hick, J. B. *Plant Mol. Biol. Rep.* 1: 19–21, 1983.

De Vlaming, P., Gerats, A. G. M., Wiering, H. and Wijsman, H. J. W. *Plant Mol. Biol. Rep.* 2(2): 21–42, 1984.

Doodeman, M., Gerats, A. G. M., Schram, A. W., de Vlaming, P. and Bianchi, F. *Theor. Appl. Genet.* 67: 357–366, 1984.

Ebel, J. and Hahlbrock, K., In *The Flavonoids: Advances in Research Since* 1980. Harborne, J. B. (Ed.), Academic Press, New York, USA, 641–679, 1988.

Forkmann, G. *Plant Breeding* 106: 1–26, 1991.

Forkmann, G. and Stotz, G. Z. *Naturforsch* 36c: 411–416, 1981.

Garfinkel, D. J. and Nester, E. W. *J. Bacteriol.* 144:732–743, 1980.

Hagmann, M., Heller, W. and Grisebach, H. *Eur. J. Biochem.* 134: 547–554, 1983.

Hahlbrock, K. and Grisebach, H. *Annu. Rev. Plant Physiol.* 30: 105–130, 1979.

Hanahan, D. *J. Mol. Biol.* 166: 557, 1983.

Harborne, J. B. and Simmonds, N. W. *Annu. Rep. John Innes Inst.* 53: 29–30, 1962.

Heller, W. and Forkmann, G. In: *The Flavonoids, Advances in Research Since* 1980. Harborne, J. B. (Ed.), Academic Press, New York, 1988.

Holton, T. A. and Graham, M. W. *Nucleic Acids Research* 19: 1156, 1991.

Inoue, H., Nojima, H. and Okayama, H. *Gene* 96: 23–28, 1990.

Ito, H., Fukuda, Y., Murata, K. and Kimura, A. *J. Bacteriol.,* 153: 163–168, 1983.

Jefferson, R. A., Kavanagh, T. A. and Bevan, M. W. *EMBO J.* 6(13): 3901–3907, 1987.

Koes, R. E., Spelt, C. E., Reif, H. J., van den Elzen, P. J. M., Veltkamp, E. and Mol, J. N. M. *Nucl. Acids Res.* 14(13): 5229–5239, 1986.

Larson, R. L. and Bussard, J. B. *Plant Physiol.* 80: 483–486, 1986.

Lazo, G. R., Pascal, A. S. and Ludwig, R. A. *Bio/technology* 9: 963–967, 1991.

Lew, A. M. and Kemp, D. J. *Nucl. Acids Res.* 17(14): 5859–5860, 1989.

McBride, K. E. and Summerfelt, K. R. *Plant Molecular Biology* 14: 269–276 1990.

Martin, F. M., Castro, N. M., Aboula-ela, F., Tinoco, I. *Nucl. Acids Res.* 13: 8927–8938, 1985.

Matthews, J. M., Dostal, L. A. and Bend, J. R. *J. Pharmacology and Experimental Therapeutics* 235(1): 186–190, 1985.

Merrifield, *J. Am. Chem. Soc.* 85: 2149, 1964.

Murashige, T. and Skoog, F. *Physiol. Plant* 15: 73–97, 1962.

Nebert, D. W., Nelson, D. R., Coon, M. J., Estabrook, R. W., Feyereisen, R., Fujii-Kuriyama, Y., Gonzalez, F. J., Guengerich, F. P., Gunsalus, I. C. Johnson, E. F., Loper, J. C., Sato, R., Waterman, M. R., Waxman, D. J. *DNA and Cell Biology* 10: 1–14, 1991.

Norrander, J., Kemp, T. and Messing, J. *Gene* 26: 101, 1983.

Oeda, K., Sakaki, T., and Ohkawa, H. *DNA* 4: 203–210, 1985.

O'Keefe, D. P. and Leto, K. J. *Plant Physiol.* 89: 1141–1149, 1989.

Ohtsuka, E., Matsuki, S., Ikehara, M., Takahashi, Y. and Matsubara, K. *J. Biol. Chem.* 260(5): 2605–2608, 1985.

Pearson, W. R. and Lipman, D. J. *Proc. Natl. Acad. Sci. USA* 85: 2444–2448, 1988.

Rademacher, W., Fritsch, H., Graebe, J. E., Sauter, H. and Jung, J. *Pesticide Science* 21: 241–252, 1987.

Sambrook, J., Fritsch, E. F. and Maniatis, T. *Molecular Cloning: A Laboratory Manual* (2nd edition). Cold Spring Harbor Laboratory Press, USA, 1989.

Sanger, F., Nicklen, S. and Coulson, A. *Proc. Natl. Acad. Sci. USA* 74: 5463–5467, 1977.

Schenk, R. U. and Hilderbrandt, A. C. *Can. J. Bot.* 50: 199–204, 1972.

Schram, A. W., Jonsson, L. M. V. and Bennink, G. J. H. Biochemistry of flavonoid synthesis in *Petunia hybrida*. In: *Petunia Sink,* K. C. (ed.) Springer-Verlag, Berlin, Germany pp 68–75, 1984.

Stafford, H. A. *Flavonoid Metabolism* CRC Press, Inc. Boca Raton, Fla., USA, 1990.

Stotz, G. and Forkmann, G. Z. *Naturforsch* 37c: 19–23, 1982.

Stotz, G., de Vlaming, P., Wiering, H. and Forkmann, G. *Theor. Apppl. Genet.* 70: 300, 1985.

Takeda, K., Kubota, R. and Yagioka, C. *Phytochemistry* 24: 1207, 1985.

Takemori, S. and Kominami, S. *Cytochrome P450.* Tokyo University Press, Japan, 1989.

Taton, M., Ullman, P., Beneveniste, P. and Rahier, A. *Pesticide Biochemistry and Physiology* 30: 178–189, 1988.

Turpen, T. H. and Griffith, O. M. *BioTechniques* 4: 11–15, 1986.

van Tunen, A. J., Gerats, A. G. M. and Mol, J. N. M. *Plant Mol. Biol. Rep.* 8: 50–59, 1990.

van Tunen, A. J., Koes, R. E., Spelt, C. E. van der Krol, A. R., Stuitje, A. R. and Mol., J. N. M. *EMBO J.* 7(5): 1257–1263, 1988.

van Tunen, A. J., Mur, L. A., Recourt, K., Gerats, A. G. M. and Mol., J. N. M. *The Plant Cell* 3: 39–48, 1991.

von Wettstein-Knowles, P. *Hereditas* 60: 317–346, 1968.

Vercruysse, S. A. R., Delcour, J. A. and Dondeyne, P. *J. Chromatography* 324: 495–497, 1985.

Wallroth, M., Gerats, A. G. M., Rogers, S. G., Fraley, R. T. and Horsch, R. B. *Mol. Gen. Genet.* 202: 6–15, 1986.

Wiering, H. and De Vlaming, P. Inheritance and Biochemistry of Pigments. In: *Petunia Sink,* K. C. (Ed.), Springer-Verlag, Berlin, Germany pp 49–65, 1984.

Wiering, H. *Genen Phaenen* 17(1-2): 117–134, 1974

Yanisch-Perron, C., Vieira, J. and Messing, J. *Gene* 33: 103, 1985.

---

We claim:

1. An isolated and purified 3',5'-hydroxylase enzyme capable of hydroxylating dihydrokaempferol.

2. The enzyme of claim 1 wherein said enzyme is of petunia, verbena, delphinium, grape, iris, freesia, hydrangea, cyclamen, potato, pansy or eggplant origin.

3. The enzyme of claim 2 wherein said enzyme is of petunia origin.

4. The enzyme of claim 3 wherein said enzyme has an amino acid sequence encoded by the nucleic acid of SEQ ID NO:28 or SEQ ID NO:29.

5. A method of producing a 3',5'-hydroxylase capable of hydroxylating DHK which comprises:

(a) transforming a suitable host cell with an expression vector comprising an isolated nucleic acid encoding said 3',5'-hydroxylase;

(b) culturing said host cells under conditions in which said cells express said isolated nucleic acid and produce said 3',5'-hydroxylase; and (c) recovering said 3',5'-hydroxylase.

6. The method of claim 5 wherein said nucleic acid is isolatable from petunia, verbena, delphinium, grape, iris, freesia, hydrangea, cyclamen, potato, pansy or eggplant.

7. The method of claim 6 wherein said nucleic acid is isolatable from petunia.

8. The method of claim 7 wherein said isolated nucleic acid has the nucleotide sequence of SEQ ID NO:28 or SEQ ID NO:29.

9. The method of claim 5 wherein said host cell is a yeast cell.

* * * * *

UNITED STATES PATENT AND TRADEMARK OFFICE
CERTIFICATE OF CORRECTION

PATENT NO. : 5,861,487
DATED : January 19, 1999
INVENTOR(S) : T.A. Holton, et al.

It is certified that error appears in the above-identified patent and that said Letters Patent are hereby corrected as shown below:

Column 12, TABLE 2, Line 26: "HF2" should read --Hf2--

Column 13, Line 56: "(1986)." should read --(1986)--

Signed and Sealed this

Fifteenth Day of May, 2001

Attest:

NICHOLAS P. GODICI

Attesting Officer

Acting Director of the United States Patent and Trademark Office